(12) United States Patent
Boye et al.

(10) Patent No.: US 11,806,408 B2
(45) Date of Patent: Nov. 7, 2023

(54) METHODS AND COMPOSITIONS FOR TREATING CONE-ROD RETINAL DYSTROPHY

(71) Applicants: University of Florida Research Foundation, Incorporated, Gainesville, FL (US); Editas Medicine, Inc., Cambridge, MA (US)

(72) Inventors: Shannon E. Boye, Gainesville, FL (US); Sanford L. Boye, Gainesville, FL (US); Morgan Maeder, Jamaica Plain, MA (US)

(73) Assignees: University of Florida Research Foundation, Incorporated, Gainesville, FL (US); Editas Medicine, Inc., Cambridge, MA (US)

( * ) Notice: Subject to any disclaimer, the term of this patent is extended or adjusted under 35 U.S.C. 154(b) by 489 days.

(21) Appl. No.: 16/642,582

(22) PCT Filed: Aug. 28, 2018

(86) PCT No.: PCT/US2018/048405
§ 371 (c)(1),
(2) Date: Feb. 27, 2020

(87) PCT Pub. No.: WO2019/046341
PCT Pub. Date: Mar. 7, 2019

(65) Prior Publication Data
US 2020/0345865 A1 Nov. 5, 2020

Related U.S. Application Data

(60) Provisional application No. 62/664,063, filed on Apr. 27, 2018, provisional application No. 62/551,212, filed on Aug. 28, 2017.

(51) Int. Cl.
| | | |
|---|---|---|
| *A61K 48/00* | (2006.01) | |
| *C12N 15/79* | (2006.01) | |
| *C07H 21/04* | (2006.01) | |
| *A61K 35/761* | (2015.01) | |
| *C12N 15/86* | (2006.01) | |
| *C07H 21/02* | (2006.01) | |

(52) U.S. Cl.
CPC .......... *A61K 48/005* (2013.01); *A61K 35/761* (2013.01); *A61K 48/0075* (2013.01); *C12N 15/86* (2013.01); *C07H 21/02* (2013.01); *C07H 21/04* (2013.01); *C12N 2310/20* (2017.05); *C12N 2750/14143* (2013.01); *C12N 2800/80* (2013.01)

(58) Field of Classification Search
CPC ...... A61K 48/005; C12N 15/85; C12N 15/86; C12N 2310/20; C12N 2750/14143; C07H 21/02; C07H 21/04
See application file for complete search history.

(56) References Cited

U.S. PATENT DOCUMENTS

| | | |
|---|---|---|
| 9,816,108 B2 | 11/2017 | Boye et al. |
| 2013/0210895 A1 | 8/2013 | Boye et al. |
| 2016/0340661 A1 | 11/2016 | Cong et al. |
| 2018/0100165 A1 | 4/2018 | Boye et al. |

FOREIGN PATENT DOCUMENTS

| | | | |
|---|---|---|---|
| WO | WO 2016/176690 A2 | * | 11/2016 |
| WO | WO 2019/116349 A1 | | 6/2019 |

OTHER PUBLICATIONS

Kotterman et al., 2014, Nature Reviews, vol. 15, p. 445-451.*
Shim et al., 2017, Current Gene Therapy, vol. 17, No. 5, p. 1-18.*
Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
Durymanov et al., 2018, Frontiers in Pharmacology, vol. 9, Article 971, p. 1-15.*
McKusick et al., 2018, #601777, OMIM, CORD6, p. 1-6.*
Boye et al., IND-Enabling Studies En Route to a Gene Therapy for GUCY2D Leber Congenital Amaurosis (LCA1). Abstract 433, 20th Annual Meeting of the American-Society-of-Gene-and-Cell Therapy (ASGCT); Washington, DC, USA; May 10-13, 2017, Molecular Therapy, vol. 25, May 1, 2017 (May 1, 2017), pp. 1-363, XP055466872, ISSN: 1525-0016, DOI:10.1016/j.ymthe.2017.04.025.
Boye et al., Efficient In Vivo Gene Editing of Inehrited Retinal Disease Genes in Mice and Non-Human Primates. Abstract 764, 20th Annual Meeting of the American-Society-of-Gene-and-Cell Therapy (ASGCT); Washington, DC, USA; May 10-13, 2017, Molecular Therapy, vol. 25, May 1, 2017 (May 1, 2017), pp. 1-363, XP055466872, ISSN: 1525-0016, DOI:10.1016/j.ymthe.2017.04.025.
McCullough et al., Somatic Gene Editing of GUCY2D by AAV-CRISPR/Cas9 Alters Retinal Structure and Function in Mouse and Macaque. Hum Gene Ther. May 2019;30(5):571-589. doi: 10.1089/hum.2018.193. Epub Dec. 20, 2018.

(Continued)

*Primary Examiner* — Shin Lin Chen
(74) *Attorney, Agent, or Firm* — Wolf, Greenfield & Sacks, P.C.

(57) ABSTRACT

Provided herein are methods and compositions for treating an eye disorder, for example cone-rod dystrophy type 6 (CORD6). In certain aspects, a therapeutically effective amount of a composition comprising nucleic acids is administered to a subject to treat an autosomal dominant disorder or condition, such as a condition associated with a dominant mutation in a guanylate cyclase 2D (GUCY2D) gene, such as knocking out a dominant mutant form of the gene in the subject. Further provided herein are recombinant AAV particles that comprise one or more recombinant AAV genomes comprising nucleic acids that encode a guide RNA that targets a GUCY2D gene and/or an RNA-guided endonuclease.

15 Claims, 30 Drawing Sheets
Specification includes a Sequence Listing.

(56) References Cited

OTHER PUBLICATIONS

International Search Report and Written Opinion dated Dec. 21, 2018 in connection with Application No. PCT/US2018/048405.
International Preliminary Report on Patentability dated Apr. 2, 2020 in connection with Application No. PCT/US2018/048405.
Payne et al., Clustering and frequency of mutations in the retinal guanylate cyclase (GUCY2D) gene in patients with dominant cone-rod dystrophies. J Med Genet. Sep. 2001;38(9):611-4. doi: 10.1136/jmg.38.9.611.

* cited by examiner

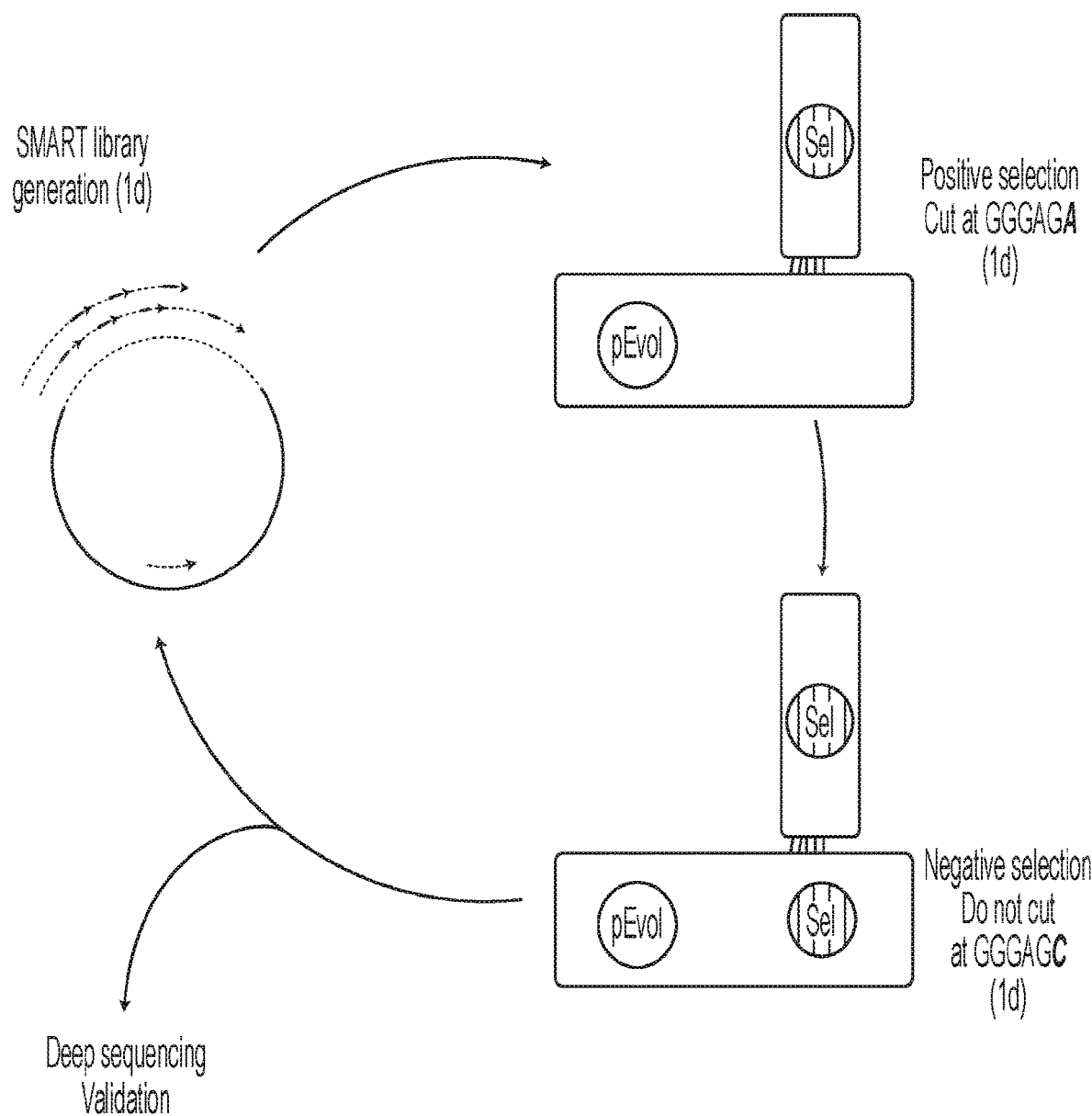
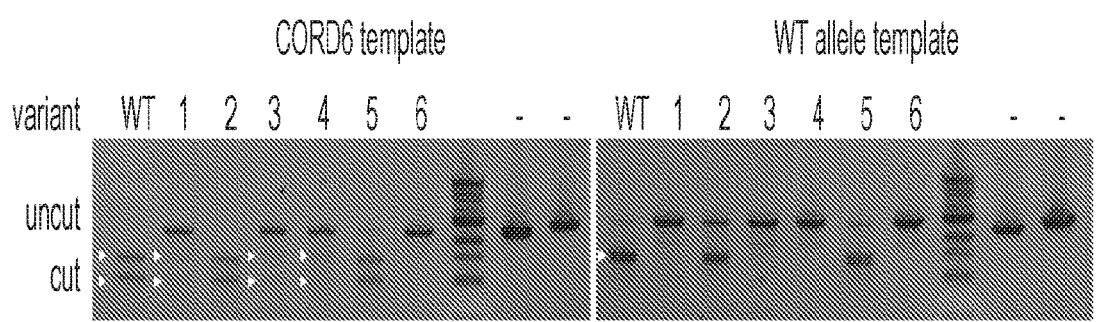
FIG. 10

28.7% indels

| SEQ ID NO | | Sequence | # of Reads |
|---|---|---|---|
| 17 | WT | GGTGACCCCGCTGCAGATGCTCTCTACGTCCTC | 48 |
| 18 | +1 | GGTGACCCCGCTGGCAGATGCTCTCTACGTCCTC | 3 |
| 19 | -4 | GGTGACCCCCG----AGATGCTCTCTACGTCCTC | 1 |
| 20 | +1 | GGTGACCCCGCTAGCAGATGCTCTCTACGTCCTC | 3 |
| 21 | -2 | GGTGACCCCGCT--AGATGCTCTCTACGTCCTC | 4 |
| 22 | -4 | GGTGACCCCC----CAGATGCTCTCTACGTCCTC | 1 |
| 23 | -4 | GGTGACCCCGCT-----ATGCTCTCTACGTCCTC | 3 |
| 24 | +1 | GGTGACCCCGCTCGCAGATGCTCTCTACGTCCTC | 2 |
| 25 | -2 | GGTGACCCCCG--GCAGATGCTCTCTACGTCCTC | 1 |
| 26 | -4 | GGTGACCCC----GCAGATGCTCTCTACGTCCTC | 1 |
| 27 | -5 | GGTGACCC-----GCAGATGCTCTCTACGTCCTC | 1 |
| 28 | +2 | GGTGACCCCGCTCAGCAGATGCTCTCTACGTCCTC | 1 |
| 29 | -8 | GGTGACCCCGCT--------TCTCTACGTCCTC | 1 |
| 30 | +2 | GGTGACCCCGCTGGGCAGATGCTCTCTACGTCCTC | 1 |
| 31 | -5 | GGTGACCCCGCT-----TGCTCTCTACGTCCTC | 1 |
| 32 | -1 | GGTGACCCCGC-GCAGATGCTCTCTACGTCCTC | 1 |

16.1% AAV vector insertion at cut site

| Sequence | # of Reads |
|---|---|
| AAV vector insertion - 411bp of Cas9 starting at R ITR | 2 |
| AAV vector insertion - 48bp of flag | 1 |
| AAV vector insertion - 51bp of ITR | 1 |
| AAV vector insertion - 55bp of ITR | 1 |
| AAV vector insertion - 126bp of Cas9 | 1 |
| AAV vector insertion - 123bp of tracr | 1 |
| AAV vector insertion - >550bp GRK-SV40SD/SA starting at L ITR | 1 |
| AAV vector insertion - >200bp GRK-SV40SD/SA | 1 |
| AAV vector insertion - >200bp Cas9 | 1 |
| AAV vector insertion - >200bp Cas9 | 1 |
| AAV vector insertion - >200bp Cas9 | 1 |
| AAV vector insertion - >550bp Cas9 starting at R ITR | 1 |
| AAV vector insertion - >200bp Cas9, flag | 1 |

FIG. 16

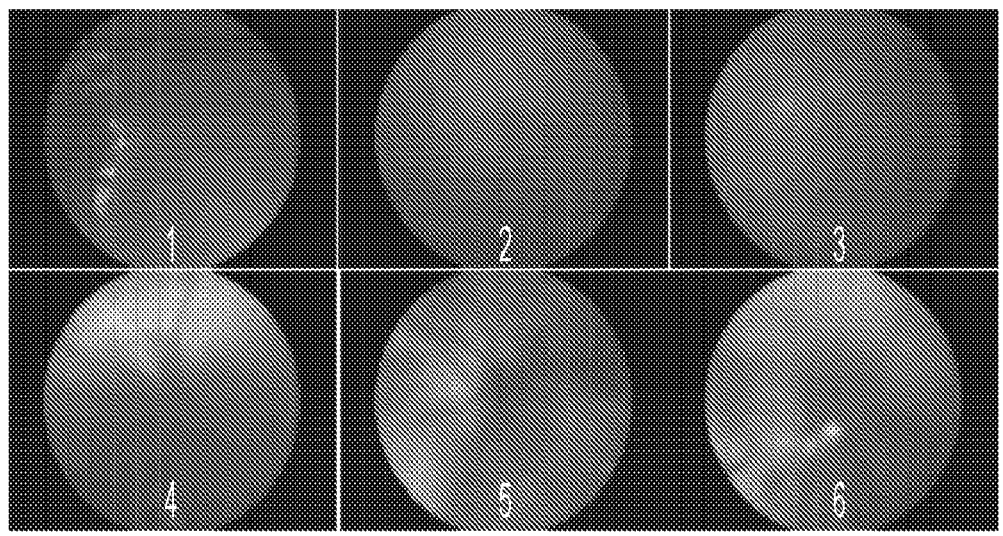
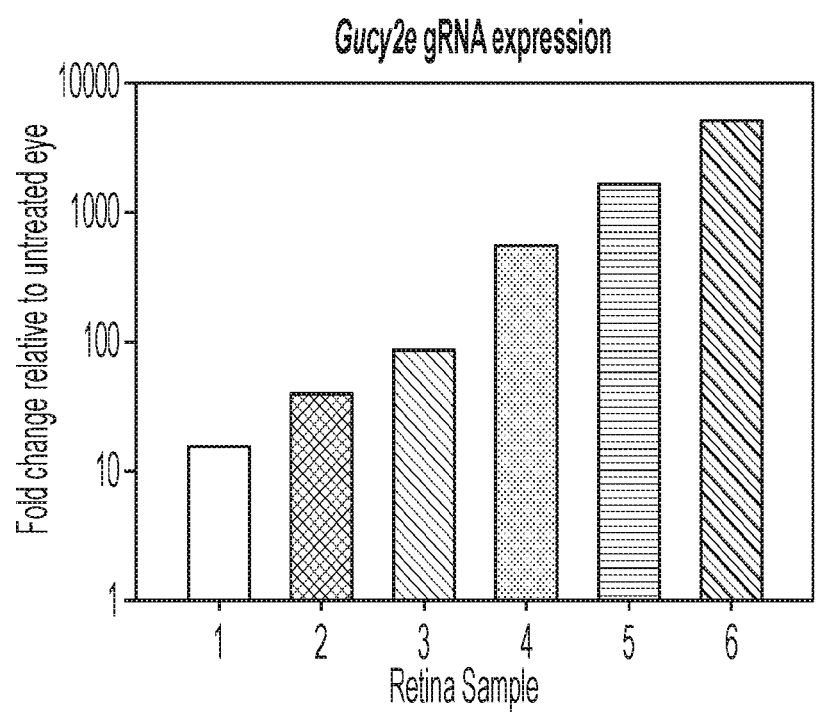
FIG. 22

28% indels

| SEQ ID NO: | | Sequence | # of Reads |
|---|---|---|---|
| 43 | WT | CGGTGACCCCCGCTGCAGATGCTCTCTACGTCCTCCTTA | 57 |
| 44 | -4 | CGGTGACCCCCGCT----ATGCTCTCTACGTCCTCCTTA | 4 |
| 45 | -1 | CGGTGACCCCCGC-GCAGATGCTCTCTACGTCCTCCTTA | 1 |
| 46 | -9 | CGGTG---------GCAGATGCTCTCTACGTCCTCCTTA | 1 |
| 47 | -2 | CGGTGACCCCCGCT--AGATGCTCTCTACGTCCTCCTTA | 2 |
| 48 | -13 | CGGTGACCCCCGCT-------------ACGTCCTCCTTA | 1 |
| 49 | -57 | --------------GCAGATGCTCTCTACGTCCTCCTTA | 1 |
| 50 | -3 | CGGTGACCCCCGC---AGATGCTCTCTACGTCCTCCTTA | 1 |
| 51 | -5 +1 | CGGTGACCCCCGCT----CTGCTCTCTACGTCCTCCTTA | 1 |
| 52 | +1 | CGGTGACCCCCGCTAGCAGATGCTCTCTACGTCCTCCTTA | 3 |
| 53 | -4 +4 | CGGTGACCCCCGCTG---ATGCTCTCTACGTCCTCCTTA | 2 |
| 54 | -5 | CGGTGACCCC-C-GC---TGCTCTCTACGTCCTCCTTA | 1 |
| 55 | -26 | ------------CTGCAGATGCTCTCTACGTCCTCCTTA | 1 |
| 56 | -1 | CGGTGACCCCCGCT-CAGATGCTCTCTACGTCCTCCTTA | 1 |
| 57 | +3 | CGGTGACCCCCGCTTTCGCAGATGCTCTCTACGTCCTCCTTA | 1 |
| 58 | +1 | CGGTGACCCCCGCTGGCAGATGCTCTCTACGTCCTCCTTA | 2 |
| 59 | +1 | CGGTGACCCCCGCTTGCAGATGCTCTCTACGTCCTCCTTA | 1 |
| 60 | -7 | CGGTGACCCCCGCT--------CTCTCTACGTCCTCCTTA | 1 |
| 61 | -14 +1 | GGGT-------------CTGCTCTCTACGTCCTCCTTA | 1 |
| 62 | +4 | CGGTGACCCCCGCTGTGTGCAGATGCTCTCTACGTCCTCCTTA | 1 |
| 63 | -6 | CGGTGACCCCCG-------ATGCTCTCTACGTCCTCCTTA | 1 |

4% AAV vector insertion at cut site

| Sequence | # of Reads |
|---|---|
| AAV vector insertion - 47bp of ITR | 1 |
| AAV vector insertion - 51bp of ITR | 1 |
| AAV vector insertion - 51bp of ITR | 1 |
| AAV vector insertion - 24bp of ITR | 1 |

FIG. 25

| GR114QB | SEQ ID NO | | Sequence | # of reads | % Editing |
|---|---|---|---|---|---|
| | 64 | WT | CTCTCCACTCTTTGGCACCATCTATGACGCGGTCTTCTTGCTGG | 77 | 12.5 |
| | 65 | -7 | CTCTCCACTCTTTGG-------TATGACGCGGTCTTCTTGCTGG | 1 | |
| | 66 | -2 | CTCTCCACTCTTT--CACCATCTATGACGCGGTCTTCTTGCTGG | 4 | |
| | 67 | -6 | CTCTCCACTCTTTGGC------TATGACGCGGTCTTCTTGCTGG | 1 | |
| | 68 | -6 | CTCTCCACT------CACCATCTATGACGCGGTCTTCTTGCTGG | 1 | |
| | 69 | -1 | CTCTCCACTCTTTGG-ACCATCTATGACGCGGTCTTCTTGCTGG | 1 | |
| | 70 | -3 | CTCTCCACTCTTTGGCA---TCTATGACGCGGTCTTCTTGCTGG | 1 | |
| | | 57 | AAV vector insertion - 57bp of ITR | 2 | |

| JR40D | SEQ ID NO | | Sequence | # of reads | % Editing |
|---|---|---|---|---|---|
| | 71 | WT | CTCTCCACTCTTTGGCACCATCTATGACGCGGTCTTCTTGCTGG | 83 | 6.74157303 |
| | 72 | -2 | CTCTCCACTCTTT--CACCATCTATGACGCGGTCTTCTTGCTGG | 1 | |
| | 73 | -2+1 | CTCTCCACTCTTTT-CACCATCTATGACGCGGTCTTCTTGCTGG | 1 | |
| | 74 | -7 | CTCTCCACTCTTTGG-------TATGACGCGGTCTTCTTGCTGG | 1 | |
| | 75 | +1 | CTCTCCACTCTTTGGACACCATCTATGACGCGGTCTTCTTGCTGG | 1 | |
| | | +>350 | AAV vector insertion - >350bp of ITR and GRK1 promoter | 1 | |
| | | +165 | AAV vector insertion - 165bp of Cas9 | 1 | |

| SA65E | SEQ ID NO | | Sequence | # of reads | % Editing |
|---|---|---|---|---|---|
| | 76 | WT | CTCTCCACTCTTTGGCACCATCTATGACGCGGTCTTCTTGCTGG | 71 | 20.2247191 |
| | 77 | -1 | CTCTCCACTCTTT-GCACCATCTATGACGCGGTCTTCTTGCTGG | 3 | |
| | 78 | -10 | CTCTCCACTCTTTGG----------GACGCGGTCTTCTTGCTGG | 3 | |
| | 79 | -1 | CTCTCCACTCTTTGG-ACCATCTATGACGCGGTCTTCTTGCTGG | 2 | |
| | 80 | -8 | CTCTCCACTCTTTGG---------ATGACGCGGTCTTCTTGCTGG | 1 | |
| | 81 | +1 | CTCTCCACTCTTTGGCCACCATCTATGACGCGGTCTTCTTGCTGG | 6 | |
| | 82 | -3 | CTCTCCACTCTTTGG----CATCTATGACGCGGTCTTCTTGCTGG | 1 | |
| | | -10+69 | 10bp deletion and AAV vector insertion - 69bp of Cas9 | 2 | |

FIG. 26

SEQUENCE LISTING

```
<160> NUMBER OF SEQ ID NOS: 82

<210> SEQ ID NO 1
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 1
agtactctag taacctggag gatctgatcc gggagagcac ggaggagc                48

<210> SEQ ID NO 2
<211> LENGTH: 48
<212> TYPE: DNA
<213> ORGANISM: Mus musculus

<400> SEQUENCE: 2
agtactctag taacctggag gatctgatcc gagaacgcac agaggagc                48

<210> SEQ ID NO 3
<211> LENGTH: 48
<212> TYPE: DNA
<213> ORGANISM: Homo sapiens

<400> SEQUENCE: 3
agtactctag taacctggag gatctgatcc gggagcgcac ggaggagc                48

<210> SEQ ID NO 4
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 4

Gly Thr Ile Tyr Asp Ala Val
1               5

<210> SEQ ID NO 5
<211> LENGTH: 22
```

```
<212> TYPE: DNA
<213> ORGANISM: Artificial Sequence
<220> FEATURE:
<223> OTHER INFORMATION: Synthetic Polynucleotide

<400> SEQUENCE: 5
tggcaccatc tatgacgcgg tc                                              22

<210> SEQ ID NO 6
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 6
tggtaccatt tacgatgccg tg                                              22

<210> SEQ ID NO 7
<211> LENGTH: 17671
<212> TYPE: DNA
<213> ORGANISM: Homo sapiens

<400> SEQUENCE: 7
caaaaggggg accggccctg tgacccctca ccggggggccg tgggcccgag ccccccggact      60 tccctgtaaa tgtcagaggc ccctccgctg ggatagggtc ggtctgaggg cgcaggcgag     120
tccctgctga ccccctgacgc ctccgacggg gggagggggca ggccgggtgg gagcgggaag    180
ccggggcggc agaagggggc ttcggggcgg tgtccttggc cccagttagt cttcccagcc     240
tccggagggg gcggtagcag cagaatcatc ccatggggtta ctcgggcttg gagaaactcg    300
gggttacggg gagaaccccta ggggaggccg gggtctcagt cgctcagcct gctccgtctg    360
tgttcgcaga agccggcaat gaccgcctgc gcccgccgag cgggtgggct tccggacccc    420
gggctctgcg gtcccgcgtg gtgggctccg tccctgcccc gcctccccg ggccctgccc    480 cggctcccgc tcctgctgct cctgcttctg ctgcagcccc ccgccctctc cgccgtgttc    540
acggtggggg tcctgggccc ctgggcttgc gacccccatct tctctcgggc tcgcccggac    600
ctggccgccc gcctggccgc cgcccgcctg aaccgcgacc ccggcctggc aggcggtccc    660
cgcttcgagg tagcgctgct gcccgagcct tgccggacgc cgggctcgct ggggggccgtg    720 tcctccgcgc tggcccgcgt gtcgggcctc gtgggtccgg tgaaccctgc ggcctgccgg    780
ccagccgagc tgctcgccga agaagccggg atcgcgctgg tgccctgggg ctgccccctgg   840 acgcaggcgg agggcaccac ggcccctgcc gtgacccccg ccgcggatgc cctctacgcc    900
ctgcttcgcg cattcggctg ggcgcgcgtg gccctggtca ccgccccccca ggacctgtgg    960 gtggaggcgg gacgctcact gtccacggca ctcagggccc ggggcctgcc tgtcgcctcc   1020
gtgacttcca tggagcccctt ggacctgtct ggagcccggg aggccctgag gaaggttcgg   1080
gacgggccca gggtcacagg taggctccct tgcaggtgc gaggaggtcg gctggtcctg   1140
ccggcagccg gacggcgccg cgagccaagc ctctgtccgc agcagtgatc atggtgatgc   1200
actcggtgct gctgggtggc gaggagcagc gctacctcct ggaggccgca gaggagctgg   1260
gcctgaccga tggctccctg gtcttcctgc ccttcgacac gatccactac gccttgtccc   1320
caggcccgga ggccttggcc gcactcgcca acagctccca gcttcgcagg gcccacgatg   1380
ccgtgctcac cctcacgcgc cactgtccct ctgaaggcag cgtgctggac agcctgcgca   1440
gggctcaaga gcgccgcgag ctgcccctctg acctcaatct gcagcaggta gacggtcccg   1500
```

-continued

```
ggaggaggga agaaggcaag ggagaggga gaggacagcc aaagcaggga gaggaggatg    1560
cagccaatgg agaaagaacc actggcagct ctagctgttt ggagtttcct gggtaatgta    1620
gaggctctgg ccccacttgg ggtctcttag tgtacgagga ttgcctctag agagtaggca    1680
attcgacctc tcaagtccaa catcaagcag taaactctaa tgaactgtaa actgcaaaac    1740
cttttgcaat tggcttcaaa gtaaacccgt ttccaccacc acatactccc agctgtctaa    1800
aataaatact tggtgttctt gaaagcagga aggagggagg atgccaatcc aaccttcatc    1860
cctagttcag aggtatttcc tctggggcct catctggtgg tcttagcttt tcaagggcct    1920
agacaccttg caagaagcag aaagttccct gggtggattc aggggcaatc ctaaccagat    1980
ccatagtgta tttccaacat ccagctaata cctagggatc cccaagtccc cagaatccca    2040
gttcagatca tctaacttta ctcccgccac aaagggggac tagaaaccac tatgagaagg    2100
gaatttagat gtcaacgggc agtgaattaa ccaccacaaa ggtccaactc acaggcggct    2160
gcatgagaga agggtcgtag gggttgcaat ttcccatcga tgcccctaga ttcttccaag    2220
aggattggag gtgtccaatg gagggggag gggtgcagtg atgggaatag tcagaagaga    2280
atacaagata ggaatcataa tgagatggga tggaggagg gtcggtcagt ggagagaggg    2340
aggttgagaa agtagagaga gaaaagccct tcagctctca gtaagtacca cagcagtcct    2400
ctccactgcc caaactgcgc aagcctctga gcgtgtgagt caccctttgat tccttgaatt    2460
cttcgccccc acttccaggc atcaagccct gttactgtta cttcctaaag atcattcgaa    2520
ttcatccgct ttctccatct ttactgtcac tgccctgatt caggccacag caccccagc    2580
ccaaatccca aaacataatc tctcagatgg tctctgcttc aacactcacc tgcccaacac    2640
cttctccag atcaagcttc agaaatctga cagatctcac cctgtcatgc ccctgttcaa    2700
agcctcacag tggcttctgt tgccctggat agatgcaggc ctctccacat ggcttaccag    2760
gtcacctgtc tttctctctc ttccacctcc catgaacttc agccagacca agctactctg    2820
ggttcttgga atgtgtcctt ctcttttgcc tctgagcttc tgagtgtgct gtttcctctc    2880
tcttgtccct gcctcccctg gataattctg actcatcccc tgaaggatgg tcacttctaa    2940
cagctccttc tctgtccaca gcctagggtg gggacaccca ttcctgtctc tgcagctccc    3000
tcagtttccc ctacttttac tcattgcact gcctgaacac ccctgtctct ttggcaagaa    3060
gaaaggttcc ttgagacggg gtctgtcttg tacactgata catctttagt gctctgcaca    3120
gtgcctggct ctctgagaga tggcaactgg gaataataga gaagcctgat aagatcgggt    3180
ggtaacaata gagaaggttt tttgtttgtt ttttgtttag ttttttttgtt tgtttgtttg    3240
ttttttaag gaacaacaga aaatagaagc caaccaaaag ataggtgaga aggcttttag    3300
gtgaatggta ggtgatgagg ttaaaactat atgctgggca accaacagga agaagagagg    3360
acctacaggt gatggagaat tagaatcaac caatggtcag agaggaggct gagtcctgaa    3420
aagaggaacc agttagtggg gagagcaggt gtgacagcca ataggagagg gaggaagaga    3480
gagccagtgg ggagggagga agagagagcc aatgggggagg gaggaagaga gccaatgggg    3540
agggaggaag agatagccaa tggggaggga tcctgggaac aactaactgg aaggtggcaa    3600
cagtggatac cctgggcttg acaggcagtg aaagaatctg gtctgtctgt gggctgtgac    3660
cccgacctct gagcccctac tctccttctc caggtctccc cactctttgg caccatctat    3720
gacgcggtct tcttgctggc aaggggcgtg gcagaagcgc gggctgccgc aggtggcaga    3780
tgggtgtccg gagcagctgt ggcccgccac atccgggatg cgcaggtccc tggcttctgc    3840
ggggacctag gaggagacga ggagccccca ttcgtgctgc tagacacgga cgcggcggga    3900
```

```
gaccggcttt tgccacata catgctggat cctgcccggg gctccttcct ctccgccggt    3960
acccggatgc acttcccgcg tgggggatca gcacccggac ctgaccccct cgtgctggttc   4020
gatccaaaca acatctgcgg tggaggtgag ggcgagcacc ccagtcccca ctgagacaat    4080
cgccatggac catccacaaa gtgatgaaag agagtggact cctatcctgt aatccgtctt    4140
cgatgccctt ctaggccctc tcccagcctc tggcttgcac aggacccctc tcttgctgag    4200
ctccaaagcc ctcttggaaa ttttctatca ttcccagcct ctccccttg aggaactatg     4260
acctacccct agagcctctc tgggccccca tcccctttc ctgggggggc agcatgtgg      4320
catgcctccc tagagaagag gcctcccctg gcatcgctcc tcagtatacc tcctgtcact    4380
gtcccttcag gactggagcc gggcctcgtc tttcttggct tcctcctggt ggttgggatg    4440
gggctggctg gggccttcct ggcccattat gtgaggtgag tagtggaatg aggtaagtag    4500
gaagtgagct tgtgccagaa atggaagtct gcagcaaaaa cagcaggctg ggttcactca    4560
ggagtagagg aggagatttt tcttggggtg agggtgttct ggtgggctgg tagagtccca    4620
ggggatgtgt gctttgggga tggctgccct ccaggacccc tcccctgagc caacgttatc    4680
cctccccgc atcccctgct ggtctcttct gacggaactt ggtgcccttg gtggaggtga     4740
cctctttctc caccaggcac cggctacttc acatgcaaat ggtctccggc cccaacaaga    4800
tcatcctgac cgtggacgac atcaccttc tccacccaca tggggcacc tctcgaaagg      4860
tgggggaggc agagaggcag gagccagttg tcttctttcc gtaaatttgg ttccttccct    4920
gggccagtcc cgaccccagc tccctacttg ggaagcctga tttctacccc agttctgtcc    4980
cacgtctgaa gtctagggat cagcacccttc atctgtgcaa tgagggtaac agtacctgtc    5040
ctgactactt tcctggcggg gaggtgaagc tccaacaaga aaatgaatgt ttgctttgta    5100
aactgtaaag cgtgcacttg gggagtaatg tcattatcac cttccctcat tgagattcct    5160
tcgcctccca tctttaaatc cccaaaactc agcctgacct caaccaggaa ctctgacacc    5220
agaatatatt ttgacctctt gcattgacct ctacctgcta ggtggcccag gggagtcgat    5280
caagtctggg tgcccgcagc atgtcagaca ttcgcagcgg ccccagccaa cacttggaca    5340
gccccaacat tggtgtctat gaggtgagcc tgaccccagc cagacagaga gacagtgggg    5400
gaagaatgct caggccctgg gcagagggga ggcgcactct caggaggaca tgtagtcatg    5460
tcaaatcctg caggctccag gagatggggg atgggagccc agacaggatc tagggaaagg    5520
tcatggatcc ctcaaaggga agcacctagg aatcttccct ccccaaggat ttttctctag    5580
ccactatctg ggtaagggct cctcaaaagc taaccacagt gacccagaga ctggaggctg    5640
gagctgccag ggagcatgct gggaccagca ggtaacatgg tgtggccact gagaccatct    5700
ccggcctggt cagagcctct ggccctgccc tcagcatttt ccacccaatt cagaccagac    5760
tcaggaatag caacccctag aggggggaaaa gaaagtcaca aaaaagtatt aggacattaa    5820
ctttggggct ggtaaatctg aatgcggtca agtggagggg agatgatgag aacagattga    5880
gagagagctg agagtgctga gcaaatcaag agagtagaaa tttagagctc ctgggcttca    5940
ggtcatggga aggaatgcag aggctcctat catgtcacct agagatcatc atggccaatt    6000
ctcagaggag gcactattgt catttggggc agattgtcct aaattgtatg ggactactct    6060
gtgccttgaa gaatatttag tgtttcttgt ctctggccct gtccactaat gcagctccta    6120
gttttttgtga cagttaaaac tttccccaca tttatttcca aatgctcctt agggggtcagt   6180
actaaacccc aattcccttc taaattccct tctagtccaa atcccttata aacaagacag    6240
```

-continued

```
ggccacctgc ataattagcg agatccaggg caagatagaa atgaggggct cctcgttcat    6300
tcatgatgat ggcaggaggt cattgaacca agcttgggcc cttcggagca cgaggccctg    6360
tgtgactgca caggtcccat gcctgtgaac cggccctgcc aacagttgag gatgaggtcc    6420
agcatcagga ggggagctgt ctatagttca gttagttttc aataaagcct gatctaccca    6480
gattttttac tcccagaaca tgttctctca tggcagtgga tggtaatgag ggttgtgatg    6540
tcgatgacac ttgtggttgt attaatgcac ttaataggac tattggtggg cacagctggg    6600
ttggtgagga cagccatcca tggcttcaga atctctgtca tccaggggtg ggccctctcc    6660
cagatggctg tgaagtggat gggcatacat caaaccccTt ggttcaatgc attttgtcac    6720
atggaagatg cattctggga cagtgagcca atggaaatga gggggagggg ttctagggct    6780
ccccatcgtg ggattttaag agactgagtt ccctacccCc atcctctttg ctgcagggag    6840
acagggtttg gctgaagaaa ttcccagggg atcagcacat agctatccgc ccagcaacca    6900
agacggcctt ctccaaggtg agacttgggc ctgtgatggg gcctaggtgg ccatcggttt    6960
ctccctcctt gccttctctt tgcagctggg tacagaggta ggtctcagtt aagtgtcccc    7020
tctggctgag tgtggtggct catacgtgta atcctggcac tttgagaggc agatgtgagg    7080
gaggatcacc tgaggccagg agttcaagac cagcctgggc aacataaaga aaccctatct    7140
ctccaaaaat tttaaaatta gctgggtgtg gcgttacatg cctgtagtcc cagctactct    7200
tcagagggtg aggagggagg attatttgag cctgggagtt ggaggttacc gtgggctgtg    7260
atcatactac tgcactccag cctgggtgac agagcaagac cctgtcaaaa ttaagaaaga    7320 aaaaaaaaa catgtttcct ccaccctgga gtaggctttc attattctct gccacaccac    7380
tagttctttc ctttgatctt gttgcaatgt gcaattgtat gttcatctgt ctgcctgctt    7440
gtttctgcct ctccgctgg actgtaagct gagtgagggc ctcctcactc ccctccattg    7500
taatcaagca cccaacacag tgtctggaac attagagaga cccagtgaat gtttgttgat    7560
ctaatgatag aaaataaaaa atgagtttcc ggttctgtca ggccacttgt gcagaatagc    7620
cctggacatt ctgaatgaag tgcaaagttg gcaaggaggc tgtaaatggc ttattctggt    7680
ccttacaacc ttaatgtctc cctttatctc catgccatgc agcctgggcc tggccttctt    7740
ccctgattcc tctacaggag ctcttggtca cagatgcagt gacttaagtg gactatgtgt    7800
atggggatta tgaactcga tcaccattta ataccaggtg tttaaaatga aaagtatctg    7860
ggcgcggtgg ctcacacctg tgatcccagc actttgggag gccgaggcgg gcggatcacg    7920
aggtcaggag atcgagacca tcctggctaa cacggtgaaa ccccgtctct actaaaaata    7980
caaaaaaaat tagccgggtg tggtggcggg cgcctgtagt cccagctact gtgggaggct    8040
gaggcagaag aatggcgtga acccgggagg cggagcttgc agtaagccga gatcgcggca    8100
ctgcacttca gcctgggcga cagagcaaga ttccgtctca aaaaaaaaa aaaaaagga    8160 aaggaaagaa aagtatcccc ttattgggca tgtggaggga aaagctagaa agggcaccag    8220
tcagccagct aagccacctt tttttctagc atgcccgat tgtgagggca ctgtcctgca    8280
gagcagtcag tcctgtcttc cctaactgag ggagggtggg agtctcagac ccgactgaca    8340
caatgacgta acgccaagca gagcagcccc cggccaggtt gcaggcacac gccatttctg    8400
gtgtcctttg aaagtggcac agcttcaggc cgggcaccgt ggctcacgcc tgtaatccca    8460
gcactttggg aggctgaggt ggatggacca cctgaggtca ggagttcgag accagactgg    8520
ccaacatagc aaaaccccat ctctactaaa aatacaaaaa ttagccaggc atgatggcac    8580
acacctgtaa tcccagctat cgggaggct gagacgggag aatcgcttga gctcaggatg    8640
```

```
cggaggttgc agtgacccga gattgcacga ctgcaatcca gcctgggtga cagagtaaga    8700
atctgtctaa aaaaaaaata cataaacaaa agaaaagaaa gaaagtggca ccgctcctcc    8760
ctggctctcc cagcaaaggc tgttaaatca ggagaggatg gtggttccag gagcttctcc    8820
ttcatgagct gcttcccctta agacccaggc agttcagagt tttatggctg gggccaggtg    8880
tggtggctca ggcctataat cccagcactt tgggaggctg aggtgggagg atcatttgaa    8940
gccaggagtt caagaccagc ctgggcaaca tagcaaggct cccatctcta cagaaaaaaa    9000
attttaaatg ttatctaggc atggtggcac aagcctgtag tcccagctat tcaggaggct    9060
gaggtaggag gatcacttga accaaggaat gaaaggtagc agtgatttat gatcatgccg    9120
ctgcactcca gtctgggcaa cagagtgaga cctcgtgtct aaaaaaaaag gcttatgatc    9180
aataaatccg aacctgcctg gtcctgatc accaatgcaa agttgtcttt tcattcacag     9240
cattaggcta aaccatactc agtatccaaa cagtggcctt tgactatatt gttttttcca    9300
aaaataggac tatgtgtaga agagagcccc cgtacatacc ttatcaacca tttcatccac    9360
catttgtaaa aatctcatct tctgggtctg gatactcaaa aacagatctt gattaacagc    9420
cccttcccca cattgccctg gcagaaaat gcaagtcaac tctccccctc tcagctccag     9480
gagctccggc atgagaacgt ggccctctac ctggggcttt tcctggctcg gggagcagaa    9540
ggccctgcgg ccctctggga gggcaacctg gctgtggtct cagagcactg cacgcggggc    9600
tctcttcagg acctcctcgc tcagagagaa ataaagctgg actggatgtt caagtcctcc    9660
ctcctgctgg accttatcaa ggtgtgtgtc tgggggtggt ggggtgacgt cctgggggca    9720
gggatgggga gcaagggaac caagcaggct gaggctgcct cttaccctac ccattccaag    9780
ggaataaggt atctgcacca tcgaggcgtg gctcatgggc ggctgaagtc acggaactgc    9840
atagtggatg gcagattcgt actcaagatc actgaccacg gccacgggag actgctggaa    9900
gcacagaagg tgctaccgga gcctcccaga gcggagggta agagtcccct gtgcagacga    9960
ggatccaccg ggatccccat tatttcaagg gcttctcccc cgcttcctcc ctacctctgc    10020
cctcgcactc tcttcatccc acatccacca gacacaattc ctgctacaga aaagatcttg    10080
tggcctctga gagggtgggc tctgtgactt cggagacggg gctgctgggg gcgggacttg    10140
tacctgagct gcctgcagca gggttttgctc tgattacaag tttgcctgag ggtggggctt    10200
gtgcccaaga gacggagcct tccctgggca ccacctttc tgaagggcaa ggcctatttg     10260
ccaggctttc tctgagatgg ctcctagaga tagttgcagg gctggtctca ggttgcaggg    10320
tctcagaccg gtctcaggct gcaggggttgg tggtgtctgg gtgccaacct gggctttctg   10380
gtgagggtgg gagtctttcc ccagcggcgc ctcagcccct tccccatccc cagaccagct    10440
gtggacagcc ccgagctgc ttagggaccc agccctggag cgccgggaa cgctggccgg      10500 cgacgtcttt agcttggcca tcatcatgca agaagtagtg tgccgcagtg cccctttatgc   10560 catgctggag ctcactcccg agggtaaggc tgccctgtgc gtggagttcg gcccacaggg    10620
gcaccctgca gttagaaaag agccagcctc actctttcct ctaaagcaaa gcccagtgat    10680
gaaactcaat tatacggagg ccccctttaaa gctggcatct gcaggtctgg gtgcagaaag    10740
ccgtgcatgg ccagggtggg gagcgtggtt cattaggtcc cagaccacaa cagcttcctc    10800
tttcttgatg ctggaaccaa actgtttcca caactgacag aacagactcc tctctgttct    10860
caggggtccc tggaggagc aggggagggg gagtgggtgc atcccttctg cacaggactc     10920
tgagcaaact acttgatcac ctatccctca cttgtcttac atacaatatg ttagtttctt    10980
```

```
tgcctatgtc acctcttact gacccccaga gttcgaggtc ctcttgttcc tcctagcaac   11040
ccccttccac actatactct ccctccacac acacacactg aacctctgat gtaaagaaac   11100
ccctgccagg caccccctcc cacatcttgg tcttcaacag tcaggccagg gtcagaggca   11160
gcctttgtgt tctgggggca ctcccctca ctgtcccctc atgcctccag aagtggtgca    11220
gagggtgcgg agcccccctc cactgtgtcg gcccttggtg tccatggacc aggcacctgt   11280
cgagtgtatc ctcctgatga agcagtgctg ggcagagcag ccggaacttc ggccctccat   11340
ggaccacacc ttcgacctgg tcaggggctg ggagtgggca aggactgggc tggcctctgg   11400
gatcccagat gcttgtcagc aacctgagac agctgcagac aggcaggctg gcaggacctc   11460
tggccttcca ggctacctcc taaggagtag cctgaagact cggagtttgg gggcagaatt   11520
ggaatggggg ctgtggaggc ttttggagtg ggagatagaa ttctgtctgg gtgggaggaa   11580
tattcaattc aattcaaata acactgattg agaaccaagt atgtgcttgg cctgctgtga   11640
cagaaagacc cttggcctgg gagcccaacg attgggctgg ctccagtgcc ctgtcaatta   11700
ctagctgaga tcaactgacc tctgggaacc ctcatttccc acgtgcctcc taatcgtgtc   11760
tgaaaacaca gtgcccagca ccccggggtg cttgatgaat agtagatgaa tggtggcagc   11820
ggggttgggg ttcagagtga acagcccat gagagggccc atgaggggg cataaagagg     11880 gcatggcaac ccaggtcttc agcagcttta ccagcttcct tctactgcta gttcaagaac   11940
atcaacaagg gccggaagac gaacatcatt gactcgatgc ttcggatgct ggagcagtac   12000
tctagtaacc tggaggatct gatccgggag cgcacggagg agctggagct ggaaaagcag   12060
aagacagacc ggctgcttac acagatgctg cctccgtggg tgccagtggg aagggggtggg  12120 ctgggagggc agctggagcc cagccaggta gagtggcccc caggtgacct cactgcctgc   12180
catccctagg tctgtggctg aggccttgaa gacggggaca ccagtggagc ccagtactt    12240 tgagcaagtg acactgtact ttagtgacat tgtgggcttc accaccatct ctgccatgag   12300
tgagcccatt gaggttgtgg acctgctcaa cgatctctac acactcttg atgccatcat    12360 tggttcccac gatgtctaca aggtgcagtg tgtaggggac aagccctcct gaccttcaat   12420
tcagcttcac cagcctccag cccagccctt cctgcgcagc cctagccta cctgcccaat    12480 caatcttctt tcccagacct cctgtccctt atttattcct ccagtcccca gctcagtcct   12540
tccactagca acctggttct gcactaaccc caggtgggcc cggtgacaag aggcaatcgc   12600
ttcgtgtact cggggggaat gctcaaaaga aaattcacac aactccttct tcccccaggt   12660
ggagacaata ggggacgcct atatggtggc ctcggggctg ccccagcgga atgggcagcg   12720
acacgcggca gagatcgcca acatgtcact ggacatcctc agtgccgtgg gcactttccg   12780
catgcgccat atgcctgagg ttcccgtgcg catccgcata ggcctgcact cgggtaactc   12840
ccgggtcttc ccaggctcca gcccatctcc ctctttaggg cctggcccca gatttcctgt   12900
agaggaggca actcatggag cggggagtgg ggcttacctt gaagaggatg cacttaacaa   12960
ggcttatttg ggggggctggt ggagataatg ggtgcgaaga tccccgagg ccctacctag    13020 gtgcagccca gggccggccc tgctagcccc gccgaccccc agcatctcca caggtccatg   13080
cgtggcaggc gtggtgggcc tcaccatgcc gcggtactgc ctgtttgggg acacggtcaa   13140
caccgcctcg cgcatggagt ccaccgggct gcgtgagtgt gacggggaca agacggggag   13200
gtgggagggg gacacgggag gtgagtcccg agctcacggc gtcccccacc gccacagctt   13260
accgcatcca cgtgaacttg agcactgtgg ggattctccg tgctctgac tcgggctacc    13320 aggtggagct gcgaggccgc acggagctga aggtgaggca gggccccaac ccctccggga  13380
```

```
ggccccgccc tgtcctgagg caccgcccat cccgggccgc ggctgcaaac ctcagctcac   13440
ccttctgacc tggtctccca gttccacgca gactcgagat cccccacccc tcaccccagt   13500
ccgcctaagt ccttccctct cccatgtctc cccagggcaa gggcgccgag gacactttct   13560
ggctagtggg cagacgcggc ttcaacaagc ccatccccaa accgcctgac ctgcaaccgg   13620
ggtgaggggc cggcctccgc ggcagggcga gggacgaggg acccctgcct cctgctctgt   13680
gtctgacccc ccgcgcgcga ggcagcgatg acgtgggccc tgccctccca cgccccattc   13740
cccttccctg aggccaccgc cccctccttg caggtccagc aaccacggca tcagcctgca   13800
ggagatccca cccgagcggc gacggaagct ggagaaggcg cggccgggcc agttctcttg   13860
agaagtgagg cccggccccg acaggtact gccccctcag cccaacccc agctgccgcg   13920 tcccctctgc tgcctgcaga acgtcccacc caagccaggt gtcccgatcc ctttctgact   13980
tagagagccc aggctggttc ctaaaccccg gggcttcccc tgggagggaa gcagccattg   14040
caggaatttt ggttcagtag atctggagtg gtttggaaat ccaggcttag gaaactccgt   14100
aatcggggcc ttctgtggcc cctcccctgg ccctatctca tccccagtgc ataaacctgg   14160
cttccgcaga agcctcacag gctgtgcact gcacaagaga caactctagg gggcagcagt   14220
caccagagaa caatgtgaaa gcagaagccg tgcccactcc cctcctgcaa gaaactgacc   14280
cgtgacccgc tccttcctag gtgaaccccc atgacccctt tcctcgactc ccctctgaga   14340
tacccctctt ttcttcagga ttgttctgga aggtccttt cctgaaagtt gctgctatag   14400
gtgactggaa gtctgtctaa tgctggtgga ctctgcccag ctctgcctca aaggattttg   14460
ggccttttac aagagctggt tgcaaaacca gccatgtgac cttgggaaag tgtcacgcat   14520
gctctgctgt gatcccttca gtggcaaaat ggggggtggc ctaagtggtt cccaaggccc   14580
ctgtgcacct gacagctggg tggcttgtgg ccctcacccc caggagccct gagtccagca   14640
ggggatgtga gggtcaggga ttctccgctt cccagtgtct ctcagggacc caggaaggag   14700
gatctgggat tgatgcccga ccccagagga agtggagttc tgttccacca gagcagggtt   14760
tgtcacatgg cctgagggg caagggctcc tgtttagcct caagcttcat tcctatctcc   14820
atctcccacc agtcagaaac tggctgcttc tcctgtgggt ataatcaggg aacttgccca   14880
agtgcagaga aaagcttgct tcaatgcttt gaggaaagga aattgtgcca caccttgact   14940
gaccagaaca tccaaagagc ggcattctct gtttaactag gagctgctga gcaagcagtt   15000
ggacagaaaa tcctctctgc ttagaatttt ttctttttt ttgagtctca ctttgtcacc   15060
caggctggag tgcagtgcag tgacacaatc tcgactcatt gcaacctcct cctctccaggt   15120 tcaagtgatt ctcctacctc agcctgccga gtagctggga ttacaggcac ccgccaccac   15180
gcccgggtaa tttttttgtg tgattttagt agagatgggg tttcagcatg ttgcccaggg   15240
tggtcttgaa ctgacatcaa gtgatctgcc caccttggcc tcccaaagtg ctgggattac   15300
aggtgtgaga caccgcgcct gacctttgca gcaattatca atgccctgtc ctggcaagtc   15360
cccagttgaa gttgcctttg tgaaactctg accttccaga gcctgggcct tggcacattt   15420
gactcttggt gtctgtcacc attgctacag accctggaag aagtttgcag caggctagga   15480
aaccacctag gctgccacca gaggtagtga gtgtccagtc cctggaggtg tgaaggcaga   15540
actggagaca tcattgacca gggatacgac agtgagaggg aattccggaa ctgaaccttc   15600
actacaccaa gtgtggttgg tgggccaggg tcggcactgc ctgtgagctc attagaaatg   15660
aaggatctca gggcccccacc ccagacctgc tgagtctgga tctgcatttt aacaagttcc   15720
```

| | |
|---|---|
| tacaaaatat tgacacgctc attaaagttt ctgaatcata gaactaaatc accctaagat | 15780 |
| ctttaaatct tagaatctct aagatctcat aaagccaggc tacaaactag ccaccaaatt | 15840 |
| tcttttgttt ggcctataga gtgttttgtt ttgagctaac atttaaaaat caacagcttc | 15900 |
| cacattttaa aaatgtatag cagatttccc ccttctcttg aaatcagaag ccccacatgg | 15960 |
| tgcttgtgtc accacttaac cacattctgc tgcagctaaa cagcaacagt cccctttatc | 16020 |
| cagatgtcgc cactcccac agactccgag acaccaagat tttttgaaca ttcctttata | 16080 |
| ttcctgcctg gtgcctgtag acattgagct taggactcct tagcaggtat taggattaca | 16140 |
| ggggctcctg gacgggactt tgccttcttt tttttttttt taaactgatt catgacttcc | 16200 |
| acaagcttag tggtattccc ctccttccta aaggtgaagg aagaatgtat caaacatcga | 16260 |
| gaatccagca cttgtaagtt ctggttaccg aaggtgatgt tgctacagag agcaatttag | 16320 |
| tgcaattta aaaacatttt aaattgaatt taaatacgat gaattaaaga ttaaaaacaa | 16380 |
| aacaaaaccc gggcatgcac acacacacat ttttaaaagt tatttacatt cttgaagatt | 16440 |
| ttccttaaga ttttctctgt acttaggtcc cagggattga agcgcagatt cacatctctg | 16500 |
| gccttggacc tgactgtgtg gatagagctc tcagcctcct gtctcttccc tcccgtaccc | 16560 |
| gaccctgcag cccttcccct tccttcctc tctcctgcc tgcaagggcc tggagtagtt | 16620 |
| aatggtgtgt gatttcggct gcctcaagga agagtccagg attaggtgca gagggattag | 16680 |
| ctgggacagg cttaggcagg gctcctcccg gaagcagagg cggatgagcc agagggcaga | 16740 |
| cccagtttaa ggtagaagtg gagtgggcag ggctgagcca gttccttccc accttcactc | 16800 |
| agcctccttc ccaggctggc ctcaagctca agtgaccaga tgtgatagaa gagccctgac | 16860 |
| ccctccccag ctagaagaac ttggggaacc cccaccccag agttcacaga tctagtggga | 16920 |
| gaagagaagg caaagatga agcctcagcc tcctctctgt gcctcagcct ctcctttctc | 16980 |
| tgttcctgcc tcccttctg ctctattctc ctgtctttgt gtccccacag tccccttcct | 17040 |
| gcctggcagt ctctgtctgc ctttctctgc agtttccacc atttctctgg aaatcttatt | 17100 |
| tcctggaccc agtcggttat ccagtctcag ggctctgctg actcaagtcc tccccaccct | 17160 |
| gttcctgtgg cctgggcaac tcccagcgca tgagagcacc ggggcctggc ttggtcactg | 17220 |
| ggcatccccc accttcagat gtgtttacac tacctctgcc agctggcctg cgccaggagc | 17280 |
| ccacacttgc ggttgtcctt gccttggaga tggctctgta gctggcagag cagtgatggc | 17340 |
| caaagcaggg acctctcata gctgctgctt caatcccacg gcagagactc tacagcgtgt | 17400 |
| cccgggctc acctggcgcc tttttttttt tttttttttt ttttgtgctt ctccttaggg | 17460 |
| tctgggccct gctccctgtc ccatctgcag tggacccag gcaccccct ttgaggaggt | 17520 |
| ggggtgaact gctccttggc agggatttgt gacactgcat tgctgggctg tgttcctcgg | 17580 |
| gctcttctgg accttgcacc gtggatacca ggccatgtgc catggtattt gggtcctggg | 17640 |
| agggtgggtg aaataaaggc atgctgtctt c | 17671 |

<210> SEQ ID NO 8
<211> LENGTH: 24707
<212> TYPE: DNA
<213> ORGANISM: Homo sapiens

<400> SEQUENCE: 8

| | |
|---|---|
| atacaagttc tccccacctt ggcactctca gtatcctgcc aagagtcctc cctgaccacc | 60 |
| agaagttcca cctcaccatc aagaaaggcc ctggtccagg atgtgcaagg tgtgatgaaa | 120 |
| tcacagggct ggggaaggtc agctcggggt cacaagaagc ctgatgggca ggaaagagca | 180 |

```
tgaaagcccc agccagcctc acatgtgcgg ctgggaggta ggtcctctta caaaaggctt    240 agtgggtgc tggtgctggt gctgctgcct gccttgtact ccccagctgt cggacctctg    300
cgatctctct ggggagatgg agagagggaa caggacaccc tccatcttgc ttcctctgcc    360
ccttcactgc tgtaaagtgt gtcctggact gtttggttcg tgttacacca tctccaaggc    420
aaacttgaga taaataataa ttgtagctaa agtttgagtg cttaagaggt ctaggcacct    480
tacatggact agctcattaa gtcctcacat gaaccctatg aggtagagct cttgttattc    540
ccacattata cttcggaaaa ttgaggtaca gagattataa tttgcctaag gatcaggcag    600
ctagtgagtg agagggctgg aattctattt attttttttt tgagactcgc tttgttgccc    660
aggctggagt gcagtggcac aatctcagct aagtgcaacc tccgcctcct gtgttcaaat    720
gattccccca cctcagcctc caagtggct gggattacag gcacctgcca ccacgcccgg    780 ctaattttt tgtatttta gtagagacgg ggtttcacca tgttgaccag gctggtcccg    840
aactcctgac ctcaagtgat tctcctgcct cggcctccca aagtgctggg attacaggcg    900
tgagccactg tgctcagcca tttttttttc tttttttttt ttttttactt ttttataaaa    960
tagagatgag gtctctcaat gttgcccagg ctggtcttga acttttgagc tcaagcaatc    1020
ctcccacttc aacctcccgc tgaattacag gtgtgagcca ccgggccctg cagggaactg    1080
gaatttgaac tggggtagct ggctccaggc tctcatgcta cccagtcaca tgaggaagct    1140
gaggcctacc cccggcttcc ctaaccactc ccttcaaagc ccctgtgctc ccccaaaggg    1200
aaacgtgctc tcctataggt tcagacaggt atgtgtgtga aaccacggtg taactgcccg    1260
agaggctgag agtaatgact atttgcactg tgcctttacc gttcccagca ctcatggcac    1320
cccaccacaa gctggtgaat tagatagcct tattatcccc attttgcaga tgaggcccct    1380
gaagctcaaa gaggctcagc cacttgccca aggtcgcctg acctgtaaga acagggtcag    1440
gcccagagct cagaccttca aacaccaaag ccaaggcaca ttggacagca ccacgtgccc    1500
ctgggggccc tcaccagcct tcacacccaa gtgctatttg catttcaata aggcacaagg    1560
ccttccccca gagtgaggag gctacaggtg gaatttctca ctgggcaagg ccatgtgcct    1620
atggccctgg aggatttgag aggacagggt gccttcctag aaaacctgta gtaatatcac    1680
agatgagatc ttcttgccct actcagaaag ccccactctt gagtcatgca cttcctcact    1740
ctaaaccccg gcataaggga caaacgcata ttagtatata tgtacatatt aatacatgtg    1800
tactgtgcat ctgaaaggcc tttgtgggt ccgcctgtgg ggatggggt tatgaaggga    1860 tatttctttt ttctgagaca aggtctcact ctgtcactta ggctggagtg cattggctga    1920
tctcagctcc ccgtaaccct ctcctcccctg taacctcctc ctccctgatt caagtgattc    1980
tcctgcctca gcctcccaag tagctgggat tacaggcgtg caccatcaca cccagctaat    2040
gttttgtatt tttagtagag acggggtttt gccacgttgc caaggctggt ctcaaactcc    2100
tgggctcaag tgatctgccc acctcagcct cccaatgtgc tgggattaca ggcgtgagcc    2160
atggtgccgg ctctttttc tttttttttt tttaatagag atggggtctc actatgttgg    2220
ccaggttgat cttgaactct tggcctcaag caatcctcct gccttggcct cccaaagtgc    2280
taggattata ggcatgagcc accacgctgg cccagtgagg ataattcta cctagattcc    2340 ttcttttggc tttagcttag aacccaagtg aaaataggat catgggattc ccaagggagg    2400
ggaggggctg gtgagaatct ctacttgtcc tgtaacttca tcactccctg tagaatggaa    2460
atgagggaag cagtagggga gatggggctt cttcctcaac cctctaaacc agggtttctc    2520
```

```
aaccttggcg cttttgacat tggacgctga tgattctttg ttgcgggggc tgtccattgt    2580
aggatacata gcagcatccc tgtctcctac ccgctggaag gcagtagcac ccaccccaca    2640
ctgtgtgaca acccaaaatg tctccaaaca tgcatgccaa atgtcctctg gaggaagaat    2700
cacccctggc tgagaaccaa tgatctaaag tcacatacac agtgtgcgca cacccagcac    2760
acttgacgag gagcatgtga gcaaagaata gccagttaaa agaaaccaga tgttaacctg    2820
gaaagtatgc agtcaggccc caccctcagc cagagctggc tctgctaggc cctggggag    2880 gtaatggggt gtcctcagcc ctctgaggtt agtcacttgg aggctggctt ggcccctaga    2940
aagggcaggg gagggctagt gctgcctgac tccctcttcc tcctcttcca cctcttcccc    3000
tagactgtct gtgtcccagt ttttgtgagg gcttcatccc tggatgttcc ggggaccctg    3060
gctgtcccct acccctgctg cccccagagt cctgtatgtt gcagcagcag cattctaaac    3120
acagccgagg tgtggaccca gggcaggtgg gcccaagcca gggcctgggc tagggcagaa    3180
agggaggaga gagtttgaat cctggttccc acactaacca gttgtgggac ttctgcaagt    3240
tacttacatg ctattctaca aactgtgaac tcagaaaaat gctttgatgc ctccgagcct    3300
cagtttcctt atctgaaaaa tggaggcaat gtctcaaatg gctcttagga gcttttgcag    3360
agctgagtgg ctaatgcctg acatttggca gatcctcaat cctgtgagta aagagtgcca    3420
cccttccatc tgtgggctgc tctcttcagt tccccagcca ttctaaaagc acctgcctct    3480
gtcacccctg gccccaaccc catgagccca agatggccaa gaggctgatg cagccttggg    3540
gctgaagggt tagtggggag cagggatggg gggtggggta tctgcagctc cctcatcttc    3600
atggcccttc tgtggcgtca ggaggacaaa acccacatgc ttagacacat ccttaacaca    3660
aagaaaccta agccgcttct tgcagcccag gaaaggacgc attctccagg ccaggatgtc    3720
agcctctacc aaggataaag agattgccat gggtcctata gcactgattg tcactgccct    3780
caggggacat tgggcgatga ctggagacat ttttgttgtc acgactggga aaggtgcta    3840 ctggcatctg gtgggtagaa gccaccactg taattctgca agacacaaga caacccctct    3900
aacaaagatt gtccagccca aagaggcaga ggtaccaagg ctgagccact gtactccaca    3960
gggaccctct tgtgctcagt cgtggtgtct ttgtcacctt cacaccaaga gcctggcatc    4020
caagaggtgc ccaggaatgg ttgtgaatga acgaatgaag caactcatgt cctatcctca    4080
gctctgctaa gagatggtga ttcatggtgt agacctcaca cttcccagtg tgttgttctg    4140
tccatgcagg gtccaagaac ccagagccca aatccagcag tcaaaatccc acagtgttct    4200
tgccagactg ggaaatctgg ctgccccgcc ctccagtgag ccggaagctg tgcagggcag    4260
ccttggctaa tcacctgcca cccagcacac ctggcaggag ctcagtgggt tgatgaaatg    4320
aggacagaaa gaaatagaag atccacaggc ccctggcagg ccctgctcac ataccacagt    4380
gggcacaaga cacgtcatgg agcacagggt gtggaaagac ctgggttcaa atcccagcct    4440
tgctcctcac cagtcatgtg accctggaca ggggactgac ctcttcagtt tttgtcaatt    4500
acaagtgggg ctaataatag taacaccttc ctcaaagggt taatgtgagg attagaagag    4560
gtaatccact gacagggttt ggtgcggtgc tacagactga agtggaaaag aatcttttgt    4620 ttttttttgag atgggtcat gctctgtcac ccaggctgga gtgcagtggt gtgatcacag    4680
ctcactgcag cctcgacctc ctgggttcaa gccatcctcc tgcctcaacc tcctgagtgg    4740
ctaggaccat aggtgcatgc caccatgcct ggctaatttt taatttttt tttatagaga    4800 caaggtctcc ccatgttgcc caggctggtc ttgaactctg ggcctcaagt gatcctccca    4860
cttcagcctc tcaaagtgtt gggattacag gtgtgatcca ctgcacctgg ctagaaaaca    4920
```

```
atctttgatg accactatca cagttcattt ccagtgcttg cccctctgcc tataagcccc    4980
tgtgccctgg ggctgagcct ggaagagtct gggaaggcta tagaacactt gctcatttct    5040
tgtggctgtg catcagcact ggggtaggct ctagggaaaa agagatgcat agaacgcagt    5100
cctgactgct ggagccgttt acagcctgtt gggactttag caaaggacta tactgggact    5160
aagatgagac gagactgcag caagcggtcc cagtgcactt gtaggactct gaatgacaac    5220
ttcttcaaaa tgtgtgtgcc tgactcacct tagtccctcc agcgaaggag cacatcctga    5280
gagggtcca gaaggcacag aagaggacaa gatgggacag ggctgcagg agtcttcagt      5340
ggttcctgga gaaggtttca agtctgctgc tgaacttgga agaataggaa gaatttcaaa    5400
aactgcaaat ttgcaaaact gagggcacat ttatacctgg gtaggaacca ataggaacaa    5460
agcctgcttt ggaggaaagc cctggacaag tttgggctgg gcagatagtt tgtaaattaa    5520
acccagagga ggccgggtga agtggctcat gcctgtaatc ccagcacttt gggaggctga    5580
ggcgggcgga tcacctgagg tcgggagttt gagaccatcc tgacaaatgt ggagaaaacc    5640
catctctact gaaaatacaa aattagcctg gtgtggtggc gcatgcctgt aatcccacct    5700
actcgggagg gtgaggcagg agaattgctt gaacccagga ggtggggatt gcagtgagct    5760
gagattgcat ccttgcactt cagcctgggt aacaagagcg aaactccatc tcaaaaaaca    5820
aaaacaaaa caaacacag aggaaataca tcatgatttg agcaaaggag acttcttttg       5880
taagagggca ggagctcaac ttccactaac cctgtaccta ggggttctct cacagtgcct    5940
agaggctgga gggctgtgag gctgggggag aggaaatgga ttcccctgac cgctgaagcc    6000
tgggggagca gaatagatcc agcctgacac acacgcagga tggatgattg cctacagatg    6060
cttcatcctt tggtggtgct gtcacggtga ggacagtccc tagtaaaatg tacagctggt    6120
acctgaaacg tggtgtgggg atttgaaggt gaacaggata gcttggtcac aggaagggta    6180
gtgacagagg aataaataaa tgtcaatgtg aggcgctaaa tgtgtcaatg ggggcctcct    6240
agagattgag tagaccccaa taagtaatca accaagagtg gtggttagga cgaggtaggt    6300
atgggtgagt aggagacaca tttggtaaca atgagatatg ttataaaata gaatgggctg    6360
gctggctgga aagtgagcgg gtacccctta ctagaattca gttcaattga tccagcattt    6420
atcaagcttt ctctaaatgc attcttctgg agtaaaacag taaataggat tttggaggct    6480
gttatgtcaa gggtaagagt atgagatagt tgccctcaag gagctgaaac tctaatggga    6540
aagacagaat ttccctagtg cacaggaggg agagcacgca aggctgggga cacctgagc     6600
caaggtacag gctctggaag taccggatgt gagcagggaa caagaggtag actgtgtggc    6660
tgaaatgctg ggtaggtgga gggatggagg gactggagag tggaagccac attctttttt    6720
tttttttttt ttttttttt ttttgagaca cagtaggctg gacgcagtgg ctcacgcctg     6780
ttatcccagc actttgggag gccgaggcgg gtgaatcacc tgaggtcagg agtttgagac    6840
cagcctggcc aacatggtga aaccccatct gtactaaaaa tacaaaaatt agccgggcgt    6900
ggtggcgggt gcctgtaatc ccagcttact caggaggctg aggcagaaga atcgcttgaa    6960
cccaggaggc ggaggttgca gtgagccgag atcgtgccat tgtactccag cctgggcaac    7020
aagagcgaaa ctctttttt ttttttttga gatggagtct cgctctgtga gtgtgaagca     7080
cagcgtgacc aagtaggagg gtgggagaca ggaagccctg gtggagggca agctggaggg    7140
gccccacagg atagagaggt cgaaggcctg acgagcagt ggcagggaag agggagggga     7200
gggccacaca ggagccaggc caaggacacg gacagacgat tggatgcagg gaagggggt     7260
```

```
ggggagggac tgaagataat ccccaggttc ctagcctctg ggagctggca gttgcctctg      7320
gtaggtaggc agagttctgc agcagcaggg ggccaggtca gggaccctg atggctctcc       7380 cctgctctgg aggtccctgg ctccatggtc agcacagcag tgctccagag tggctctggg     7440
ggcttctgag cagtggctct ttctcctccc ttctgcccct gcatagcag ttgaagtccc      7500 agtatccaat gcctcagctc tcccttctt tccccctcc caggactcac agaaaccctc       7560
tgtacccagt catgggccaa agacaccgtc atgcaagggg gtgaaggctc cacactcgtc    7620
ccggccccgg gcgtggaagc aggacctcga gcagtctctg gcagcagcct atgtgccggt   7680
cgttgtggac tctaaggggc agaatccgga caagctcagg ttcaatttct cacctccca     7740 gtactccaac tccctgaacc ccttctacac tttgcagaag cctacctgtg gctacctgta   7800
ccgccgggac actgaccaca cccgcaagcg ctttgatgtg cctcctgcca acttggtctt   7860
gtggcgctcc taggcctgag ccaaacggaa gcccccgacc cttcaccctc accctgtga    7920 cctcaggtcc caaggggaa gggctgctca ctgcaggagg agtgacctat attcgggcta    7980
agacagctgt gccatgccca cctattgaca atgataaagg gaggtctctc ttctcagcag   8040
cagttaaagt ttgtccttcc tttccctggc atctgaatgg gtggctgtgg gtaggtaaac    8100
aggccatggg gatgttatac agtaaggtta tgtccagagg tttctgaaga cttggaagga   8160
cttgattctc agttccctaa ccccaaaagt aacctcaacc cttctccaga gctgagtccc    8220
aagcaaagcc catcctagct ccagcctccc gatggtccag gctcggaccc ctccaaggaa   8280
gagagggtgg gtgtggtggc tcacacctgt aatcccagca cttcaggagg ccaaggtggg   8340
cagatcacct gaggtcagga gttcaagacc agcctggcca acatggtgaa accccgtctc   8400
tacaaaaatt agccaggcat gatggcaggt gcctataatc ccagctactc gggagactaa   8460
ggaatgagaa tcccttgaag ccaggaggca gaggttgcag tgagccgaaa tcatgccatt    8520
gcactccagc ctgggtgaca gagtaagact ccgtcaaaaa aaaaaaatta atttaaaaaa   8580
aggaagagat ccatcaactg gccatgactc ctgctctctt acaaggtcat cttaccctgg   8640
ttggagcagc tgctgcagaa tgaggaagaa tgcagggaat gaacacagac tctaggtccc   8700
ctcccagacc cagttttaca taaagctgct gcttctgact tgtagtttgt tggtgggga    8760 aggatttccc atccttgccg tctcctctgg tctagaagag ctggctctga ggctagttga   8820
gctcatgggt catggggcat ggaagagggg gatggaggca gagggcactg gattcacagc   8880
aggggcctga gtgagttccc agtcactgcc attcagaggg aaccccagtg gtgtgctgga   8940
gccagcttgt actgacttgt aagagctggt tgtgcccatg tcttccctac tccacaatca    9000
gtgatttctt tttttttttt ttttgagacg gagtctcgct ctgtcgcccg ggctggagtg   9060
cagtggcgtg atctcagctc agtgcaagct ccgcttcccg ggttcacgcc attctcctgc   9120
ctcagcctcc tgagtagctg ggactacagg tgcccgccac cacacccggc tatttttttt   9180
tttttttttt gtatatttag tagagatggg gtttcaccat gttagccagg atggtcttga   9240
tctcctgacc ttgtgatctg cccacctcgg cctcccaaag tgctgggatt acaggtgtga   9300
gccaccgcac ccggcccaca atcagtgact tcctgttggc agtttggaat cagctgtggt   9360
gggagcattt acaccacaga agtgagcaaa tgcctacaaa ttggagtttc tttttttccag   9420 agagctcatc attaaacatt taccagcaca ccacagggtg aattcagctg gtttcattcc    9480
taggagtctc gtccctctgt aggtatggtg gtgtattctg tggggcataa ttcctgtgca   9540
ggagaggttg gggttggtgt gggaaggaga gacaggtgtc cagagacccc gacaagcagc   9600
ccacaacaag gccaggctgt cctgtgggcc tttctttgag aagatggtaa gcagtgtgga   9660
```

```
gggaagtgga gacccctcga ggcgacccta acagcataga atccgcgttt tcctcttggc    9720
ttgctgtagg ctctcttttg agttagaggt tttcctcaaa tgcctgatga gccttggctg    9780
gcctcagacc atctggcatc tgtaccaggt ctctccttct gcttggtcat cagtgttcaa    9840
ggagccagcc acgggaatga gctggggtgg gggaaggcgc atggtggttt tctcactgtc    9900
catatgtaga ctttctttta acgctccatt tatagaatgg cacatgtctc ttcctgaggc    9960
tgtgcctaga gactagcggc tctctggccc aaatctccag aagaaccttc aatcagggtc    10020
aggaggggac tgatgccggg agatgcctgt tctgctgcct tgcggagggc atcggagaag    10080
ctaagtgttc cttatgcaaa cttttggccag ccctatttttc tgctccacct gtgctgcatc    10140
ccagccttca ggggcacctg gtatctctgc ctccctattc ctgcagcagg aataggtttg    10200
tcccgagctc cgcaggctcc tcctctttga aagcatttag gtttcgactt tctccactct    10260
cataagaaag acagttacca cttgtccatc tgtcttgttt tccaaaattt tattagaacc    10320
cctgtatctg ctgtctttttt tcctctttttc ttttctttct ttcttttctt ttttctttttt    10380 ttgagataag agtttcactc ttgttgccca gtctggagtc caatggcggg atctcagctc    10440
accacaactt ccacctcccg ggttcaagcg attctcctgc ctcagcctcc cgagtagctg    10500
ggattacagg catgggccgc catgccctgc taattttgta ttttttagtag acgggggtt    10560 tctccatgtt ggtcaggctg gtcttgaact cctgacctca ggtgatccac ctgcctcggc    10620
ctcccaaagt gctgggatta caggcgtgag ccactgtgcc cagcccctttt tccttttttt    10680 gagacggagt tttgctcttg ttgcccaggc tggagtgcaa tggtgcaatc ttggctcacc    10740
ataacctcct cctcccaggt tcaagcgatt ctcctgcctc agcctcccgg gtagctggga    10800
ttacaggaat gtaccaccat gcccggctaa ttttttgtatt tttagtagag acggggtttc    10860
tccatgttgg acaggctggt cttgaactcc cgacctcagg tgatccgccc gcctcggcct    10920
cacaaagcgc tgggattaca ggcgttagcc actgcgcccg gcctcctttt gtctttaaaa    10980
catgcattta ttcatatttt agtgggattt tgaaaagaag cagagataag tggaagttttt    11040 cagtctatgt ataactagaa gtcttgctca ttcaatcagt cagtcaccca acagaccctg    11100
tgggctgtgt ccttaagatg caaagatatt aacaggaacc gtcccttccc ttccagatcc    11160
tatagcctgt gtagggtgag gggcaggatc cccatgaggc gtcttcactc ccacaacaaa    11220
cgcctcctcc cctaccctgg agaatgggct ccctcttgag gttcacctttg gtaatgcagc    11280 ctccatggac gcccttagaa acccttaaaa gaaaccggcc aaggtaccac cttgttttga    11340
gtgagatagg cccaggaggc aactgaacct gtgctcaggg tccttctgtg tttctgtgga    11400 gtagagggc aagcaggcag ccttaggggg ggattagtct ggcctggatc actgcccctc    11460
ctgtctcttc ctggtttgtc ttcctacctc tctgcagctg cccatcctc cctccctcg    11520 gccccattcc gccaggtgga gcctcttcct ctgatctggc ttctgtccca ggagggattc    11580
ctgcaggcag agcagccagg gaaggcagga atcctccctg tgtatgctgt gtgacctgta    11640
ctctggccct ctgtgcccta acgcatacct tgtgcatact gcttccttgg ggccttggtg    11700
ttgatctcag tcctccttgc cttggcatcc ctgtctcagg ggattccatt cccaccctgg    11760
gctggagaca aggggtgggg gccctcctcc ctcaaaggga gcaagctctc tgtcaatgga    11820
attgttgggc agagggccac aaggggagga ctgagggaga tggcgctgga gtgaggggct    11880 cgtgggtcc ccctggctct atccagccct tctgcagggt gtgaaggctt aggagaaaag    11940
catgatgatg aggtgggaaa actttggtac caccactaaa gtgctcgtga acctgagcag    12000
```

```
gtgatttaaa ttttctgccc caagcccctt ttgtctcaca tggcaataat aatacccacc    12060
ccacaggact tgtgcaccta ttcaacaagc atagtttcat ccaattttag cttttttgaga   12120 attctttctt tctttctttc tttttttttg agacagtctc gctctgtcgc ccaggctgga    12180
gtgcagtggt gcgatctcgg ctcactgcaa gctccgcctc ctgggttcac gtcatcctcc    12240
tgcctcagcc tcctgagtag ctgggactac gccgccaagc ctggctaact tttttttttt    12300
tttttttttg tattttagt agagacgggg tttcaccatg ttagccagga tggtcttgat     12360
ctcctgacct tgtgatccac ccatctcgtc ctcccaaagt gctgggatta caggcgtgag    12420
ccaccatacc tggcaagaat tttttttgat ttggagcttc actcttgtca cccaggctgg    12480
agtgcaatgg cacgatctcg tctcactgca acctctgctt cccaggttca gtgattctc     12540 ctgcctcagc ctccagagta gctgggacca caggcgtgca ccactatgcc cggcttattt    12600
ttgtattttt agtagagaca gggtttcacc atgttggcca ggctagtctc gaactcctga    12660
cctcagatga tccacccgcc tccgcctccc aaagtgctgg gattacaggt gtgagccacc    12720
ctgcccggcc taagaattct tttcttttct cttttatttt cttttctttg acgaagtttc    12780
gctcttgttg cccagactgg agcacaatgg cgcgatctcg gctcactgca gcctccgact    12840
cccaggttca aacgattctc ctgcctcagc ctctggagta gctgggatta caggcacccg    12900
ccaccacacc cggctaattt ttgtatattt agtagagacg gggtttcacc atgttgacca    12960
ggctcgtctt gaaccccga cctcagatga tccaccctcc tcagcctccc aaagtgctgg     13020
gattacaggc gtgagccacc gcgcccggcc caagaattc tttctttaat catatgtgca     13080
tgcatgcatg cactcaatat tttactgggc tcaagcccgt cagtcaaata ttactctcaa    13140
aacggtaatt taggagagtt gatgtgggga ctattaacag agagctgggc atagttaagg    13200
gaatggtgat gtacccagac agtagcgaga gggaagccct tatcatgcct ggcggggcaa    13260
agggagggag ccatgattac aggagcccag agagctatgg caggagcggt gattgaaggt    13320
ggaaggaaat aaccgctgcc ccaaccctga gctggcaggg aggagtgagg acaacaaatg    13380
tcccagctct tctccctctc caccctccag tcttcctcca gcttctcagc agatgaaccc    13440
agcctgaaac aagagggcag cagagtctgg gtgatgcagt ctgtagggtc agtctttggg    13500
gctcagagct ggaggagaaa gggggagaat gagtcggggc tgggcaaaca gaacaactag    13560
cgcacgacaa tgtggaatgt gtggtgccag gagctggggg caggcgagac acaaataaca    13620
gaatggtctc caccctctgt gagcttgctg ggttccttag agcaggctgg caagaagagt    13680
tgcctatata atacttctgg aaagaaatga atgctatgtc cgtgttattg tagaagagtg    13740
aatgtcataa tagaccctaa ggtgacccca gtgatttcta cctcctgttg ttcctacctt    13800
tgtaaaattc tctcccttg agtgtgggtg aggcccttga cttgattcta acccatagaa     13860
tatggcaaag gtgatgggac gtctctctgt ggattatgtt aggttatata gactttagca    13920
gattgcagag agactcttct cgctgacttg atgaaataag cagcgtggtg aggaagctgg    13980
tgtaacaagg aacagagggc agcctctatg acctgagtgt gtcccccagg caatgtcaag    14040
tgaaaagcca gctcccttgt cacatagcca caacaaaatg agttctgcca caacctgaa     14100 taagttggaa gtggattctt ccccagttga gcctccagat gaaatacag cccaggtgac     14160 accctgagag cagccttgtg agacgctagg cagaggacca gctaagctgt gcctggactc    14220
ctggcccata gaaactgtga gataataaat gtgtggccag gcacggtggc tcatgcctgt    14280
aatcgcagca ctttgggagg ctgaggcagg tggatcacct gaggtcggga gtttgagacc    14340
accctgacca acatggagaa accctgtctc tactaaaaat acaaaattag tggggcatgg    14400
```

```
cggcacatgc ctgtaatccc agctactcag gaggctgagg caggagaatt gcttgaacct    14460
gggaggcagg aggttgtgct gagccgagat cgcatcattg tactctagcc tgggcaacaa    14520
gagtgaaact ccatctcaaa ataataataa taataataat aataataata ataataataa    14580
taataaatgt gtgtagtttt aaaactgctg actttgtggt tatttgttat gcaacataga    14640
aaactaatat aacacacaca ttagccagag ttcttcagag agacagagct aataggatta    14700
tatatagagg tatgagagaa gatttattag ggggattggc tcacatgttt atggaggctg    14760
agaagtccca caatatgcca tctgcaagat ggagaaccag ggaagccagt agcatggctc    14820
agttcaagcc caaagggttc agagccaagg aaactgatgg tgtaactctg ggtctgaagc    14880
tgaaggactg agaacgtgag agtggggagg ggttgctact ggtgcaagtc ctggagtcca    14940
agggcaggag aagaagagtg tcccagctcc aggacagaga gagagagaga gagggagaga    15000
attcaccttt cccctgcctt tttcttctgt ccaggcctaa gccaattgga tggtgcccac    15060
ccacataggc tgaaggcaga ttctccttac ttagtccatg aattcaaatg ccagtctctt    15120
tggcaagcac cctcacagaa acacccagaa ataaagcttt accagcttgt tgggtaatcc    15180
cttcatccag tcctaaaatt aactgtcaca acacataagc aaaatgtcag tatgctgtgg    15240
gaggaagata tttgagagag atttgggaag gcttcacaga ggaggtggca tttgtactca    15300
cacatgaaga gtgagaggga tttaaataga aagggaaaga tgagcggctg ccttgtcccc    15360
aacctcttca tttcccaatc ttgggcctga gagtcctcgg caaggacaca ttttccagct    15420 gggcccaag caagttcaca gaaggagtcc ttctctcccc gtcccttaac ttgttgtgga    15480
gaagctgact gaagcaggga gaacccagct ccccaccccc atataccttc cgtcaatcaa    15540
ttcatgtgga gtagaggtaa aacagtccca gtttgtctct ttttcaaaaa taactatcct    15600
ctttgatttt gtgagcaaca tatgttcatt atgaacaatt ttttttttt tttttgagat    15660 ggagtctctc tctgtcgccc aggctggagt gcaatggcgt agtctcggct cactgcaaac    15720
tccgcctccc aggttgaagt gattctcctg cctcggcctc ccaagtagct ggaattacag    15780
gcgcccacca ccatgcctgg ctaattttg tattttagt acagatgggg ttttaccatg    15840
ttggccaggc tggtctcgaa ctcctgacct tgtgatccac ccgccttcagc ctcccaaagt    15900 gccgggatta caggcgtgag cctggatctg gtaaggcttt aacaaaggcc tccaccttcc    15960
ctagggcctg actacagctg gtaggtggcc tgtgtgaggc aggttggatg tctgttccta    16020
cacatagccc ttctggccgt ccagggccca gagtgaatgg ggctaaaggg acaagagcac    16080
gattggctct aacccaggga tgctgctgtg tccaagatgc agtataagtg cacctagatt    16140
gtagtgaaca gcacatcaga catgctgctg taatagatac aaaatcataa catcatagcc    16200
aagatttatg gggcacttac tctggggcag accttgttct aaatgctttt cttatattaa    16260
ctcacatact ctttttttt ttttttttg atatagggtc tcgctttgtc attcaggctg    16320
gagtgcagtg gtgcgatctt ggctcactgc aacctccgcc tcctgggttc aagcgattct    16380
cctgcctcag cctcccgagt agctgggatt acaggagtgt gcaccatcac gcctggctaa    16440
tttatgtatt tttaatagag atgaggtttc accatgttgg ccaggctggt ctcgtactcc    16500
tggcctcaag tgatccaccc gcctcggcct cccaaaatgt tgggattaca ggtgtgagcc    16560
accgtgccca gccccactta ctccccttaa cagccctatc agatgggcgc cattattcct    16620
attttaagaa tgaggaaact gggggcccaga gaggttaagt tacttgctca aggtcaccca    16680
gccagtaatg taagcaagaa acaagcttgt attgttttca gccactgaga ttttagagtg    16740
```

```
gtttgttact gtagcataac ctagcccatt ctgaaatatg tatgcacatg tatttgatat    16800
atgttatatg ttgtataaat tgtatattta tataaatcta tttacatgta attatatatt    16860
atttatataa atcatataaa ttgtgtatca gtgcacaact tgaccaagtg tccaaggccc    16920
tggtggggaa agcagaaata tgggcagtgg ttccctctag atgagttagg agacctgggt    16980 gtgcccata tgtaaaggag gaaggcaaac aagagaaaaa gacagggcag ggcaagcgct    17040
ggctttaagc tttcctggca gcatccaggt taagtgcacc tgcacccaaa tgctggttcc    17100
ataaatgagc cagcttttaa gtgtgtggct agggagtacg catcccacca ggcatcagag    17160
aaagctgttg ctgcatagac aggccccag gcttggcctg ggagctttcc aggaccagca    17220
ggtagcagct cacccatgca cctgtgtgcc tgcactctca cactcacaca taccccaggg    17280
caccaggcgc acactccatg tcccctgccc tgtgccccta gtaggtgatg gtgatgatgt    17340
gaggctcaga attagatgga aggatgaatt cagggctctc aagaagggag agatgcaacc    17400
ttcaggaaca tgagagtgtg gccagaacag gatgagtgtg tacgagtgtg tgtatgtgtg    17460
tgcacgtctc tgtgtactgg tgcaggctaa tgtaggaggg ggttctctct ggctgttcaa    17520
ggcttatctt ggaagcccac agactctgca tccacccagg tgccctcaaa tgttagcaca    17580
ctcatggtat gattggaccc cctcagttgt gatggccaag tgcagtgcac agcctggata    17640
actgtacaca gcagccctgt caagagccca cagttggcca tctctggaca agaagccagc    17700
tctatctcat atatacctca attccatgat tgaaggcaga atccaaaacc actgtgaatc    17760
cactcaaacc aggagaagaa ggtcacaaag gtcataggat cagagcagct tctagctgac    17820
acccactccg tggtggtaag aagggattag aagattgcaa actgggttaa aaaatcctct    17880
cacctacagc tcaaggctgt aatcctaagg actctgcttc tctaagcctt gttctatttt    17940
caactctttt ctccagggta cagtctcccc tggggctgca aggatttagt ggagactctt    18000
aacaccagtt ctctggcatc tgtgagtttg agtgtgggcc atcatcttct tccttctgct    18060
ctctccctct ccacatttcc cggtaccatc tgatccatca ggcccttctt tgctcaggcc    18120
tgaaggactc aggcctgtga gagaggacgg ccccgttgtc ggccaagaca cctttgggcg    18180
aggagcagcg aacagggcct gtccatctca gacgtcagcc ccctgaaggc ctgagcaatg    18240
ggcaacgtga tggagggaaa gtcagtggag gagctgagca gcaccgagtg ccaccagtgg    18300
tacaagaagt tcatgactga gtgccccctct ggccaactca ccctctatga gttccgccag    18360
ttcttcggcc tcaagaacct gagcccgtcg gccagccagt acgtggaaca gatgtttgag    18420
acttttgact tcaacaaggt gagcaggggc ccagtggcag ggaggggaag tgctggaggg    18480
acccctctgg aagcctgacc agctggggt gaggaagagc agagaggagc atagaagtgt    18540
ccgctgggga gcaacttcat ttatacagtc atttgtttat ttgataggtg ggtttttgac    18600
actagggttt caacggatct aatgtttgtg ctttaatgag caccaactgt gaatcaggca    18660 ctgggggtt agaaatgtat cagacattgt ccctgccctc actttctagg gcaagacaga    18720
gaggcccaca cattagtgta atccgaggct gaatccaatg gcttcctcca cctctgccac    18780
aggcatatct tggtttactc caaaacgagt gtaaacactt ccaagatggt cattgaacac    18840
ctgcgatgtg ctggtcctat acgtggtgct tttgcaaaca ccctttgaag ctcccaagga    18900
tgtgggcaga ggggcagaga gcagggagca agatgatgat tctctagcct cactgtctgg    18960
catgggcagg ccacttataa tattctgcgg acatgaggac tggagacaga cagggttgcc    19020
tggtccctgg agaacccaga atgctcccaa cttcaaaata cccagtgacc tcatatcacc    19080
ttttctcaag tgagcctgaa ggtccacacc gtggtcaaat tgtgtctcct cagtagccac    19140
```

```
ctggacgcat taggtaagga cttcctaatt gataagctag aggggtcact gaaaggtgag   19200
tttgggactg tgggtttggg tccctagctt tcatccgctg ggtgaccttg agcccatcat   19260
ttcccctctc agtcccagta tattcatgat gccgtggatg ttgggagcat tagttaagat   19320
gtttgttggt tttcatagta aatcttccat tcatttggaa ctatttggtc aagacatagt   19380
tgtggaagag cccaaatctg caaacgtggc tccccaccct gtggcccctc acttgaaaag   19440
tgaggatgca atgaggcgct gccgcgtgtc ctctgcagac ccgggagagg ttccttccct   19500
cgctgcccag aaggtccagg caccatcatg ggtggggctt cttgggaaag ctgggctca    19560 gtggctattt aaaactcact aatatttaag gataagggac caaagtagat tacgggcttt   19620
gagtgtcaac ctcaggtgta gtatgaggga gcccaagggc tttcccgaag cgggagcagg   19680
tgagcagagt ccagagcctg tgtacagaga ctgggaggga tggcatcatc acattcaaca   19740
ctcaaaatgc tcccgaagaa ggaataactc ctgaacagga ggggaaggac aaatggatgg   19800
ttgagcctca caccttaccc ccaaacagcg acatatctca tcttctcacc tgctaagaaa   19860
acccttgggg ttaagacatg tctgcagaag gaccccttaca gtcacacata tgacgccggt   19920
gggggtgggg gagggcaacc ctggggcaca tcgaccctgt atttgcctaa tcatgtcttt   19980 ttttttttt ttttttttt ttgagatgga gtctcgctct gtcgcccaga ctggagtgca    20040
gtggcgtgat ctcggctcac tgcaacctcc acctcctggg ctcaagcgat tcttctgcct   20100
cactcagcct ctcaagtagc tgggattaca ggcacccaca accatgcctg gctaattttt   20160
gtatttttag tagagatggg gtttcactat gttggccagg ccggtctcaa actcttgacc   20220
tcaggtgatc cgcccacctc ggcctcccat agtgctggga ttacaggcgt gagccaccac   20280
gctgagccaa ccatgtctta atgtgtgtcc catgcgagca ccacctgtac tgtaccaaac   20340
ctgacccttg tctttccact gaaagtaaat caaccccttg tttctaggca gtctggcctc   20400
ctcccttatt ccacacacac ccccgcctta ggggttttgt gctgcctggg accctctctg   20460
cccccagaat tctgctcggc ttacccttc ctctgctgca agtctctgct tagaagtctc    20520
ctcactaacc cctgccgtga tcttctggtt taaaactctgt ttaaaactgg gactggttcc   20580
cacctctgca tttcctagtc ccaccttttcc ccgcaagcac ctgtcgtctt ccaataccag   20640
atttaaataa catttcacca ttacgtttat cgcctgtctc cccctgctgg aatgtgagct   20700
ccatgtgggc agggattttt gtcttgttca ctgttgaatc cctggttcct agaacagtgc   20760
ctggattgtg gcaggtgctt aataatattc attgtatgag tgaatgaata tatgagaaat   20820
caggaattta atggctagtt atttttataat atacatcaat ttaactctgc aaatattaaa   20880
atgaagagtg actttgtaac acccaacctg cctcatctac acccatggca cacaatcaca   20940 cttttgcataa tactgtcttg acccattgtc atcagcatgg agcagtttag cagattggct   21000
aggagatgga acacaggatt gggaagtttt tgttgttgtt gttgttttgt tttttgttgt   21060
tgttgttgtt ttttgagatg gagttttgct cttgtcaccc aggctggagt gcaatggcac   21120
gatctcggct cactgcaacc tccacctcct gggttcaagt gattcttctg cctcagcctc   21180
ctgagtagct gggattacag gtgcccacca ccacgcctgg ctaattttttg tatttttagt   21240 agagacaggt tttcaccaca ttggccaggc tggtctcgaa ctcctgacct caggtgatcc   21300
acctgcctcg gcctcccaaa gtgctgggat tacaggtgtg agccactgca cctgtccaga   21360
agttttgata cagagaggag ttaaacaggg acaggcaaat gacagcacac aggcctgttt   21420
ttgtaaatga agtttttatta gaactcacca catctatttta tttacgtaga gaattgtcta   21480
```

```
tggctgctttt cacgtaaaat gacagagggt gtttggctgc aaagctgcat atttactctt    21540 tggctctttta cagaaaaagt ttgccatttt ctaataaaaa ctaaaaagtt tttagtgcaa    21600
gtgccagccc ttgcactaaa aaatggttgt atctttgggt attgcaccag atgtgcaggg    21660
ctggggagta cagagtgtga ctggggagtg aaacctgggg gacaggccat ttgcttttgct   21720 tacttcaaat gtttgtctgg gcttgggttt gtctgacaat cacacaggtg cacacaaatc    21780
aatgcaaatc tccatctgca tttgagtact gatataggat gatttaggag aggctttgtc    21840
attcactagc tgtttggcct aatctctctc aactttggct ttgtcattca aactagagac    21900
aaaaatattc acctcttggg ggtggcttga gattaaatga gtaaatgaa taaagcactc      21960 agcctaggaa gtccatggag agcactaaga aaagttagta ttgctatata ttttcattga    22020
atctaatgca taccacaatc ttgaaaagtg cacactgtca ttccatttta tacctgggaa    22080
tacggagact caaggtcatg tgacttatcc aaggtgattt agatctttct ggcacaaaaa    22140
tccacacctt ttccattgcc ccttttttaga cattaaaaaa aaaacctgca aaagcaatcc    22200
agctcattgt agaaatttcc agcaatacag aaagataaaa aatgaagagc aaaagtatcc    22260
tcacctggtg tccccctcccc cagaggaaac ctctttagca gttttcttgc ttattcaagc   22320
tgtgctgtct aggggcctct ctgggctctg tgctgatgac agtcctggga ggtgggttgg    22380
gactgaatga gcccactgtg gggttcagag tgtttaaggc cttccggggg cctcagcccc    22440
tcaggcagca gggtgagaaa ctcccaaaag ctcacccaaa ccacgctccc atccctgggg    22500
gtgcagttct tcctcctccc acctacgcac atgtctccca tttcccctaa ctggaaaggc    22560
tcatgcttga caatcacagg gaagcaggca gcgctcgcta aaacccagat gcctgtgaac    22620
agacagcgcc agccattcac accccagtgg atgctggctt attagatttg attggcagcc    22680
tctggagtag gcagggtggg ctatacaggg cgtctaggaa gacagatagg tcacggcgga    22740
gacagggctg gccccctcgc tgcatctccg agggtccggg tctcccctca gcgtctcttg    22800
gggcttgccg agatgggcgg agccttgggt tatgatgggc ggggcctgag gctggagtga    22860
gcggggcccg gatgggctca cggcggccgc gccccctcgcc caggacggct acattgattt    22920
catggagtac gtggcagcgc tcagcttggt cctcaagggg aagtggaac agaagctccg     22980 ctggtacttc aagctctatg atgtagatgg caacggctgc attgaccgcg atgagctgct    23040
caccatcatc caggtgcaga gggcccggcc agggctgggg gcagcggtct ggggtgggac    23100
ccggaactga gagcccaggg ttagaacaac aatctcagga ttgagacagg atgtgggact    23160
gaggatcctg gtgcagctg taggcctcac cagctgcgtg acccaggcca cgttccttcc     23220
cttccttggc ctcagtttcc tcatcaatac caaaagacga tagaagtttg actcttgagt    23280
cccagctctg cctaggcccc cgggtaccct gcactctact cctcactgct cttgggagcc    23340
ggacaagctc tgaccgtccc caatcctacc cctgagatag gataaggatg ggccctctc     23400 acttctgccc cttcttccct cccaggccat tcgcgccatt aaccctgca gcgataccac     23460 catgactgca gaggagttca ccgatacagt gttctccaag attgacgtca acggggatgg    23520 tgaggggggcc gaggaggggc tccccagcgg agggtcacc atggatgtgg ggtcaccagg    23580
ggtggaaggt cactaaagga gagggtgagg aaggaggag aggcccaaag gccccgtgc      23640 tggtcacttc ctccacctgc ctctgccccca gccacaaagt tggcttttag gggcccctgg   23700
accagaatct gggctctggg ttcctctgct tgctgcaccc gcagcagggg ctctgacttc    23760
tcctcacgtg ggctctgtcc ctgccctgg caagaacccg gttctgtgct ctggactgca    23820
gaaatgaaca ccctcctccc cctgattccc tttctctcta ccccagggga actctccctg    23880
```

```
gaagagttta tagagggcgt ccagaaggac cagatgctcc tggacacact gacacgaagc    23940
ctggacctta cccgcatcgt gcgcaggctc cagaatggcg agcaagacga ggaggggggct    24000 gacgaggccg ctgaggcagc cggctgagtg caccgcccgg ctgcttctgc actagcgggt    24060
ggggtggtat ggtggtgcct gttggtggtg ttcttgtctt aaccctagat agaatctaat    24120
gaactcagag gcttagctcg cctctttagg gtccatggtg gcagcagaga ggcagaagtg    24180
ggagtccaga gccaggaaca gtgaaggatg gttcctggcc cctctgagtg acagctggtg    24240
gcagcactcc ttgctggggg gcactgttca acatccctct gccgtcgggt gacccccctag    24300 cccttctgac tcctctccca gcttttccca gctttcccca ctgagcttct ccagtccatg    24360
ctcttctgga cgtggactct ctgaggcaga actgagcttt tccaggcctc ttatggaatc    24420
ctgcagatcc agtggctgca gcttcaatcc cagtgctgca atcacacatc cattctgccc    24480
tgggggaccc tggagcctac ttgtgcgctt tgcatttcat tgattgacgc ctcccttcaa    24540
caagcattta ctgagcgcct actatgtact aatgctagat gttagatgta caaagaagac    24600
agttttcatc ctctaggaac tcataggcta atggtgagac acacagacaa acatcattat    24660
aataaaatat gctaagagaa gttatgaata gatttctgta aagaca                   24707
```

<210> SEQ ID NO 9
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 9
gaccgcgtca tagatggtgc ca                                              22

<210> SEQ ID NO 10
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 10
gcaagaagac cgcgtcatag atggtgccaa agagtgggga gacctgc                   47

<210> SEQ ID NO 11
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 11
gcaagaagac cgcgtcatag atggtgccaa agagtggaga gacctgc                   47

<210> SEQ ID NO 12
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 12
acaggaagac agcatcatag atggtgccaa acagcggaga gacctgc                   47

<210> SEQ ID NO 13

```
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 13
gacgtagaga gcatctgcag c                                              21

<210> SEQ ID NO 14
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 14
taaggaggac gtagagagca tctgcagcgg gggtcaccgc cggggc                   46

<210> SEQ ID NO 15
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 15
gaagcagggc gtagaggcat cggcgggggt cacggcaggg gc                       42

<210> SEQ ID NO 16
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 16
gaagcagggc gtagaggcgt ccgctgcggg ggtcaaggca ggggc                    45

<210> SEQ ID NO 17
<211> LENGTH: 34
<212> TYPE: DNA
<213> ORGANISM: Mus musculus

<400> SEQUENCE: 17
ggtgaccccc gctgcagatg ctctctacgt cctc                                34

<210> SEQ ID NO 18
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 18
ggtgaccccc gctggcagat gctctctacg tcctc                               35

<210> SEQ ID NO 19
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 19
ggtgaccccc gagatgctct ctacgtcctc                                     30
```

```
<210> SEQ ID NO 20
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 20
ggtgaccccc gctagcagat gctctctacg tcctc                              35

<210> SEQ ID NO 21
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 21
ggtgaccccc gctagatgct ctctacgtcc tc                                 32

<210> SEQ ID NO 22
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 22
ggtgaccccc ccagatgctc tctacgtcct c                                  31

<210> SEQ ID NO 23
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 23
ggtgaccccc gctatgctct ctacgtcctc                                    30

<210> SEQ ID NO 24
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 24
ggtgaccccc gctcgcagat gctctctacg tcctc                              35

<210> SEQ ID NO 25
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 25
ggtgaccccc ggcagatgct ctctacgtcc tc                                 32

<210> SEQ ID NO 26
<211> LENGTH: 30
<212> TYPE: DNA
<213> ORGANISM: Artificial Sequence
<220> FEATURE:
```

<223> OTHER INFORMATION: Synthetic Polynucleotide

<400> SEQUENCE: 26 ggtgacccccg cagatgctct ctacgtcctc                                           30

<210> SEQ ID NO 27
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 27
ggtgacccgc agatgctctc tacgtcctc                                             29

<210> SEQ ID NO 28
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 28
ggtgaccccc gctgcagatg ctctctacgt cctc                                       34

<210> SEQ ID NO 29
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 29
ggtgaccccc gcttctctac gtcctc                                                26

<210> SEQ ID NO 30
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 30
ggtgaccccc gctgggcaga tgctctctac gtcctc                                     36

<210> SEQ ID NO 31
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 31
ggtgaccccc gcttgctctc tacgtcctc                                             29

<210> SEQ ID NO 32
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 32
ggtgaccccc gcgcagatgc tctctacgtc ctc                                        33

<210> SEQ ID NO 33
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 33
tcctatccac gacaggacca agactgt                                        27

<210> SEQ ID NO 34
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 34
gagagcagaa gggtagcatt agctcag                                        27

<210> SEQ ID NO 35
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 35
accgctatca ggacatagcg ttggcta                                        27

<210> SEQ ID NO 36
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 36
gttcttcgga cgcctcgtca acac                                           24

<210> SEQ ID NO 37
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 37
gtgcctacag gactcttgat gtcattc                                        27

<210> SEQ ID NO 38
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 38
caagacattt gacaggagtt actc                                           24

<210> SEQ ID NO 39
<211> LENGTH: 25
<212> TYPE: DNA
<213> ORGANISM: Artificial Sequence
<220> FEATURE:
<223> OTHER INFORMATION: Synthetic Polynucleotide

```
<400> SEQUENCE: 39
gttctgagct acagatccta cagtg                                           25

<210> SEQ ID NO 40
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 40
cgatccaaac aacatctgcg gt                                              22

<210> SEQ ID NO 41
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 41
cagccaaacc ctgtctccct cat                                             23

<210> SEQ ID NO 42
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 42
tctcgccaac aagttgacga g                                               21

<210> SEQ ID NO 43
<211> LENGTH: 39
<212> TYPE: DNA
<213> ORGANISM: Mus musculus

<400> SEQUENCE: 43
cggtgacccc cgctgcagat gctctctacg tcctcctta                            39

<210> SEQ ID NO 44
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 44
cggtgacccc cgctatgctc tctacgtcct cctta                                35

<210> SEQ ID NO 45
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 45
cggtgacccc cgcgcagatg ctctctacgt cctccttaa                            38

<210> SEQ ID NO 46
<211> LENGTH: 30
<212> TYPE: DNA
<213> ORGANISM: Artificial Sequence
```

```
<220> FEATURE:
<223> OTHER INFORMATION: Synthetic Polynucleotide

<400> SEQUENCE: 46
cggtggcaga tgctctctac gtcctcctta                                              30

<210> SEQ ID NO 47
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 47
cggtgacccc cgctagatgc tctctacgtc ctcctta                                      37

<210> SEQ ID NO 48
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 48
cggtgacccc cgctacgtcc tcctta                                                  26

<210> SEQ ID NO 49
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 49
gcagatgctc tctacgtcct cctta                                                   25

<210> SEQ ID NO 50
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 50
cggtgacccc cgcagatgct ctctacgtcc tcctta                                       36

<210> SEQ ID NO 51
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 51
cggtgacccc cgctctgctc tctacgtcct cctta                                        35

<210> SEQ ID NO 52
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 52
cggtgacccc cgctagcaga tgctctctac gtcctcctta                                   40
```

```
<210> SEQ ID NO 53
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 53
cggtgacccc cgctgatgct ctctacgtcc tcctta                              36

<210> SEQ ID NO 54
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 54
cggtgacccc ccgctgctct ctacgtcctc ctta                                34

<210> SEQ ID NO 55
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 55
ctgcagatgc tctctacgtc ctcctta                                        27

<210> SEQ ID NO 56
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 56
cggtgacccc cgctcagatg ctctctacgt cctcctta                            38

<210> SEQ ID NO 57
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 57
cggtgacccc cgctttcgca gatgctctct acgtcctcct ta                       42

<210> SEQ ID NO 58
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 58
cggtgacccc cgctggcaga tgctctctac gtcctcctta                          40

<210> SEQ ID NO 59
<211> LENGTH: 40
<212> TYPE: DNA
<213> ORGANISM: Artificial Sequence
<220> FEATURE:
<223> OTHER INFORMATION: Synthetic Polynucleotide
```

<400> SEQUENCE: 59
cggtgacccc cgcttgcaga tgctctctac gtcctcctta        40

<210> SEQ ID NO 60
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 60
cggtgacccc cgctctctct acgtcctcct ta        32

<210> SEQ ID NO 61
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 61
gggtctgctc tctacgtcct cctta        25

<210> SEQ ID NO 62
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 62
cggtgacccc cgctgtgtgc agatgctctc tacgtcctcc tta        43

<210> SEQ ID NO 63
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 63
cggtgacccc cgatgctctc tacgtcctcc tta        33

<210> SEQ ID NO 64
<211> LENGTH: 44
<212> TYPE: DNA
<213> ORGANISM: Macaca fascicularis

<400> SEQUENCE: 64
ctctccactc tttggcacca tctatgacgc ggtcttcttg ctgg        44

<210> SEQ ID NO 65
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 65
ctctccactc tttggtatga cgcggtcttc ttgctgg        37

<210> SEQ ID NO 66
<211> LENGTH: 42
<212> TYPE: DNA

```
<213> ORGANISM: Artificial Sequence
<220> FEATURE:
<223> OTHER INFORMATION: Synthetic Polynucleotide

<400> SEQUENCE: 66
ctctccactc tttcaccatc tatgacgcgg tcttcttgct gg                    42

<210> SEQ ID NO 67
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 67
ctctccactc tttggctatg acgcggtctt cttgctgg                         38

<210> SEQ ID NO 68
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 68
ctctccactc accatctatg acgcggtctt cttgctgg                         38

<210> SEQ ID NO 69
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 69
ctctccactc tttggaccat ctatgacgcg gtcttcttgc tgg                   43

<210> SEQ ID NO 70
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 70
ctctccactc tttggcatct atgacgcggt cttcttgctg g                     41

<210> SEQ ID NO 71
<211> LENGTH: 44
<212> TYPE: DNA
<213> ORGANISM: Macaca fascicularis

<400> SEQUENCE: 71
ctctccactc tttggcacca tctatgacgc ggtcttcttg ctgg                  44

<210> SEQ ID NO 72
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 72
ctctccactc tttcaccatc tatgacgcgg tcttcttgct gg                    42
```

```
<210> SEQ ID NO 73
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 73
ctctccactc ttttcaccat ctatgacgcg gtcttcttgc tgg          43

<210> SEQ ID NO 74
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 74
ctctccactc tttggtatga cgcggtcttc ttgctgg                 37

<210> SEQ ID NO 75
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 75
ctctccactc tttggacacc atctatgacg cggtcttctt gctgg         45

<210> SEQ ID NO 76
<211> LENGTH: 44
<212> TYPE: DNA
<213> ORGANISM: Macaca fascicularis

<400> SEQUENCE: 76
ctctccactc tttggcacca tctatgacgc ggtcttcttg ctgg          44

<210> SEQ ID NO 77
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 77
ctctccactc tttgcaccat ctatgacgcg gtcttcttgc tgg          43

<210> SEQ ID NO 78
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 78
ctctccactc tttgggacgc ggtcttcttg ctgg                    34

<210> SEQ ID NO 79
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 79
```

```
<210> SEQ ID NO 80
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 80
ctctccactc tttggatgac gcggtcttct tgctgg                                 36

<210> SEQ ID NO 81
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 81
ctctccactc tttggccacc atctatgacg cggtcttctt gctgg                       45

<210> SEQ ID NO 82
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 82
ctctccactc tttggcatct atgacgcggt cttcttgctg g                           41
```

```
ctctccactc tttggaccat ctatgacgcg gtcttcttgc tgg                         43
```

METHODS AND COMPOSITIONS FOR TREATING CONE-ROD RETINAL DYSTROPHY

CROSS-REFERENCE TO RELATED APPLICATIONS

This application is a national stage filing under 35 U.S.C. § 371 of international PCT application, PCT/US2018/048405 filed Aug. 28, 2018, which claims the benefit of the filing dates of U.S. Provisional Application No. 62/551,212 filed Aug. 28, 2017, and U.S. Provisional Application No. 62/664,063 filed Apr. 27, 2018, the entire contents of which are incorporated herein by reference.

BACKGROUND OF INVENTION

Mutations in GUCY2D, the gene encoding retinal guanylate cyclase-1 (retGC1), are the leading cause of autosomal dominant, cone-rod dystrophy (adCORD). GUCY2D-adCORD or cone-rod dystrophy type 6 (CORD6) account for 35% of adCORD cases. Patients present with a loss of visual acuity, abnormal color vision, photophobia, visual field loss and macular atrophy within the first decade. In severe cases, rod degeneration and loss of peripheral visual field follow.

SUMMARY OF THE INVENTION

Aspects of the application relate to methods of treating a subject having a cone-rod dystrophy (CORD6, e.g., autosomal dominant CORD6) by administering a first nucleic acid that encodes a guide RNA (gRNA) that targets a guanylate cyclase gene (e.g., a GUCY2D gene) sequence, and a second nucleic acid that encodes an RNA-guided endonuclease. In some embodiments, the gRNA targets both an autosomal dominant allele of GUCY2 (e.g., GUCY2D) and a wild-type allele of GUCY2 (e.g., GUCY2D) in the subject. In some embodiments, the method further comprises administering a replacement nucleic acid to the subject, wherein the replacement nucleic acid encodes a replacement functional guanylate cyclase. In some embodiments, the gRNA specifically targets an autosomal dominant allele of GUCY2 (e.g., GUCY2D) relative to a wild-type allele of GUCY2 (e.g., GUCY2D). In some embodiments, the RNA-guided endonuclease is selective for the autosomal dominant allele of GUCY2 (e.g., GUCY2D). In some embodiments, the first and second nucleic acids are administered in rAAV particles.

In some embodiments, the replacement nucleic acid is administered in an rAAV particle. In some embodiments, the replacement nucleic acid comprises a functional GUCY2 gene (e.g., a functional GUCY2 cDNA, a functional GUCY2D cDNA or other guanylate cyclase coding sequence) that is hardened relative to the gRNA. In some embodiments, the replacement nucleic acid comprises a functional GUCY2 gene that is hardened such that the gRNA no longer recognizes the gene or the RNA guided endonuclease no longer recognizes the PAM site. In some embodiments, the replacement nucleic acid comprises a functional GUCY2D gene that is hardened such that the gRNA no longer recognizes the gene or the RNA guided endonuclease no longer recognizes the PAM site.

In some embodiments, the first nucleic acid comprises a first promoter operatively connected to a gene encoding the gRNA, and wherein the first promoter is selected from the group consisting of U6, H1, opsin, rhodopsin kinase, CRX, FIZ1, CMV, CBA, EF1a, Nrl, IRBP, IRBP-GNAT2, and Cone Arrestin promoters. In some embodiments, the second nucleic acid comprises a second promoter operatively connected to a gene encoding the RNA-guided endonuclease, and wherein the second promoter is selected from the group consisting of U6, H1, opsin, rhodopsin kinase, CRX, FIZ1, CMV, CBA, EF1a, Nrl, IRBP, IRBP-GNAT2, and Cone Arrestin promoters. In some embodiments, the replacement nucleic acid comprises a replacement promoter that is operatively connected to a replacement functional GUCY2 gene (e.g., GUCY2D), and wherein the replacement promoter is selected from the group consisting of U6, H1, opsin, rhodopsin kinase, CRX, FIZ1, CMV, CBA, EF1a, Nrl, IRBP, IRBP-GNAT2, and Cone Arrestin promoters.

In some embodiments, the gRNA is encoded by a nucleic acid comprising a sequence of SEQ ID NO: 9. In some embodiments, the gRNA is encoded by a nucleic acid comprising a sequence of SEQ ID NO: 13. In some embodiments, an encoded gRNA comprises the corresponding RNA sequences to SEQ ID NO: 9 or SEQ ID NO: 13 in which Thymines (Ts) are replaced by Uracils (Us).

In some embodiments, the RNA-guided endonuclease is Cas9. In some embodiments, the selective RNA-guided endonuclease is a modified Cas9 that is selective for the autosomal dominant allele of GUCY2. In some embodiments, GUCY2 is GUCY2D.

In some embodiments, the subject has a symptom selected from the group consisting of loss of visual acuity, abnormal color vision, photophobia, visual field loss, macular atrophy, rod degeneration, loss of cones, and/or loss of peripheral visual field. In some embodiments, the replacement nucleic acid comprises a wild-type GUCY2D gene. In some embodiments, the replacement nucleic acid comprises a wild-type GUCY2D gene from a non-human primate species. In some embodiments, the rAAV capsid particles comprise rAAV capsid proteins of AAV5, AAV8, AAV9, rh10, rh8, Anc80, AAV 44.9, AAV2(triple Y-F), AAV2(quad Y-F+T-V), AAV2(MAX)deltaHS, also known as AAV2(4pMut)deltaHS. In some embodiments, the rAAV particles comprises rAAV capsid proteins of serotype 5 or serotype 8. In some embodiments, the nucleic acids and/or rAAV particles are administered intravitreally to one or both eyes of the subject. In some embodiments, the nucleic acids and/or rAAV particles are administered subretinally to one or both eyes of the subject.

Aspects of the disclosure include an rAAV particle comprising an rAAV genome, wherein the rAAV genome comprises first nucleic acid that encodes a gRNA that targets a GUCY2 (e.g., GUCY2D) gene. In some embodiments, the rAAV genome also comprises a replacement nucleic acid that encodes a functional guanylate cyclase. In some embodiments, the gRNA is specific for a dominant mutant allele of GUCY2D. In some embodiments, the rAAV capsid particles comprise rAAV capsid proteins of AAV5, AAV8, AAV9, rh10, rh8, Anc80, AAV 44.9, AAV2(triple Y-F), AAV2(quad Y-F+T-V), AAV2(MAX)deltaHS, also known as AAV2(4pMut)deltaHS. In some embodiments, the rAAV particle comprises AAV capsid proteins of serotype 5 or serotype 8. In some embodiments, the rAAV genome comprises a promoter operatively linked to a gene encoding the gRNA. In some embodiments, the promoter is selected from the group consisting of U6, H1, opsin, rhodopsin kinase, CRX, FIZ1, CMV, CBA, EF1a, Nrl, IRBP, IRBP-GNAT2, and Cone Arrestin promoters.

Aspects of the disclosure include an rAAV particle comprising an rAAV genome, wherein the rAAV genome comprises a nucleic acid that encodes a RNA-guided endonuclease that is selective for an autosomal dominant GUCY2 gene (e.g., GUCY2D). In some embodiments, the RNA-guided endonuclease is a Cas9 that is selective for an autosomal dominant GUCY2 gene (e.g., GUCY2D). In some embodiments, the rAAV capsid particles comprise rAAV capsid proteins of AAV5, AAV8, AAV9, rh10, rh8, Anc80, AAV 44.9, AAV2(triple Y-F), AAV2(quad Y-F+T-V), AAV2(MAX)deltaHS, also known as AAV2(4pMut)deltaHS. In some embodiments, the rAAV particle comprises AAV capsid proteins of serotype 5 or serotype 8. In some embodiments, the rAAV genome comprises a promoter operatively linked to a gene encoding the RNA-guided endonuclease. In some embodiments, the promoter is selected from the group consisting of U6, H1, opsin, rhodopsin kinase, CRX, FIZ1, CMV, CBA, EF1a, Nrl, IRBP, IRBP-GNAT2, and Cone Arrestin promoters. In some embodiments, the RNA-guided endonuclease is a self-inactivating RNA-guided endonuclease. In some embodiments, the nucleic acid coding the RNA-guided endonuclease is inactivated in an inducible manner. In some embodiments, the nucleic acid coding the RNA-guided endonuclease is inactivated in an inducible manner with doxycycline/tetracycline.

In some embodiments, the subject is a mammal. In some embodiments, the subject is a primate. In some embodiments, the subject is human. In some embodiments, the method reduces the severity of one or more of the following symptoms in the subject: loss of visual acuity, abnormal color vision, photophobia, visual field loss, macular atrophy, rod degeneration, loss of cones, and/or loss of peripheral visual field.

Aspects of the disclosure include an rAAV particle comprising an rAAV genome, wherein the rAAV genome comprises a nucleic acid that encodes a RNA-guided endonuclease that is selective for a GUCY2D gene, wherein the nucleic acid coding the RNA-guided endonuclease is inactivated in an inducible manner. In some embodiments, the RNA-guided endonuclease is inactivated in an inducible manner with doxycycline/tetracycline.

These and other aspects are described in more detail herein.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 10 shows a selection scheme for evolved, allele specific Cas9 and analysis of specificity in vitro for mutant versus WT allele.

FIG. 11A is a construct design for a Tet-inducible self-inactivating Cas9 system. FIG. 11B is a construct design for a dual vector Tet-inducible self-inactivating system.

FIG. 16 shows editing rates by indel sequencing.

FIGS. 17A-17F show that AAV-CRISPR/Cas9-based editing of Gucy2e in photoreceptors of the eyes of $GC1^{+/-}:GC2^{-/-}$ mice alters retinal function and structure as a consequence of reduced retGC1 expression.

FIG. 22 shows fundus images of WT mice 6 weeks post-injection with AAV-Gucy2e gRNA-hGRK1-GFP vector alone (top). Exposure and gain settings were consistent throughout.

FIG. 25 shows Sanger sequencing results in $GC1^{+/-}:GC2^{-/-}$ mice subretinally injected with AAV5-hGRK1-Cas9+AAV5-Gucy2e gRNA-hGRK1-GFP vectors. Sequences from top to bottom correspond to SEQ ID NOs: 43-63.

FIG. 26 shows Sanger sequencing results in macaques subretinally injected with AAV5-hGRK1-Cas9+AAV5-GUCY2D gRNA-hGRK1-GFP vectors. Sequences from top to bottom correspond to SEQ ID NOs: 64-82.

DETAILED DESCRIPTION OF THE INVENTION

Figure 1:
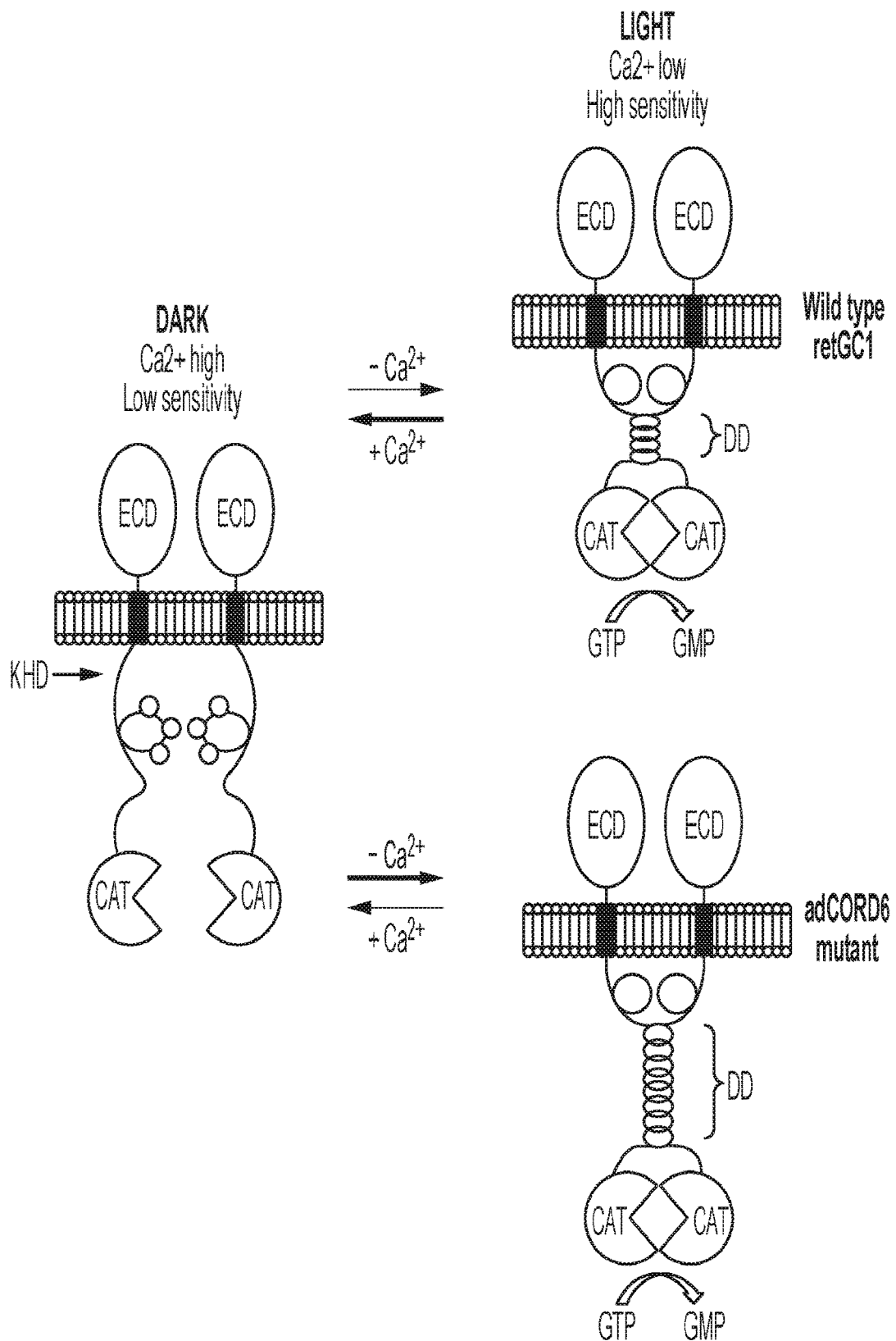
FIG. 1 shows the regulation of wildtype and R838 adCORD retGC1 in dark and light. ECD=extracellular domain; KHD=kinase homology; DD=dimerization; CAT=catalytic domains.

Provided herein are methods and compositions for treating autosomal dominant eye disorders, for example an autosomal dominant cone-rod dystrophy (e.g., CORD6). In certain embodiments, a therapeutically effective amount of a composition is administered to a subject to treat and/or prevent an autosomal dominant disorder or condition as described herein. For example, the compositions herein can be used to treat diseases or conditions associated with mutations in a GUCY2D gene.

In some embodiments, an autosomal dominant allele associated with an eye disorder (e.g., a dominant allele of the GUCY2D gene) is knocked out in one or more cells of a subject (e.g., in one or more eye cells of the subject) having an autosomal dominant eye disorder. In some embodiments, the dominant allele is specifically knocked out and the remaining functional (e.g., wild-type) allele in a heterozygous subject is sufficient for eye function (e.g., for retinal or photoreceptor function). In some embodiments, both alleles of the gene (e.g., both the dominant allele and the corresponding wild type allele in a heterozygous subject) are knocked out and a separate copy of the gene (e.g., of a wild type allele of the gene) is provided to replace the function of the alleles that were knocked out.

In some embodiments, a CRISPR-based technique is used to knock out one or both alleles of a gene associated with an eye disorder. In some embodiments, an allele-specific, CRISPR-based technique is used to specifically knock out an autosomal dominant allele of a gene of interest. In some embodiments, an allele-non-specific, CRISPR-based technique is used to knock out both alleles of a gene of interest (e.g., both the autosomal dominant allele and the wild-type allele).

In some embodiments, an allele-specific, CRISPR-based technique involves delivering an allele-specific guide RNA (gRNA) and/or an allele-specific RNA-guided endonuclease (e.g., an allele-specific Cas9 protein) to target cells (e.g., disease-affected eye cells) in a subject.

In some embodiments, an allele-non-specific, CRISPR-based technique involves delivering an allele-non-specific guide RNA (gRNA) and an allele-non-specific RNA-guided endonuclease to target cells (e.g., disease-affected eye cells) in a subject.

In some embodiments, a gRNA and/or an RNA-guided endonuclease can be delivered by delivering a first nucleic acid encoding the gRNA and a second nucleic acid encoding the RNA-guided endonuclease to a subject. In some embodiments, the first and second nucleic acids are included on the same nucleic acid molecule. In some embodiments, the first and second nucleic acid are on separate nucleic acids. In some embodiments, the first and second nucleic acids are delivered using a recombinant adeno-associated virus (rAAV). In some embodiments, both nucleic acids are included on the same rAAV genome and delivered in the same rAAV particle comprising the rAAV genome. In some embodiments, the nucleic acids are included on separate rAAV genomes and provided in different rAAV particles.

In some embodiments, an rAAV particle comprising an rAAV genome, wherein the rAAV genome comprises a nucleic acid that encodes a RNA-guided endonuclease that is selective for a GUCY2D gene, wherein the nucleic acid coding the RNA-guided endonuclease is inactivated in an inducible manner. In some embodiments, the RNA-guided endonuclease is inactivated in an inducible manner with doxycycline/tetracycline.

In some embodiments, other techniques can be used to knock out one or both alleles of a gene of interest (e.g., of GUCY2D). In some embodiments, other gene-targeting approaches (e.g., using TALENS, meganucleases, or other suitable gene-targeting techniques) can be used to knock out one or both alleles of a gene of interest. However, in some embodiments RNA-targeting approaches (e.g., using RNAi or other suitable RNA-targeting techniques) can be used to knock down or silence expression (e.g., to reduce RNA expression levels partially or completely) of one or more alleles of a target gene.

In some embodiments, when both alleles of a target gene (e.g., both GUCY2D alleles in a subject) are knocked out or knocked down in a subject, a replacement nucleic acid is provided to provide a functional variant of the target gene (e.g., a wild-type GUCY2D gene). In some embodiments, a replacement allele of a gene of interest comprises one or more nucleotide substitutions relative to the target allele(s) of the gene of interest to avoid being targeted by the gene-targeting molecules (e.g., the CRISPR gRNA and/or RNA-guided endonucleases) and/or the RNA-targeting molecules. In some embodiments, one or more (or all) of the nucleotide substitutions are silent (they don't alter the amino acid sequence of the protein encoded by the gene). In some embodiments, 1 or more, for example 2, 3, 4, 5, 6, 7, 8, 9, or 10 nucleotide substitutions are included in the replacement gene. In some embodiments, the portion of the gene in which the substitutions are made is located within the region recognized the gRNA or is within the PAM site of the Cas9 endonuclease. In some embodiments, the replacement gene or allele is referred to as a "hardened" gene or allele, because it is not targeted by the gene-targeting or RNA-targeting molecules used to knock out or knock down the target allele(s) of interest, and/or the Cas9 endonuclease (e.g., the autosomal dominant and/or wild-type alleles of GUCY2D). In some embodiments, the replacement nucleic acid comprises a functional GUCY2D gene that is hardened such that the gRNA no longer recognizes the gene or the RNA guided endonuclease no longer recognizes the PAM site.

In some embodiments, a replacement nucleic acid is delivered by administering the replacement nucleic acid to one or both eyes (e.g., to one or more cell types in one or both eyes) of a subject. In some embodiments, the replacement nucleic acid is delivered using a recombinant adeno-associated virus (rAAV) comprising an rAAV genome that includes the replacement gene of interest.

In some embodiments, the replacement nucleic acid is included on the same rAAV genome as the first and/or the second CRISPR nucleic acids (e.g., encoding the gRNA and/or RNA-guided endonuclease, respectively). In some embodiments, the RNA-guided endonuclease is a self-inactivating RNA-guided endonuclease. In some embodiments, the nucleic acid coding the RNA-guided endonuclease is inactivated in an inducible manner. In some embodiments, the nucleic acid coding the RNA-guided endonuclease is inactivated in an inducible manner with doxycycline/tetracycline.

In some embodiments, the replacement nucleic acid is included on the same rAAV genome as the first nucleic acid encoding the gRNA and both are delivered in the same rAAV particle, and the second nucleic acid encoding the RNA-guided nuclease is included on a separate rAAV genome and delivered in a different rAAV particle. In some embodiments, the replacement nucleic acid is included on the same rAAV genome as the second nucleic acid encoding the RNA-guided nuclease, and both are delivered in the same rAAV particle, and the first nucleic acid encoding the gRNA is included on a separate rAAV genome and delivered in a different rAAV particle. In some embodiments, the replacement nucleic acid, and the first and second nucleic acids (encoding the gRNA and RNA-guided nuclease, respectively) are all included on the same rAAV genome and delivered in the same rAAV particle. In some embodiments, the replacement nucleic acid, and the first and second nucleic acids are each on a different rAAV genome and delivered in a different rAAV particle.

A composition comprising one or more recombinant nucleic acids and/or rAAV particles comprising the recombinant nucleic acids (e.g., one or more of the replacement nucleic acid, the first and/or second CRISPR nucleic acids) can be delivered to target cells using any appropriate technique. In some embodiments, the composition is delivered via injection, for example via injection into one or more target loci in one or both eyes of a subject. In some embodiments, an injection is an intravitreal injection. In some embodiments, an injection is a subretinal injection. In some embodiments, an injection is a sub☐inner limiting membrane (subILM) injection (e.g., Boye S E, Alexander J J, Witherspoon C D, Boye S L, Peterson J J, Clark M E, Sandefer K J, Girkin C A, Hauswirth W W, Gamlin P D. Highly Efficient Delivery of Adeno-Associated Viral Vectors to the Primate Retina. Hum Gene Ther. 2016 August; 27(8):580-97. doi: 10.1089/hum.2016.085, incorporated herein by reference). In some embodiments, an injection is a suprachoroidal injection. In some embodiments, an injection is an intravascular injection.

In some embodiments, target cells in a subject are one or more of the following non-limiting types of eye cells, including photoreceptors, cone cells, rod cells, retinal epithelial cells, retinal bipolar cells, retinal ganglion cells and RPE cells.

In some embodiments, a subject is a patient (e.g., a human patient) that has an autosomal eye or retinal disease. Eye and retinal diseases vary widely, but most of them cause visual symptoms. Retinal diseases can affect any part of the retina. In some embodiments, a subject is a patient that has an autosomal dominant cone-rod dystrophy (e.g., CORD6). In some embodiments, a patient has one or more signs or symptoms, and methods and compositions described in this application can be used to alleviate or correct one or more of these signs or symptoms and/or restore (e.g., partially or completely) one or more aspects of normal eye function. In some embodiments, the replacement nucleic acid comprises a wild-type GUCY2D gene. In some embodiments, signs or symptoms can include one or more of loss of visual acuity, abnormal color vision, photophobia, visual field loss, macular atrophy, rod degeneration, loss of cones, and/or loss of peripheral visual field. In some embodiments, signs or symptoms can include reduced cone function. Cone function can be measured by ERG or multi-focal ERG (mfERG) or other electrophysiological testing.

Accordingly, in some embodiments aspects of the application relate to knocking out a dominant mutant form of GUCY2D. GUCY2D (e.g., NCBI Reference Sequence: NG_009092.1) encodes retinal guanylate cyclase-1 (retGC1), a protein expressed exclusively in the outer segments of photoreceptors (PRs) in the vertebrate retina (predominantly cones). Upon light stimulation, cGMP hydrolysis by cGMP phosphodiesterase (PDE) leads to closure of cGMP-gated channels, a reduction in intracellular Ca2+ and hyperpolarization of PRs. Through its activation by Ca2+-sensitive guanylate cyclase activating protein-1 (GCAP1), retGC1 plays a role in the recovery phase of phototransduction by producing cGMP within outer segments. This increase in cGMP re-opens cGMP-gated channels leading to an increase in intracellular Ca2+. Thus, the physiological link between GC1, GCAP1 and intracellular Ca2+ affects the polarization state of the PR.

Autosomal recessive, loss of function mutations in GUCY2D, can cause Leber congenital amaurosis-1 (LCA1). Subretinally delivered AAV-Gucy2e (murine homologue of GUCY2D) is capable of restoring retinal function and visually guided behavior over the long term in three different mouse models of LCA1. In contrast, autosomal dominant cone-rod dystrophy type 6 (CORD6) results from over-activity of retGC1, rather than loss of function. Its biochemical basis is as follows. The dimerization domain of wild type retGC1 is predicted to form an α-helical coiled-coil structure with four turns that are broken at residue R838. In CORD6, mutations at residue R838 are predicted to cause this structure to continue for additional turns (FIG. 1). As a result, CORD6 mutants have increased affinity for activation by GCAP1 and require much higher concentrations of Ca2+ in order to be suppressed. It is predicted that PR cell death follows due to overproduction of cGMP by the cyclase which leads to a larger influx of Ca2+ into the PR, disruption of mitochondrial outer membrane, caspase activation and ultimately apoptosis. Mutations in GUCY2D are a leading cause of adCORD, accounting for ~35% of cases. Patients present with a loss of visual acuity, abnormal color vision, photophobia, visual field loss and macular atrophy within the first decade. In severe cases, rod degeneration and loss of peripheral visual field follow loss of cones. Electroretinography reveals cone dysfunction with variable levels of rod involvement. There are no therapies currently available for treating CORD6. Notably, the vast majority of CORD6-causing mutations are located in the same residue (838).

In some embodiments, aspects of the disclosure relate to knocking out a dominant mutation in GUCY2D. In some embodiments, CORD6 can be treated using a gene editing approach and/or a gene silencing approach. In some embodiments, CORD6 can be treated using CRISPR/Cas9 as the gene editing approach. In some embodiments, CORD6 can be treated using an allele-specific gene editing approach. In some embodiments, allele-specific guide RNAs (gRNAs) and/or allele-specific Cas9 variants are used for allele specific gene editing. In some embodiments, CORD6 can be treated using an allele-non-specific gene editing approach. In some embodiments, the allele-non-specific gene editing approach also includes providing a functional replacement of GUCY2D. In some embodiments, Cas9 can be deactivated by Dox induction. In some embodiments, the Tet repressor is co-expressed from the same peptide as Cas9 (e.g., by way of a P2A self-cleaving site).

In some embodiments, one or more different recombinant viral vectors are used to deliver one or more genes encoding one or more CRISPR/Cas9 components for allele-specific gene editing. In some embodiments, one or more different recombinant viral vectors are used to deliver one or more genes encoding one or more CRISPR/Cas9 components for allele-non-specific gene editing. In some embodiments, recombinant viral vectors are used to deliver a functional replacement GUCY2D gene or a functional portion thereof.

In some embodiments, separate recombinant viral vectors are used to deliver different genes encoding different CRISPR/Cas9 components and/or a replacement gene (e.g., a hardened replacement gene). The separate recombinant viral vectors can be administered to a subject simultaneously or at different times.

In some embodiments, the recombinant viral vectors are rAAV particles comprising rAAV genomes encoding the one or more genes of interest (e.g., genes encoding gRNA, an RNA-guided nuclease, and/or a replacement gene such as a hardened replacement gene).

In some embodiments, the rAAV particles comprise wild type capsid proteins of any suitable serotype. In some embodiments, the rAAV particles comprise variant capsid proteins of any suitable serotype, wherein the variant capsid proteins comprise one or more amino acid substitutions relative to a corresponding wild-type sequence. In some embodiments, the rAAV capsid proteins are rAAVs of AAV5, AAV8, AAV9, rh10, rh8, Anc80, AAV 44.9, AAV2 (triple Y-F), AAV2(quad Y-F+T-V), AAV2(MAX)deltaHS, also known as AAV2(4pMut)deltaHS. In some embodiments, the rAAVs are of rAAV serotype 5 or rAAV serotype 8.

In some embodiments, different rAAV genomes encoding different genes of interest are provided in rAAV particles having the same serotype (or with capsid proteins having the same amino acid substitutions). However, in some embodiments different rAAV genomes encoding different genes of interest are provided in different rAAV particles (e.g., of different serotypes and/or comprising mutant capsid proteins having different amino acid substitutions).

In some embodiments, each gene of interest (e.g., the gRNA gene, the RNA-guided nuclease gene, the functional GUCY2 and/or the functional GUCY2D gene) is operably linked to a promoter. In some embodiments the genes are all under control of the same promoter. In some embodiments, each gene is under the control of a separate promoter. In some embodiments, the separate promoters are of the same type. In some embodiments, the separate promoters are different. In some embodiments, each promoter is independently selected from the group consisting of promoters that are active in one or more photoreceptor cell types. In some embodiments, a promoter is active in both rod and cones cells. In some embodiments, a promoter is rod cell specific. In some embodiments, a promoter is cone cell specific.

In some embodiments, a promoter is a human promoter (e.g., a human promoter of any of the promoter types described in this application). In some embodiments, a promoter is a non-human primate promoter (e.g., a non-human primate promoter of any of the promoter types described in this application). In some embodiments, a promoter is from another mammal (e.g., a mouse) or a non-mammalian species (e.g., a virus). In some embodiments, a promoter is a truncated natural promoter, a chimeric promoter, or a synthetic promoter.

In some embodiments, a promoter or fragment thereof is selected from the group consisting of U6 (e.g., human U6 small nuclear promoter), H1 (e.g., human H1 promoter), opsin (e.g., human opsin), rhodopsin kinase (e.g., human rhodopsin kinase), CRX (e.g., a cone-rod homeobox), FIZ1 (e.g., a FLT3 interacting zinc finger 1), CMV (e.g., a cytomegalovirus), CBA (e.g., a chicken beta actin), EF1a (e.g., an elongation factor-1 alpha), Nrl (e.g., a neural retina-specific leucine zipper protein), IRBP (e.g., an interphotoreceptor retinoid-binding protein), IRBP-GNAT2 (e.g., a chimeric promoter comprising portions of the IRBP and G protein subunit alpha transducin 2 promoter sequences), and Cone Arrestin promoters (including, for example, the corresponding human promoter sequences)

Gene Editing

Aspects of the application relate to the delivery of nucleic acids and proteins, such as genome editing nucleic acids and proteins, to target GUCY2D. In some embodiments, components of gene/genome editing are provided by AAV.

In some embodiments, one or more complexes, compositions, and/or preparations, a provided for the delivery of one or more functional effector proteins, e.g., nucleases, recombinases, and/or Cas9 proteins (including variants and fusions thereof), and/or nucleic acids (e.g., guide RNAs (gRNAs)) to a cell (e.g., in vitro or in vivo). In some embodiments, the genome editing proteins include Zinc Finger Nucleases (ZFNs), TALENs, CRISPR/Cas proteins, and/or meganucleases. In some embodiments, the cell is associated with the eye. In some embodiments, the cell is a retinal cell. In some embodiments, the biological effect exerts a therapeutic benefit to a subject in which the cell is found. In some embodiments, the complexes, compositions, preparations, systems, kits, and related methods for delivery of functional effector proteins are useful for introducing an effector protein into a cell, e.g., in the context of manipulating the cell for a research or therapeutic purpose. Delivery of site-specific proteins, such as TALENs or Cas9 proteins (or variants or fusions thereof) using the compositions, preparations, systems, kits, and related methods provided herein allows for the targeted manipulation/modification of the genome of a host cell, e.g., in GUCY2D, in vitro or in vivo.

Methods described in this application can be used to deliver proteins and/or nucleic acids into cells for a variety of purposes, such as delivery of therapeutic proteins, or genome editing. As used herein, "genome editing" refers to the adding, disrupting or changing the sequence of specific genes by insertion, removal or mutation of DNA from a genome using artificially engineered proteins and related molecules. For example, genome editing proteins, such as TALENS, may be delivered to a cell using a method described herein. The TALEN can introduce double stranded breaks at a target locus in the host cell genome, resulting in altered gene function and/or expression. TALENS can also promote DNA repair (e.g., non-homologous end joining or homology-directed repair), which is useful for rescue construct-mediated stable integration of foreign genetic material into the genome of a host cell. Rescue constructs, comprising a polynucleotide encoding a desired insertion or mutation, can be delivered before, after, or simultaneously to a genome editing protein in order to introduce a mutation or other alteration at the target locus. A rescue construct can be single-stranded polynucleotide or a double-stranded polynucleotide. In some embodiments, a rescue construct is a single-stranded oligonucleotide DNA (ssODN). In some embodiments, a rescue construct is a plasmid, viral vector, or other nucleic acid.

In some embodiments, a CRISPR/Cas9-based gene editing approach can be used. The CRISPR (clustered regularly interspaced short palindromic repeats)/Cas9 gene editing system can efficiently disrupt genes at desired loci, enabling either complete gene knockout or homology directed repair. In the former, and more commonly used system, a guide RNA (gRNA) directs the Cas9 endonuclease to specific sites in the genome proximal to a protospacer adjacent motif (PAM), causing a double-strand break (DSB). Host cell machinery efficiently repairs the DNA damage via the non-homologous end joining (NHEJ) pathway, and during this process introduce insertions or deletions (indels) at the target site. Gene disruption can thus be achieved if the target site is within the coding sequence and indels lead to frameshifts. Notably, CRISPR/Cas9 has higher targeting efficiency than other gene targeting strategies like zinc finger nucleases (ZFNs) or Transcription Activator-Like Effector Nucleases (TALENs), and is unaffected by DNA methylation status. Despite its widespread use for creating gene knockouts in vitro and in animal models, the use of CRISPR/Cas9 in retina is extremely limited. Only a handful of studies have been published to date. The first targeted a specific form of retinitis pigmentosa by evaluating the ability of electroporated gRNA- and Cas9-containing plasmids in postnatal day 0 (P0) rats to selectively ablate the dominant S334 Rhodopsin mutation. Translational limitations of this study included treatment age, and inefficiency of PR transduction with plasmid DNA. The second study used intravitreally injected AAV2 encoding gRNA and Cas9 to target the YFP locus in postmitotic ganglion cells of the Thy-1-YFP transgenic mouse. While this study provided a means to rapidly quantify CRISPR/Cas9 efficiency in vivo, it did not target a specific disease locus. The third study took a more generalized approach by asking whether phenotypic conversion of rods into cones could offer protection in the presence of rod-mediated disease. AAVs encoding gRNA and Cas9 were subretinally injected at P14 to target the rod-fate-determinant gene, neural retina leucine zipper (Nrl) in postmitotic mouse PRs. Disruption of Nrl resulted in rods assuming some cone features, and an increased resistance to death in the presence of rod-specific disease causing mutations. However, naturally occurring mutations in the NRL locus are known to cause human disease, calling into question the applicability of this approach. AAV-mediated gRNA and Cas9 were used to induce a targeted deletion in Cep290 in wild type mice. While this study demonstrated the feasibility of creating a genomic deletion in PRs, it was performed in wild type mice and thus no measurable downstream phenotype was produced.

In some embodiments of the present methods and compositions, components of CRISPR/Cas9 are provided to as subject using a recombinant AAV (rAAV) as a delivery vector.

In some embodiments, an rAAV can be used to deliver an sgRNA (single-guide RNA) that combines the tracrRNA and crRNA, which are separate molecules in the native CRISPR/Cas9 system in *S. pyogenes*, into a single RNA construct, simplifying the components needed to use CRISPR/Cas9 for genome editing (for plasmid or IVT expression).

In some embodiments, an rAAV can be used to deliver one or more genome editing proteins and/or nucleic acids that are designed to target a sequence in a gene that encodes guanylate cyclase (e.g., a GUCY2D gene, e.g., a protein coding sequence of SEQ ID NO: 7).

In some embodiments, similar methods and compositions can be adapted for treating dominant cone-rod dystrophy due to mutations in guanylate cyclase-activating protein 1 (GCAP1), the accessory protein to GC1. For example, CRISPR/Cas9 components for targeting a gene encoding GCAP1 in a subject (e.g., in a subject, such as a human subject, having one or more mutant alleles, for example a dominant allele, of a gene encoding GCAP1) can be administered to the subject (e.g., using one or more AAV vectors encoding the one or more components). In some embodiments, a replacement copy of a gene encoding a normal GCAP1 protein can be provided to the subject (e.g., using one or more AAV vectors encoding the GCAP1 protein). A non-limiting example of a GCAP1 gene is GUCAJA (see, e.g., SEQ ID NO: 8; Michaelides M, Wilkie S E, Jenkins S, Holder G E, Hunt D M, Moore A T, Webster A R, *Mutation in the gene GUCA1A, encoding guanylate cyclase-activating protein 1, causes cone, cone-rod, and macular dystrophy*, Ophthalmology 112(8):1442-7 (2005)). Guanylyl cyclase-activating protein 1 stimulates retinal guanylyl cyclase when free calcium ion concentration is low and inhibits guanylyl cyclase when free calcium ions concentration is elevated. This Ca2+-sensitive regulation of retinal guanylyl cyclase is a key event in recovery of the dark state of rod photoreceptors following light exposure. Accordingly, in some embodiments one or more genome editing proteins and/or nucleic acids are designed to target a sequence in a gene that encodes guanylate cyclase (e.g., GUCA1A, e.g., a protein coding sequence from SEQ ID NO: 8 for example).

Recombinant Adeno-Associated Virus (rAAV) Particles and Nucleic Acids

Aspects of the application relate to recombinant AAV (rAAV) particles and nucleic acids. In some embodiments, compositions comprising rAAV particles described in this application are administered to subjects having an eye disorder (e.g., an inherited eye disorder) to treat or help treat the eye disorder (for example, alone or in conjunction with one or more additional therapies).

In some embodiments, a nucleic acid is provided, the nucleic acid comprising an expression construct containing a promoter operably linked to a coding sequence of one or more genes of interest. In some embodiments, a promoter is a natural promoter. In some embodiments, a promoter can be a truncated natural promoter. In some embodiments, a promoter can include an enhancer and/or basal promoter elements from a natural promoter.

In some embodiments, an expression construct including a promoter and a gene of interest is flanked on each side by an inverted terminal repeat sequence.

Figure 7:
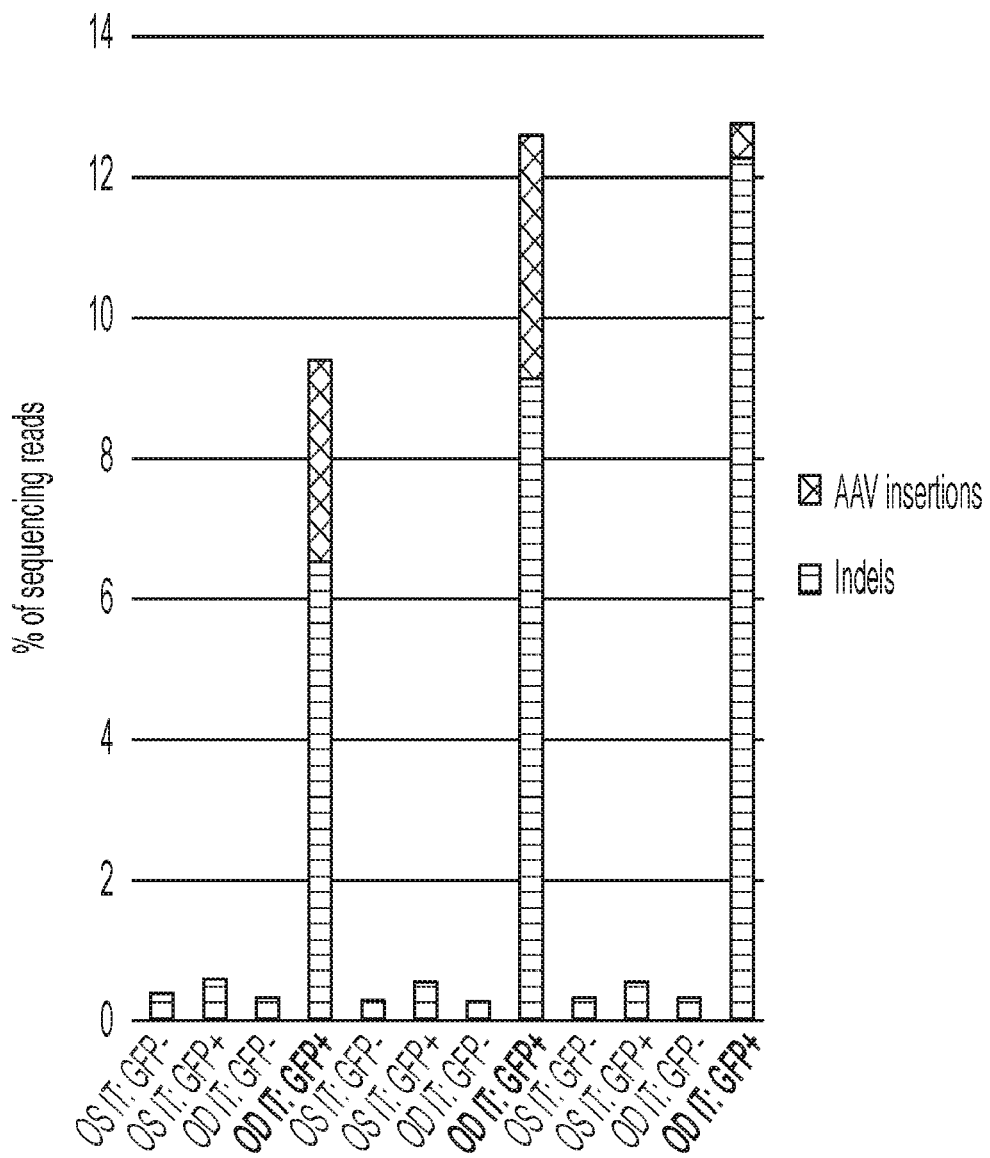
FIG. 7 shows Indel analysis in macaque cell populations. OD-right eye, OS-left eye, IT-inferior temporal retina.

In some embodiments, the expression construct comprises one or more regions comprising a sequence that facilitates expression of the coding sequence of the gene of interest, e.g., expression control sequences operably linked to the coding sequence. Non-limiting examples of expression control sequences include promoters, insulators, silencers, response elements, introns, enhancers, initiation sites, termination signals, and poly(A) tails. Any combination of such control sequences is contemplated herein (e.g., a promoter and an enhancer). In some embodiments, the expression construct includes other regulatory elements including WPRE or a miRNA target sequence (to restrict expression of the vector mediated mRNA in a tissue specific manner, for example miRNA 181c, see Kay et al. FIG. 7, *Targeting Photoreceptors via Intravitreal Delivery Using Novel, Capsid-Mutated AAV Vectors*, PLoS One, 8(4): e62097 (2013)).

In some embodiments, the nucleic acid is a plasmid (e.g., a circular nucleic acid comprising one or more of an origin of replication, a selectable marker, and a reporter gene). In some embodiments, a nucleic acid described herein, such as a plasmid, may also contain marker or reporter genes, e.g., LacZ or a fluorescent protein, and an origin of replication. In some embodiments, the plasmid is transfected into a producer cell that produces AAV particles containing the expression construct.

In some embodiments, the nucleic acid is a nucleic acid vector such as a recombinant adeno-associated virus (rAAV) genome. Exemplary rAAV nucleic acid vectors useful according to the application include single-stranded (ss) or self-complementary (sc) AAV nucleic acid vectors.

In some embodiments, a recombinant rAAV particle comprises a nucleic acid vector, such as a single-stranded (ss) or self-complementary (sc) AAV nucleic acid vector. In some embodiments, the nucleic acid vector contains an expression construct as described herein and one or more regions comprising inverted terminal repeat (ITR) sequences (e.g., wild-type ITR sequences or engineered ITR sequences) flanking the expression construct. In some embodiments, the nucleic acid is encapsidated by a viral capsid.

Accordingly, in some embodiments, a rAAV particle comprises a viral capsid and a nucleic acid vector as described herein, which is encapsidated by the viral capsid. In some embodiments, the viral capsid comprises 60 capsid protein subunits comprising VP1, VP2 and VP3. In some embodiments, the VP1, VP2, and VP3 subunits are present in the capsid at a ratio of approximately 1:1:10, respectively.

The ITR sequences of a nucleic acid or nucleic acid vector described herein can be derived from any AAV serotype (e.g., 1, 2, 3, 4, 5, 6, 7, 8, 9, or 10) or can be derived from more than one serotype. In some embodiments of the nucleic acid or nucleic acid vector provided herein, the ITR sequences are derived from AAV2. In some embodiments of the nucleic acid or nucleic acid vector provided herein, the ITR sequences are derived from one or more other serotypes. ITR sequences and plasmids containing ITR sequences are known in the art and commercially available (see, e.g., products and services available from Vector Biolabs, Philadelphia, Pa.; Cellbiolabs, San Diego, Calif.; Agilent Technologies, Santa Clara, Calif.; and Addgene, Cambridge, Mass.; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. Proc Natl Acad Sci USA. 1996 Nov. 26; 93(24):14082-7; and Curtis A. Machida. Methods in Molecular Medicine™. Viral Vectors for Gene Therapy Methods and Protocols. 10.1385/1-59259-304-6:201 © Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference).

In some embodiments, the expression construct is no more than 7 kilobases, no more than 6 kilobases, no more than 5 kilobases, no more than 4 kilobases, or no more than 3 kilobases in size. In some embodiments, the expression construct is between 4 and 7 kilobases in size.

The rAAV particle may be of any AAV serotype (e.g., 1, 2, 3, 4, 5, 6, 7, 8, 9, or 10), including any derivative (including non-naturally occurring variants of a serotype) or pseudotype.

In some embodiments, the rAAV particle is an rAAV5 particle. In some embodiments, the rAAV particle is an rAAV8 particle. In some embodiments, the rAAV particle is selected from the group consisting of rAAV2, rAAV9, rh10, rh8, and Anc80 particles. In some embodiments, the rAAV particle is an rAAV particle comprising one or more amino acid substitutions. Non-limiting examples of derivatives and pseudotypes include AAV2-AAV3 hybrid, AAVrh.10, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6 (Y445F/Y731F), AAV2.5T, AAV-HAE1/2, AAV clone 32/83, AAVShH10, AAV2 (Y→F), AAV8 (Y733F), AAV2.15, AAV2.4, AAVM41, and AAVr3.45. Such AAV serotypes and derivatives/pseudotypes, and methods of producing such derivatives/pseudotypes are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan A 1, Schaffer D V, Samulski R J.).

In some embodiments, the rAAV particles comprise capsid proteins having one or more amino acid substitutions (e.g., AAV2(tripleY-F) (Y444F+Y500F+Y730F), see Petrs-Silva et al., *Novel Properties of Tyrosine-mutant AAV2 Vectors in the Mouse Retina*, Mol. Ther. 19(2): 293-301 (2011); AAV2(quadY-F+T-V) (Y272F+Y444F+Y500F+Y730F+T491V), see Kay et al., *Targeting Photoreceptors via Intravitreal Delivery Using Novel, Capsid-Mutated AAV Vectors*, PLoS One, 8(4): e62097 (2013); or AAV2(MAX) deltaHS, also known as AAV2(4pMut)deltaHS (Y444F+Y500F+Y730F+T491V+R585S+R588T+R487G), see Boye et al., *Impact of Heparan Sulfate Binding on Transduction of Retina by Recombinant Adeno-Associated Virus Vectors*, J. Virol. 90(8): 4215-4231 (2016)).

In some embodiments, serotypes of and capsid variants include AAV5, AAV8, AAV9, rh10, rh8, Anc80, AAV 44.9 (ott.nih.gov/technology/e-175-2015), AAV2(triple Y-F), AAV2(quad Y-F+T-V), AAV2(MAX)deltaHS, also known as AAV2(4pMut)deltaHS. In some embodiments, the Cas9 and gRNA vectors are delivered in the same vectors. In some embodiments, the Cas9 and gRNA vectors are delivered in separate capsids with non-overlapping primary receptors. In some embodiments, the Cas9 and gRNA vectors are delivered in separate capsids to increase co-transduction efficiencies.

In some embodiments, the rAAV particle comprises a capsid that includes modified capsid proteins (e.g., capsid proteins comprising a modified VP3 region). Methods of producing modified capsid proteins are known in the art (see, e.g., U.S. Patent Publication Number US20130310443, which is incorporated herein by reference in its entirety). In some embodiments, the rAAV particle comprises a modified capsid protein comprising a (e.g., at least one) non-native amino acid substitution at a position that corresponds to a surface-exposed amino acid (e.g., a surface exposed Tyrosine) in a wild-type capsid protein. In some embodiments, the rAAV particle comprises a modified capsid protein comprising a non-tyrosine amino acid (e.g., a phenylalanine) at a position that corresponds to a surface-exposed tyrosine amino acid in a wild-type capsid protein, a non-threonine amino acid (e.g., a valine) at a position that corresponds to a surface-exposed threonine amino acid in the wild-type capsid protein, a non-lysine amino acid (e.g., a glutamic acid) at a position that corresponds to a surface-exposed lysine amino acid in the wild-type capsid protein, a non-serine amino acid (e.g., a valine) at a position that corresponds to a surface-exposed serine amino acid in the wild-type capsid protein, or a combination thereof.

In some embodiments, a rAAV particle (e.g., a rAAV2 or other rAAV serotype particle) comprises a capsid that includes modified capsid proteins having one or more, for example two or more (e.g., 2, 3, 4, 5, or more) amino acid substitutions.

Methods of producing rAAV particles and nucleic acid vectors are also known in the art and commercially available (see, e.g., Zolotukhin et al. *Production and purification of serotype 1, 2, and 5 recombinant adeno-associated viral vectors*. Methods 28 (2002) 158-167; and U.S. Patent Publication Numbers US20070015238 and US20120322861, which are incorporated herein by reference; and plasmids and kits available from ATCC and Cell Biolabs, Inc.). For example, the nucleic acid vector (e.g., as a plasmid) may be combined with one or more helper plasmids, e.g., that contain a rep gene (e.g., encoding Rep78, Rep68, Rep52 and Rep40) and a cap gene (encoding VP1, VP2, and VP3), and transfected into a producer cell line such that the rAAV particle can be packaged and subsequently purified.

In some embodiments, the one or more helper plasmids include a first helper plasmid comprising a rep gene and a cap gene and a second helper plasmid comprising other genes that assist in AAV production, such as a E1a gene, a E1b gene, a E4 gene, a E2a gene, and a VA gene. In some embodiments, the rep gene is a rep gene derived from AAV2 and the cap gene is derived from AAV5. Helper plasmids, and methods of making such plasmids, are known in the art and commercially available (see, e.g., pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, Pa.; Cellbiolabs, San Diego, Calif.; Agilent Technologies, Santa Clara, Calif.; and Addgene, Cambridge, Mass.; pxx6; Grimm et al. (1998), Novel Tools for Production and Purification of Recombinant Adenoassociated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081.; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188).

An exemplary, non-limiting, rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. HEK293 cells (available from ATCC®) are transfected via CaPO4-mediated transfection, lipids or polymeric molecules such as Polyethylenimine (PEI) with the helper plasmid(s) and a plasmid containing a nucleic acid vector described herein. Alternatively, in another example, Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known in the art or described herein, e.g., by iodixanol step gradient, CsCl gradient, chromatography, or polyethylene glycol (PEG) precipitation.

The disclosure also contemplates host cells that comprise at least one of the disclosed rAAV particles, expression constructs, or nucleic acid vectors. Such host cells include mammalian host cells, with human host cells being preferred, and may be either isolated, in cell or tissue culture. In the case of genetically modified animal models (e.g., a mouse), the transformed host cells may be comprised within the body of a non-human animal itself.

Compositions

Aspects of the disclosure relate to compositions comprising rAAV particles or nucleic acids described herein. In some embodiments, rAAV particles described herein are added to a composition, e.g., a pharmaceutical composition.

In some embodiments, the composition comprises a pharmaceutically acceptable carrier. The term "carrier" refers to a diluent, adjuvant, excipient, or vehicle with which the rAAV particle is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers. Non-limiting examples of pharmaceutically acceptable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, polyacrylic acids, lubricating agents (such as talc, magnesium stearate, and mineral oil), wetting agents, emulsifying agents, suspending agents, preserving agents (such as methyl-, ethyl-, and propyl-hydroxy-benzoates), and pH adjusting agents (such as inorganic and organic acids and bases). Other examples of carriers include phosphate buffered saline, HEPES-buffered saline, and water for injection, any of which may be optionally combined with one or more of calcium chloride dihydrate, disodium phosphate anhydrous, magnesium chloride hexahydrate, potassium chloride, potassium dihydrogen phosphate, sodium chloride, or sucrose. Other examples of carriers that might be used include saline (e.g., sterilized, pyrogen-free saline), saline buffers (e.g., citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers and excipients are particularly useful for delivery of rAAV particles to human subjects. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Methods for making such compositions are well known and can be found in, for example, Remington: The Science and Practice of Pharmacy, 22nd edition, Pharmaceutical Press, 2012.

Typically, such compositions may contain at least about 0.1% of the therapeutic agent (e.g., rAAV particle) or more, although the percentage of the active ingredient(s) may, of course, be varied and may conveniently be between about 1 or 2% and about 70% or 80% or more of the weight or volume of the total formulation. Naturally, the amount of therapeutic agent(s) (e.g., rAAV particle) in each therapeutically-useful composition may be prepared ins such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The term "therapeutically effective amount" as used herein refers to that amount of active composition that elicits the biological or medicinal response in a tissue, system, animal, or human that is being sought by a researcher, veterinarian, medical doctor, or other clinician. In some embodiments, a composition described herein may be administered to a subject in need thereof, such as a subject having an eye disorder such as a cone-rod retinal dystrophy. In some embodiments, a method described herein may comprise administering a composition comprising rAAV particles as described herein to a subject in need thereof. In some embodiments, the subject is a primate. In some embodiments, the subject is a human subject. In some embodiments, the subject has or is suspected of having an eye disorder. In some embodiments, the subject has been diagnosed with an eye disorder. In some embodiments, the subject is known to be at risk of having or developing an eye disorder.

Methods

Aspects of the disclosure relate to methods of delivering a nucleic acid (e.g., in an rAAV particle described herein) to a subject to treat an eye disorder. In some embodiments, a composition described herein is administered to a subject with CORD6.

In some embodiments, the method comprises administering a rAAV particle as described herein or a composition as described herein to a subject via a suitable route to treat CORD6.

In some embodiments, a subject is a mammal. In some embodiments, a subject is a human subject. In some embodiments, a subjects is a companion animal (e.g., a dog, a cat, or other companion animal). In some embodiments, a subject is a farm animal (e.g., a horse, cow, sheep, or other farm animal). However, aspects of the disclosure can be used to treat other animals (e.g., other mammals).

To "treat" a disease as the term is used herein, means to reduce the frequency or severity of at least one sign or symptom of a disease or disorder experienced by a subject. The compositions described above or elsewhere herein are typically administered to a subject in an effective amount, that is, an amount capable of producing a desirable result. The desirable result will depend upon the active agent being administered. For example, in some embodiments an effective amount of rAAV particles may be an amount of the particles that is capable of knocking-out a CORD6 mutation. In some embodiments, an effective amount of rAAV particles may be an amount of the particles that can replace one or more functions of a guanylate cyclase protein in a cell.

A therapeutically acceptable amount may be an amount that is capable of treating an eye disorder, e.g., CORD6 (e.g., alone or in combination with one or more additional therapies).

As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently.

The rAAV particle or nucleic acid vector may be delivered in the form of a composition, such as a composition comprising the active ingredient, such as a rAAV particle described herein, and a pharmaceutically acceptable carrier as described herein. The rAAV particles or nucleic acid vectors may be prepared in a variety of compositions, and may also be formulated in appropriate pharmaceutical vehicles for administration to human or animal subjects.

In some embodiments, the number of rAAV particles administered to a subject may be provided in a composition having a concentration on the order ranging from $10^6$ to $10^{14}$ particles/ml or $10^3$ to $10^{15}$ particles/ml, or any values therebetween for either range, such as for example, about $10^6$, $10^7$, $10^8$, $10^9$, $10^{10}$, $10^{11}$, $10^{12}$, $10^{13}$, or $10^{14}$ particles/ml. In one embodiment, rAAV particles of higher than $10^{13}$ particles/ml are administered. In some embodiments, the number of rAAV particles administered to a subject may be on the order ranging from 10 to 10 vector genomes(vgs)/ml or 10 to 10 vgs/ml, or any values therebetween for either range, such as for example, about $10^6$, $10^7$, $10^8$, $10^9$, $10^{10}$, $10^{11}$, $10^{12}$, $10^{13}$, or $10^{14}$ vgs/ml. In one embodiment, rAAV particles of higher than $10^{13}$ vgs/ml are administered. The rAAV particles can be administered as a single dose, or divided into two or more administrations as may be required to achieve therapy of the particular disease or disorder being treated. In some embodiments, 0.0001 ml to 10 mls are delivered to a subject. In some embodiments, the number of rAAV particles administered to a subject may be on the order ranging from $10^6$-$10^{14}$ vg/kg, or any values therebetween, such as for example, about $10^6$, $10^7$, $10^8$, $10^9$, $10^{10}$, $10^{11}$, $10^{12}$, $10^{13}$, or $10^{14}$ vgs/kg. In some embodiments, the number of rAAV particles administered to a subject may be on the order ranging from $10^{12}$-$10^{14}$ vgs/kg.

If desired, rAAV particles may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV particles may thus be delivered along with various other agents as required in the particular instance. Such compositions may be purified from host cells or other biological sources, or alternatively may be chemically synthesized. In some embodiments, the rAAV particles are delivered to the eye. In some embodiments, rAAV particles are delivered intraocularly, intravitreally, subretinally, parenterally, intravenously, intracerebro-ventricularly, or intrathecally.

The pharmaceutical forms of the rAAV particle compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, intravitreal, subretinal, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Sterile injectable solutions are prepared by incorporating the rAAV particles in the required amount in the appropriate solvent with several of the other ingredients enumerated above, as required, followed by filtered sterilization or another sterilization technique. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The amount of rAAV particle or nucleic acid vector compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the rAAV particle compositions, either over a relatively short, or a relatively prolonged period of time, as may be determined by the medical practitioner overseeing the administration of such compositions.

The composition may include rAAV particles, either alone, or in combination with one or more additional active ingredients, which may be obtained from natural or recombinant sources or chemically synthesized.

Toxicity and efficacy of the compositions utilized in methods of the disclosure can be determined by standard pharmaceutical procedures, using either cells in culture or experimental animals to determine the LD50 (the dose lethal to 50% of the population). The dose ratio between toxicity and efficacy is the therapeutic index and it can be expressed as the ratio LD50/ED50. Those compositions that exhibit large therapeutic indices are preferred. While those that exhibit toxic side effects may be used, care should be taken to design a delivery system that minimizes the potential damage of such side effects. The dosage of compositions as described herein lies generally within a range that includes an ED50 with little or no toxicity. The dosage may vary within this range depending upon the dosage form employed and the route of administration utilized.

Subjects

Aspects of the disclosure relate to methods for use with a subject, such as human or non-human primate subjects. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. In some embodiments, the subject is a human subject. Other exemplary subjects include domesticated animals (e.g., companion animals) such as dogs and cats; livestock such as horses, cattle, pigs, sheep, goats, and chickens; and other animals such as mice, rats, guinea pigs, and hamsters.

Subjects having an eye disorder; e.g., cone-rod retinal dystrophy, can be identified by a skilled medical practitioner using methods known in the art, e.g., by measuring serum concentrations of associated markers, genetic analysis, CT, PET, or MRI scans, tissue biopsies, or any combination thereof.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

AAV-CRISPR/Cas9-Based Therapies for Cone Rod Dystrophy

Clinical trials for RPE65-Leber congenital amaurosis (LCA2) have demonstrated the ability to deliver therapeutic transgene to the retinal pigment epithelium (RPE) with Adeno associated virus(AAV) thereby restoring retinal function and visually-evoked behavior to patients. This laid the groundwork for other AAV-mediated gene supplementation studies in patients with Choroideremia, Achromatopsia, Leber hereditary optic neuropathy, and X-linked Retinoschisis. Gene replacement is an effective approach for autosomal recessive disease wherein the aim is to supplement with a 'normal' gene encoding a protein missing from the patient's retina. It is ineffective, however, for addressing autosomal dominant conditions wherein gain-of-function mutations produce proteins with dominant negative effects or toxic gain of function properties. Mutations in GUCY2D, the gene encoding retinal guanylate cyclase-1 (retGC1), are the leading cause of autosomal dominant, cone-rod dystrophy (adCORD). GUCY2D-adCORD or cone-rod dystrophy type 6 (CORD6) account for 35% of adCORD cases. Patients present with a loss of visual acuity, abnormal color vision, photophobia, visual field loss and macular atrophy within the first decade. In severe cases, rod degeneration and loss of peripheral visual field follow. Significant progress has been made towards clinical application of a gene replacement therapy for LCA due to recessive mutations in GUCY2D (LCA1). However, a different approach is needed to treat CORD6 where a gain of function mutation is responsible for dysfunction and dystrophy. CRISPR/Cas9 technology has received worldwide attention as a mechanism to permanently modify disease-causing genes. Efficient knock-out retGC1 expression in mouse rods and cones, and induction a subsequent loss of retinal function using AAV-delivered CRISPR/Cas9 targeted to Gucy2e (murine homologue of GUCY2D) has been shown. In macaque, subretinal delivery of AAV-CRISPR/Cas9 reagents targeting GUCY2D also resulted in specific editing of the locus, loss of retGC1 expression and shortening of outer segments. These observations, in combination with the demonstrated success with GUCY2D gene replacement support the development of a 'knock-out+replacement' approach for treating CORD6. Notably, with rare exception, CORD6-causing mutations are confined to residue 838 of GUCY2D. Thus, CORD6 is also an ideal target for an allele-specific gene editing approach. Through directed evolution, a Cas9 has been developed with specificity for the R838S mutant allele sequence to evaluate an allele-specific AAV-CRISPR/Cas9 approach for treatment of CORD6. Through the development of clinically relevant treatments for CORD6, establish parameters for gene editing in primate retina that are applicable to other CRISPR/Cas9 therapies for treating inherited retinal disease. The preminilary data shows, the ability to efficiently edit a gene in post mitotic photoreceptors of primate with AAV-CRISPR/Cas9.

Gene replacement strategies are not suitable for treating dominantly inherited retinal dystrophies where gain of function mutations are responsible for dysfunction and dystrophy. To date, RNAi-mediated knockdown of transcripts arising from the dominant mutant gene has been successful in animal models of autosomal dominant retinitis pigmentosa. Strategies that simultaneously knock down both mutant and normal transcripts and supplement with a gene expressing a so-called 'hardened' RNA, resistant to RNAi mediated destruction are in clinical development. However, this approach relies on continuing expression of the RNAi and efficient destruction of mutant transcript. With CRISPR/Cas9 gene editing, there is now an opportunity to correct problems further upstream by 'knocking out' the underlying genetic defect. Therapeutic intervention for dominant disease can be achieved by editing both mutant and wild type alleles in conjunction with delivery of a normal, 'hardened' gene not recognized by the CRISPR/Cas9 reagents. Alternatively, if the mutational landscape is restricted to a small number, or even single nucleotide, allele specific approaches may be possible. It is hypothesized that both 'knock out+ replacement' and allele-targeted AAV-CRISPR/Cas9-based approaches can be used for the treatment of cone rod dystrophy due to autosomal dominant mutations in GUCY2D. To date, no one has successfully used AAV-mediated CRISPR/Cas9 to specifically target a disease locus and restore function/preserve structure in an animal model of inherited retinal disease. Developing the tools with which to do so is a large unmet need.

Two different mouse models of CORD6 were utilized: the recently characterized transgenic human CORD6 mice and a novel mutant CORD6 mouse. Using a Cas9 created via directed evolution to recognize the specific PAM sequence overlapping with the R838S mutation, allele specific editing in the target cell (photoreceptors) was evaluated. Because sequence immediately upstream of R838 is highly conserved between mouse and human, the ability to test clinically relevant reagents (e.g., designed against human R838S GUCY2D) is afforded for their ability to edit the endogenous locus in the heterozygous CORD6 mutant mouse.

Figure 2:
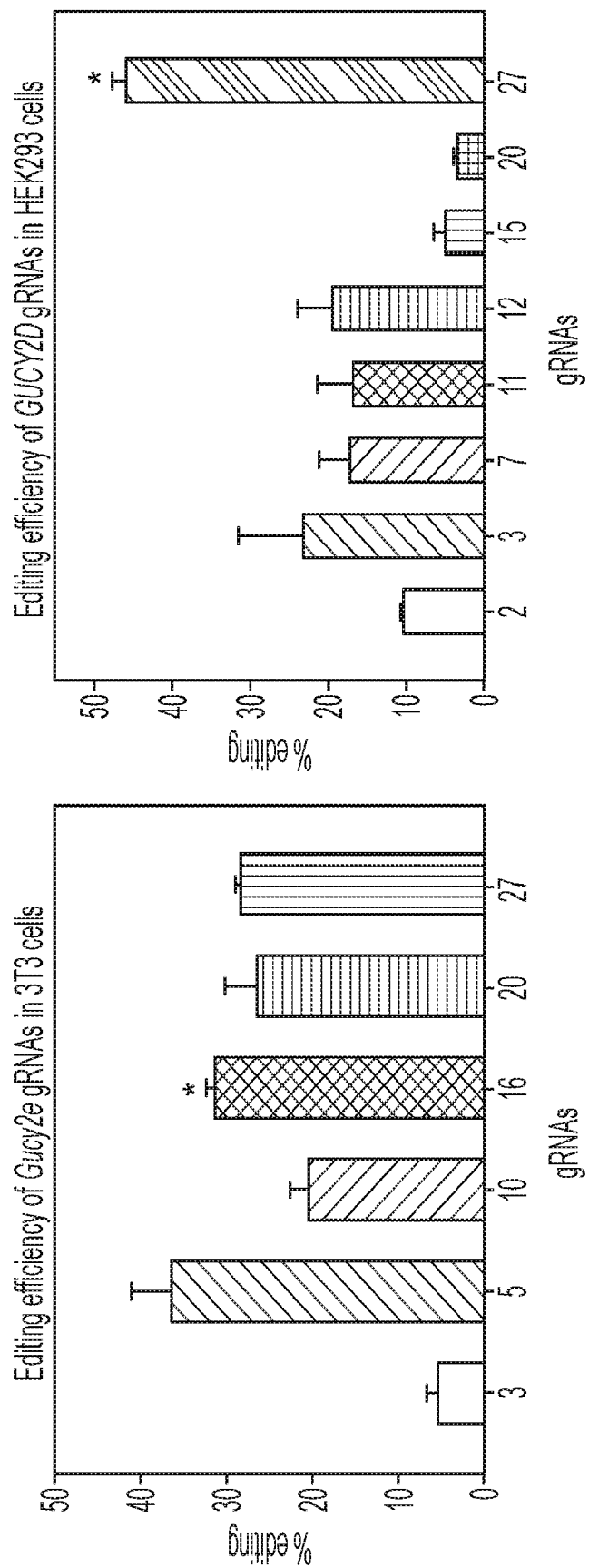
FIG. 2 shows Gucy2e and GUCY2D gRNAs screened for activity by plasmid transfection in mouse 3T3 and human HEK293 cells, respectively and indel rates determined by the T7E1 assay. GUCY2D gRNA27 has the highest editing efficiency (46% indels) in human cells, in vitro.

Development and validation of guide RNAs that efficiently direct SaCas9-mediated editing of Gucy2e and GUCY2D in-vitro. *Staphylococcus aureus* (Sa)Cas9 guide RNAs targeting the mouse Gucy2e and cynomolgus macaque (*Macaca fascicularis*)/human GUCY2D loci were selected to target the early coding sequence of the genes. Using the Cas OFFinder software[1], gRNA target sites were screened for closely matched sites containing an NNGRRN PAM in the mouse (genome build mm10) and macaque/human (genome build macFas5) genomes, respectively, and sites were prioritized based on orthogonality to the relevant genome. Guides were then screened for activity by plasmid transfection in cultured cells and indel rates determined by the T7E1 assay[2]. The most active guides were selected for in vivo use. The chosen Gucy2e gRNAs ("guide 16") had an indel rate of 35% in mouse 3T3 cells. The chosen GUCY2D gRNAs ("guide 27") had an indel rate of 46% in HEK293 cells (FIG. 2). This was validated in *M. fascicularis*, non-human primate (NHP) T cells (data not shown). Based on mismatched nucleotides at the respective homologous locations, guide 27 was not predicted to target Gucy2e and, likewise, guide 16 was not predicted to target GUC2YD. This allowed the use of the species non-specific guides as negative controls in all downstream experiments. In later in vivo experiments, the species specificity of the guides was experimentally confirmed.

AAV5-hGRK1capsid/promoter combination drives efficient SaCas9 expression in PRs. It was previously determined that AAV5 is capable of efficient rod and cone transduction following subretinal injection in mouse and primate[3]. It was also determined that the human rhodopsin kinase (hGRK1) promoter has exclusive activity in NHP rods and cones[3,4]. As such, the hGRK1 promoter was evaluated for its ability to drive Cas9 expression in mouse PRs along with two commonly used, short, ubiquitous promoters—a shortened version of the Elongation Factor Alpha (EFs) and mini Cytomegalovirus Immediate Early (miCMV). Quantitative PCR (qPCR) analysis reveal that hGRK1 was the most efficient at driving Cas9 expression in retina, and maintained specificity for PRs (data not shown). Contemporaneously, Ruan et al. similarly found that AAV5-hGRK1 drove efficient Cas9 expression in mouse retina[5]. Taken together, AAV5-hGRK1 is a suitable benchmark capsid/promoter combination for use.

Figure 13:
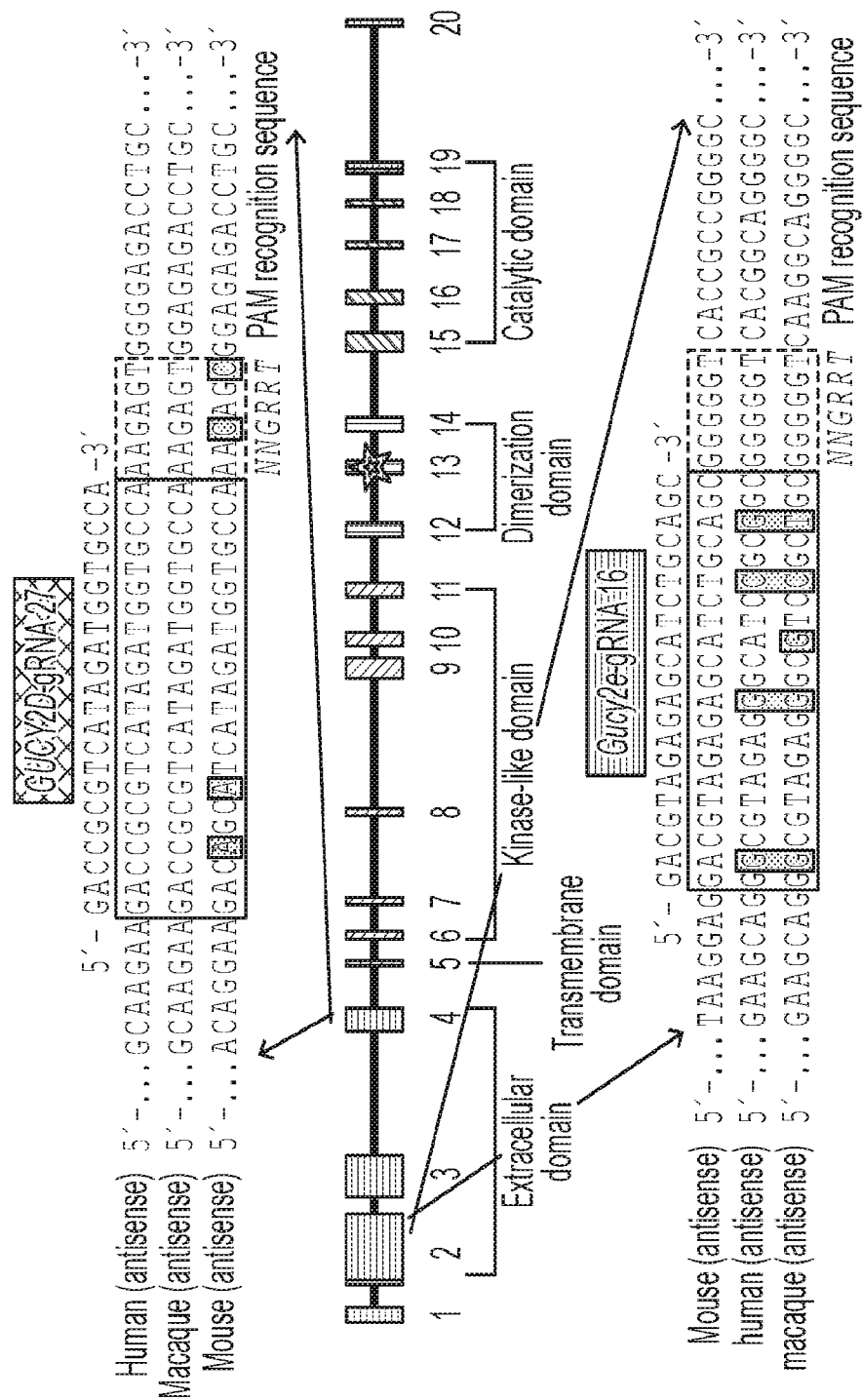
FIG. 13 shows a sequence encoding guide RNA (gRNA) 27 (SEQ ID NO: 9) and human GUCY2D gene antisense (SEQ ID NO: 10) with corresponding macaque (SEQ ID NO: 11) and mouse (SEQ ID NO: 12) gene antisense comparisons. It further shows a sequence encoding guide RNA (gRNA) 16 (SEQ ID NO: 13) and mouse Gucy2e gene antisense (SEQ ID NO: 14) with corresponding human (SEQ ID NO: 15) and macaque (SEQ ID NO: 16) gene antisense comparisons. Protospacer and PAM recognition sequences are shown in an alignment of corresponding mouse, human and macaque sequence. SEQ ID NOs: 9-16 are listed from top to bottom, respectively.
Figure 14:
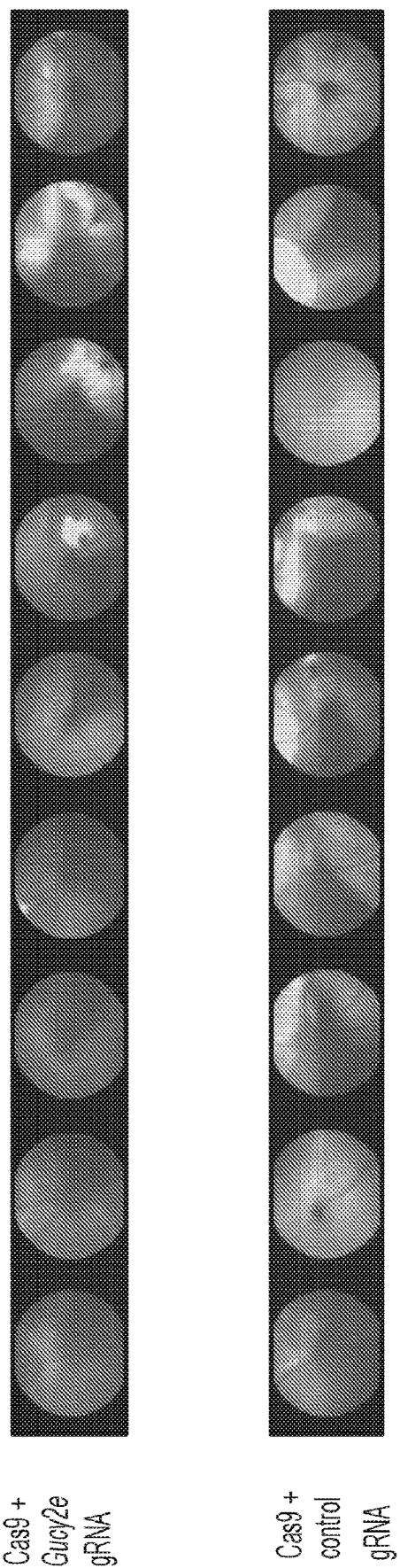
FIG. 14 shows GFP expression from the Gucy2e gRNA 16 and GUCY2D gRNA 27 vectors, respectively in subretinally injected WT mice. gRNA expression was directly correlated with success of subretinal injection, as evidenced by GFP expression in fundus images.

Human GUCY2D gene (SEQ ID NO: 10) and mouse Gucy2e gene (SEQ ID NO: 14) along with corresponding macaque, human, and mouse gene comparisons are shown in FIG. 13. Based on mismatched nucleotides at the respective homologous locations, 'guide 27' (SEQ ID NO: 9) was not predicted to target Gucy2e and, likewise, 'guide 16' (SEQ ID NO: 13) was not predicted to target GUC2YD. The nucleotide sequence encoding guide 27 and guide 16 are defined as SEQ ID Nos: 9 and 13, respectively. The corresponding transcribed RNA sequence contains uracil (U) in place of thymine (T). This allowed the use of the species non-specific guides as negative controls in all downstream experiments. In later, in vivo experiments, species specificity of the guides was experimentally confirmed. Sequences from the top to the bottom of the figure correspond to SEQ ID NOs: 9-16. As shown in FIG. 14, gRNA expression was directly correlated with success of subretinal injection, as evidenced by GFP expression in fundus images.

Figure 3A:
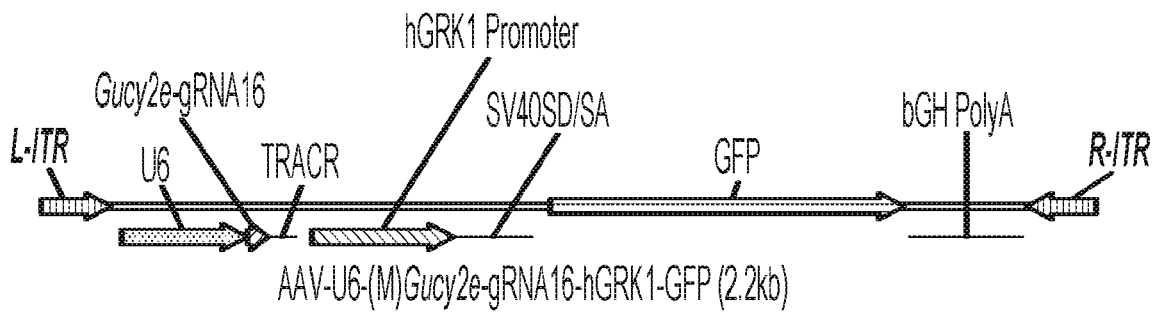
FIGS. 3A-3F show Gucy2e gRNA16- (FIG. 3A), GUCY2D gRNA27- (FIG. 3B), and SaCa9- (FIG. 3C) containing vector plasmids. Transcript analysis reveals expression of each gRNAs and Cas9 only in GFP+ cells from treated retinas of WT mice (FIG. 3D). AAV-mediated Cas9 expression was evident in WT retinas co-injected with gRNAs (FIG. 3E), but was absent from retinas treated with AAV-Cas9 alone (FIG. 3F).
Figure 3B:
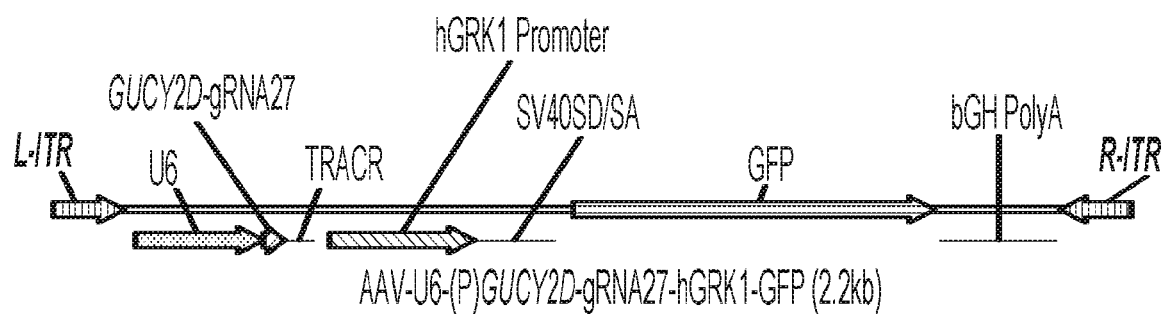
Figure 3C:
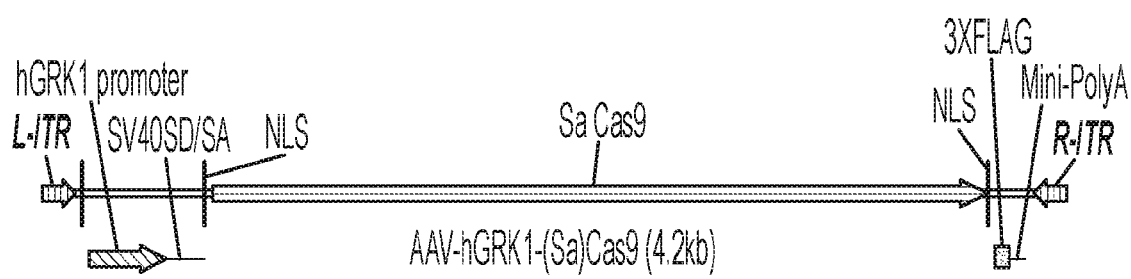
Figure 3D:
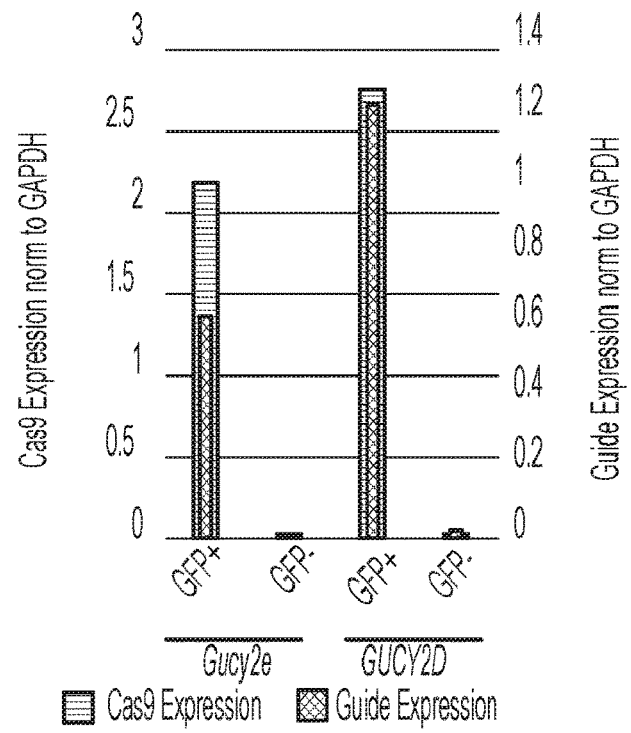
Figure 3E:
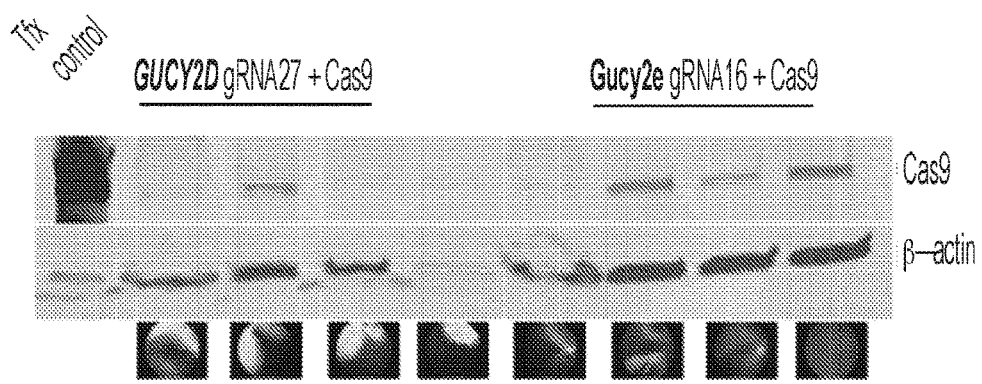
Figure 3F:
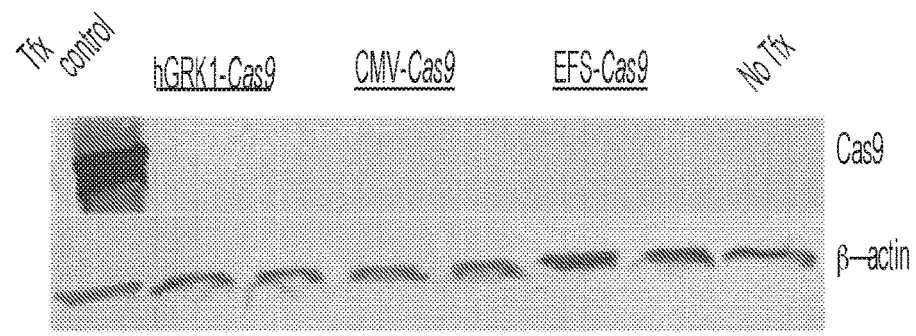

Efficient and selective editing of Gucy2e in PRs of WT mice. Next, using AAV5 vectors incorporating the most efficient gRNA identified in vitro and AAV5-hGRK1-(Sa) Cas9, gene editing experiments were carried out in vivo. Cohorts of 20, age-matched C57BL/6 mice of equal sexes were subretinally injected in their right eyes with the following two vectors—AAV5-U6-(M)Gucy2e-gRNA16-hGRK1-GFP+AAV5-hGRK1-Cas9 (FIGS. 3A and 3C). A total of 1 ul containing both vectors at a concentration of 3e12 vg/ml each (6e9 vg total) was delivered. Left eyes received AAV5-AAV5-U6-(P)GUCY2D-gRNA27-hGRK1-GFP+AAV5-hGRK1-Cas9 (FIGS. 3B and 3C). At 6 weeks post-injection, gRNA and Cas9 expression (qPCR) was evaluated, performed indel analysis, and determined whether delivery of editing reagents had an impact on retinal structure and/or function. Taking advantage of the fact that the gRNA expression vectors also contained a GFP reporter (FIGS. 3A and 3B), fluorescence activated cell sorting (FACS) was used to isolate GFP positive (GFP+) PRs and GFP negative (GFP−) cells from retinas of a subset of mice. Both RNA and DNA was extracted from these populations. QPCR analysis revealed that both gRNAs and Cas9 were expressed only in GFP+ cells (FIG. 3D). Individual retinas from a separate subset of mice were probed for Cas9 expression with western blot. Cas9 protein was detectable in retinas injected with either AAV-GUCY2D gRNA27+AAV-Cas9 or AAV-Gucy2e gRNA16+AAV-Cas9 (FIG. 3E). Different levels of Cas9 likely resulted from the variable success of subretinal injections, (see fluorescent fundus images at the bottom of each lane) (FIG. 3E). DNA extracted from both GFP+ PRs and GFP− cells was used for indel analysis to quantify and characterize gene editing. DNA from the GFP+ PRs of mice injected with AAV-Gucy2e gRNA16+AAV-Cas9 exhibited 44.8% editing at the predicted Gucy2e locus. Consistent with the qPCR expression data, DNA from the GFP− population contained no indels, confirming that editing was restricted to cells expressing the hGRK1 driven reporter (e.g., PRs that received the AAV-Gucy2e gRNA16 vector). DNA from both the GFP+ and the GFP− cells in eyes injected with control AAV-GUCY2D gRNA27+AAV-Cas9 contained no indels, confirming that GUCY2D gRNA27 does not recognize Gucy2e sequence. Despite the high rate of editing observed in AAV-Gucy2e gRNA+AAV-Cas9 injected mice, only modest declines in photopic b-wave responses were observed by ERG and no changes in retinal structure were observed by OCT (data not shown). This was expected given that C57BL/6 mice carry two copies of Gucy2e and also express Gucy2f (which encodes retGC2, a close relative of retGC1 that provides cyclase activity in rod PRs) and the short length of time mice were kept in life post-delivery of AAV-CRISPR/Cas9 reagents[6]. Notably, retinas injected with AAV5-Cas9 alone had no detectable Cas9 protein, suggesting a destabilization of the endonuclease in the absence of gRNA (FIG. 3F). This was irrespective of the promoter used to drive Cas9 (hGRK1, CMV, or EFS).

Figure 15A:
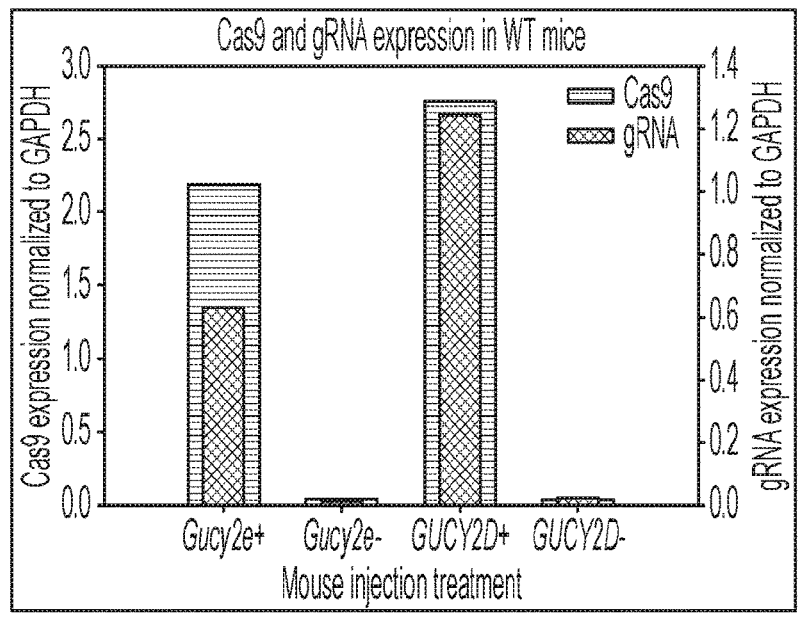
FIGS. 15A-15C show that Gucy2e-gRNA and GUCY2D-gRNA were present in GFP+ PRs of left and right eyes, respectively 6 weeks post injection in WT mice.
Figure 15B:
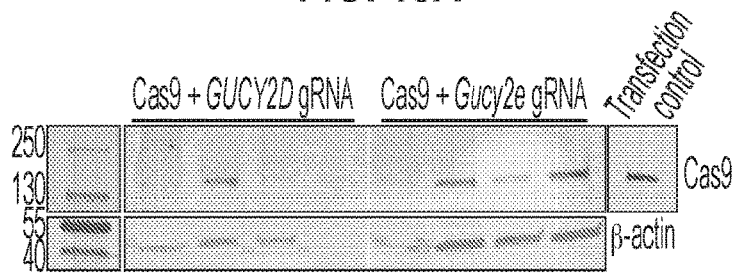
Figure 15C:
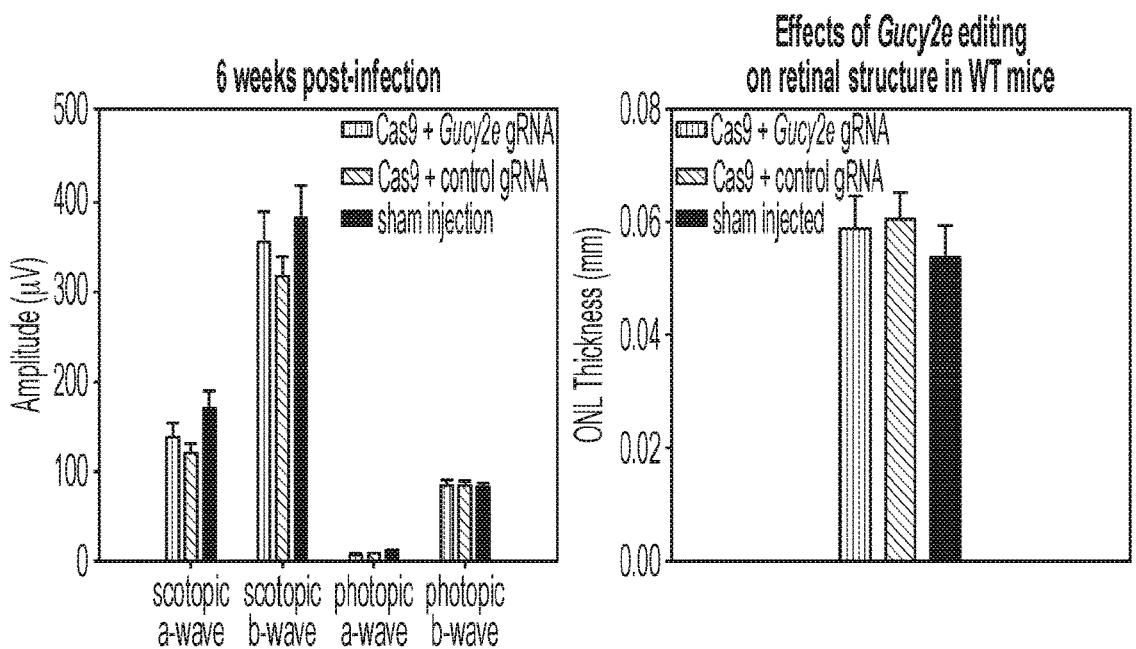

FIGS. 15A-15C show that Gucy2e-gRNA and GUCY2D-gRNA were present in GFP+ PRs of left and right eyes, respectively 6 weeks post injection (FIG. 15A). GFP− cells did not express Cas9 or gRNA. Expression of both gRNAs was slightly lower than Cas9, a result likely attributable to the different promoters driving gRNA (U6) vs. Cas9 (hGRK1). Western blot revealed Cas9 expression in retinas from eyes injected with AAV-Cas9 plus AAV-Gucy2e-gRNA (n=4) and AAV-Cas9+AAV-GUCY2D-gRNA (n=4) with expression levels varying according to the quality of subretinal injections (evidenced in fundus images of each eye taken prior to sacrifice) (FIG. 15B). This contrasts the result following injection of AAV-hGRK1-Cas9 alone and further supports that Cas9 is stabilized by the presence of gRNA. FIG. 15C shows scotopic A and B wave averages as well as photopic B wave averages in Gucy2e and GUCY2D targeted eyes. These results show that editing was only found in the cell-type targeted in the experiments.

FIG. 16 shows editing rates by indel sequencing (SEQ ID NOs: 17-32). Deep sequencing confirmed efficient Gucy2e editing in WT mice co-injected with AAV-Cas9 and AAV-Gucy2e gRNA. In GFP+ PRs from left eyes, 28.7% non-homologous end joining (NHEJ) and 16.1% AAV vector insertions were observed at the cut site for a total editing rate of 44.8%. No editing was observed in GFP− cells from left eyes, indicating the requirement for gRNA in this process. Editing of Gucy2e did not occur in either GFP+ or GFP− cells from right eyes injected with AAV-GUCY2D-gRNA+AAV-Cas9, as expected.

Figure 4A:
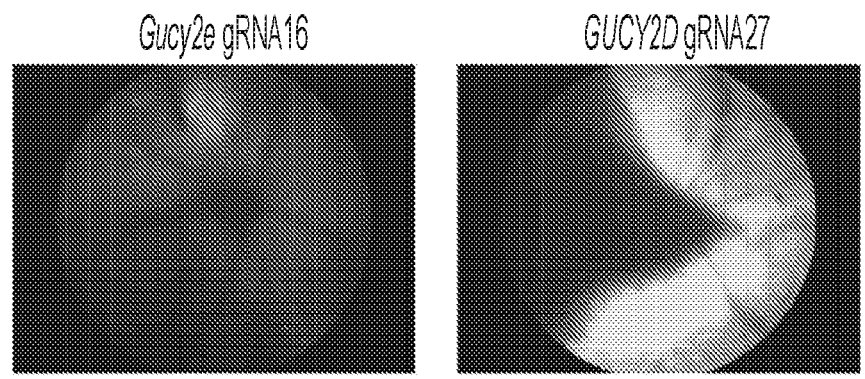
FIGS. 4A-4C show representative fundus images of GC1$^{+/-}$:GC2$^{-/-}$ mice injected with either AAV5-Gucy2e gRNA16-hGRK1-GFP or AAV5-GUCY2D gRNA27-hGRK1-GFP (FIG. 4A). ERG analysis shows a loss of both rod and cone function 6 weeks post-treatment with AAV5-Gucy2e gRNA16-hGRK1-GFP (FIGS. 4B and 4C).
Figure 4B:
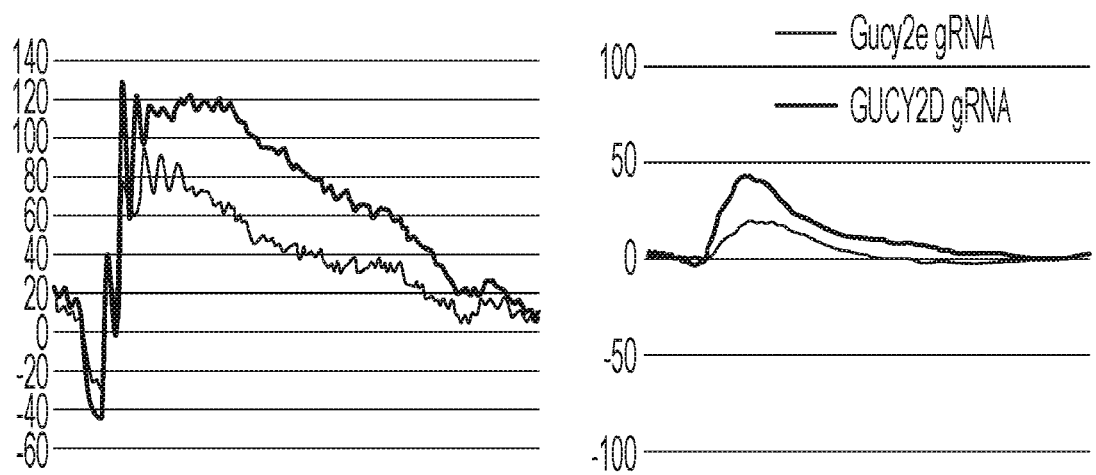
Figure 4C:
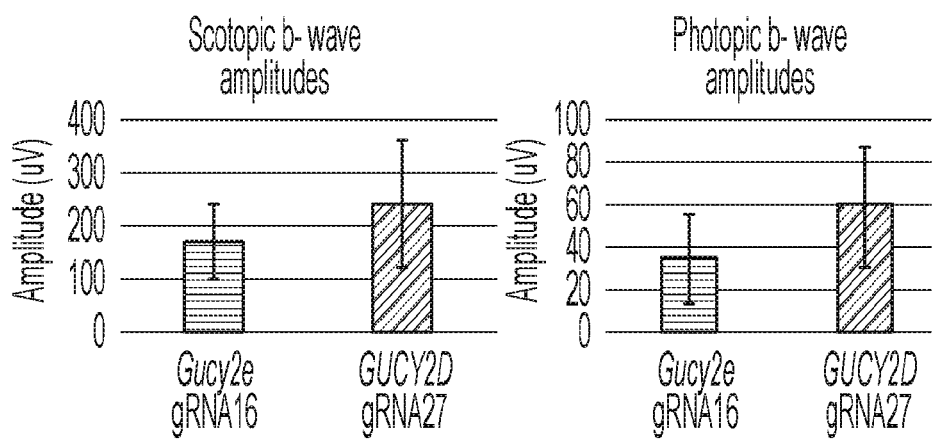
Figure 5:
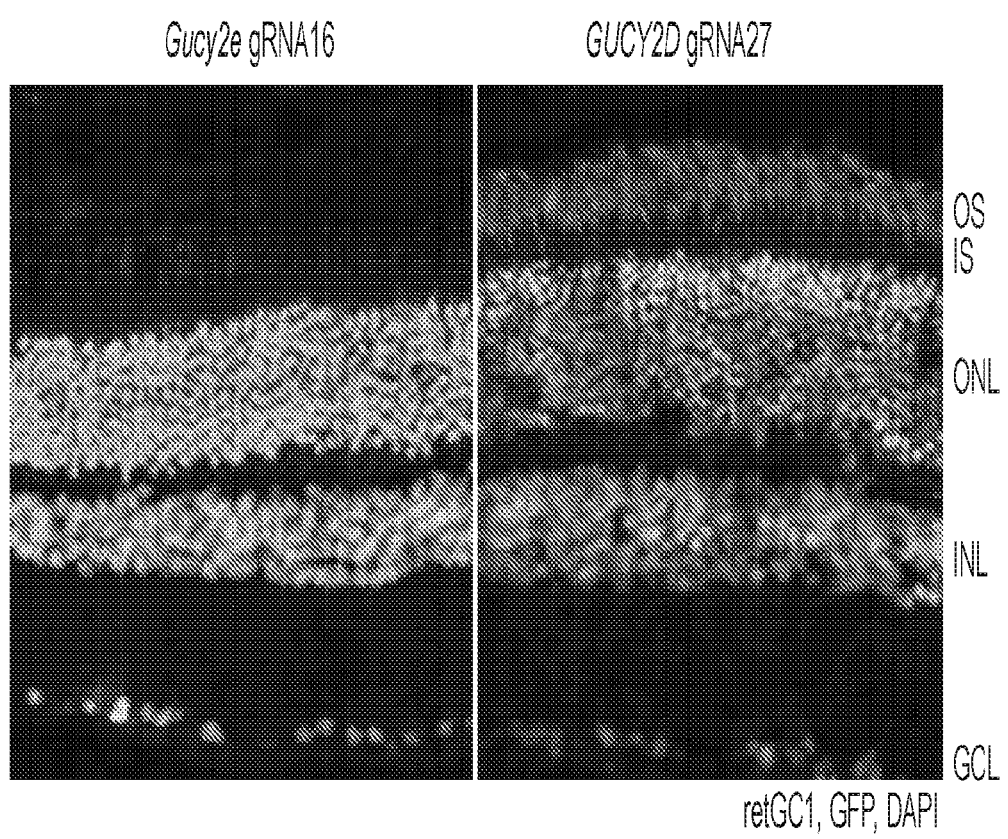
FIG. 5 shows representative retinal cross sections from GC1$^{+/-}$:GC2$^{-/-}$ mice injected with either AAV5-Gucy2e gRNA16-hGRK1-GFP or AAV5-GUCY2D gRNA27-hGRK1-GFP, and AAV5-hGRK1-Cas9. ONL—outer nuclear layer; INL—inner nuclear layer; GC1-ganglion cell layer.

Editing of Gucy2e in PRs of $GC1^{+/-}:GC2^{-/-}$ mice leads to loss of retinal function and reduction of retGC1 expression. In order to better assess whether a change in retinal phenotype could be affected by editing Gucy2e, mice carrying a single allele of Gucy2e ($GC1^{+/-}$) were generated, on a Gucy2f knock-out background (GC2−/−), i.e. "$GC1^{+/-}:GC2^{-/-}$" mice. Age matched $GC1^{+/-}:GC2^{-/-}$ mice (n=10, equal sexes) were subretinally injected in their right eyes with the same AAV5-Gucy2e gRNA16-hGRK1-GFP+AAV5-hGRK1-Cas9 vectors and dose as before. Left eyes were injected with AAV5-GUCY2D gRNA27+AAV5-hGRK1-Cas9. At 6 weeks post-injection, GFP expression was evaluated with fundoscopy (FIG. 4A), retinal function with ERG (FIGS. 4B and 4C), and retinal structure with OCT. Both rod and cone function were significantly decreased in eyes injected with AAV5-Gucy2e gRNA16+AAV-Cas9 relative to those receiving control AAV5-GUCY2D gRNA27+AAV-Cas9 (FIGS. 4B and 4C). This effect was consistent, with 9/10 injected mice displaying reduced retinal function in the AAV5-Gucy2e gRNA16+AAV5-Cas9 treated eye. No significant difference in ONL thickness was observed between right and left eyes out to 3 months post-injection (data not shown). This was expected given that mice lacking both retGC1 and retGC2 from conception (GCdKO mice) do not show appreciable ONL thinning until about 4-5 months of age[7]. Notably, retGC1 expression was profoundly reduced in PRs within the bleb of AAV5-Gucy2e gRNA16/Cas9-treated eyes (FIG. 5) whereas PRs in the control, AAV5-GUCY2D gRNA 27/Cas9-injected eye exhibited wild type-like retGC1 expression in their outer segments (FIG. 5)[8].

Figure 17A:
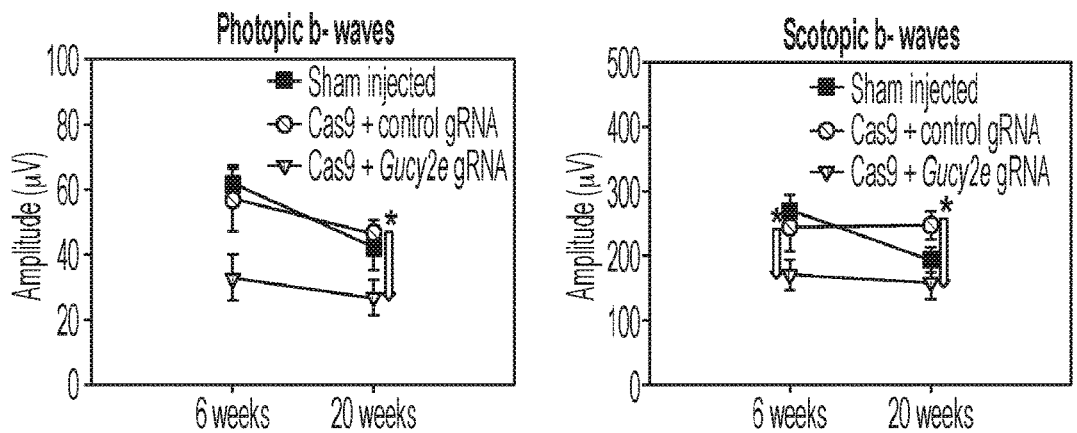
FIGS. 17A-17I show 20-weeks post-injection results for treated $GC1^{+/-}:GC2^{-/-}$ mice.
Figure 17B:
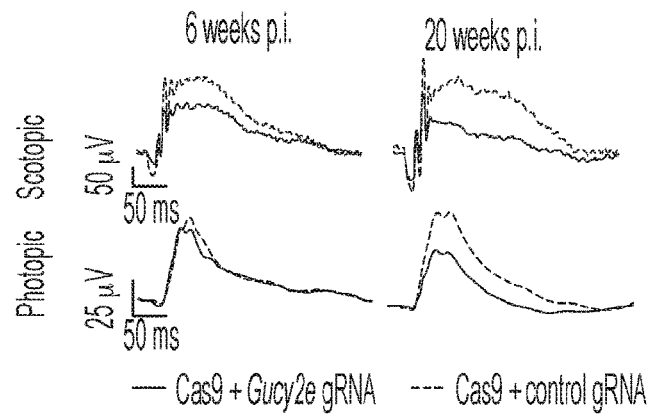
Figure 17C:
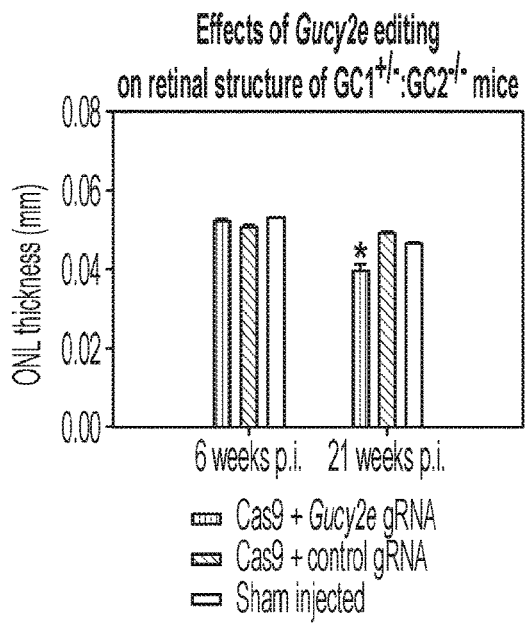
Figure 17D:
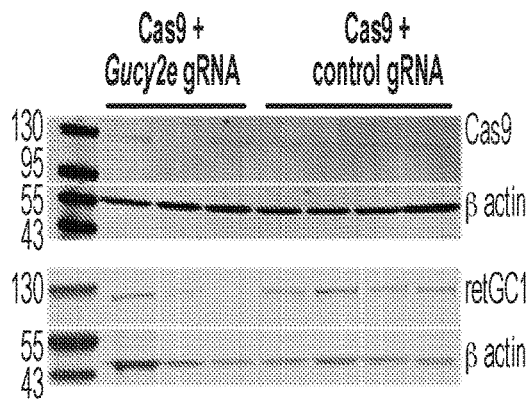
Figure 17E:
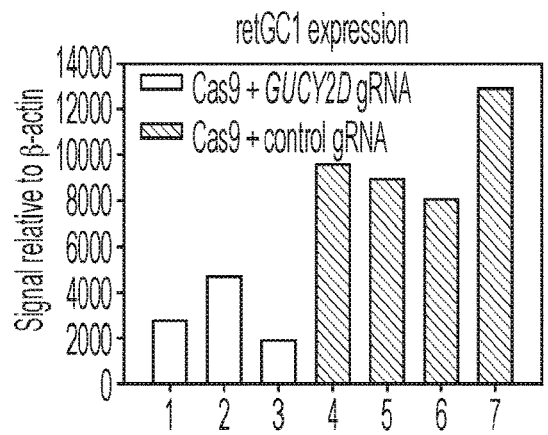
Figure 17F:
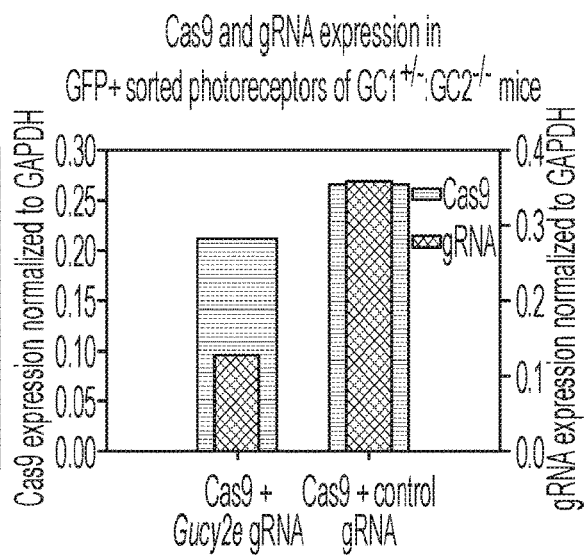
Figure 17G:
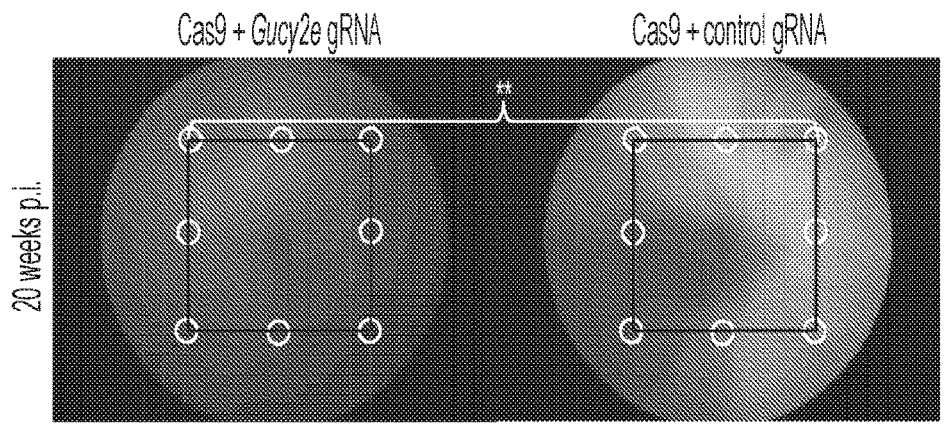
Figure 17H:
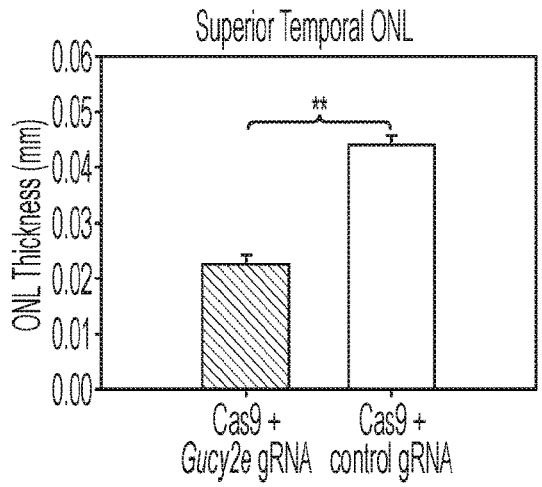
Figure 17I:
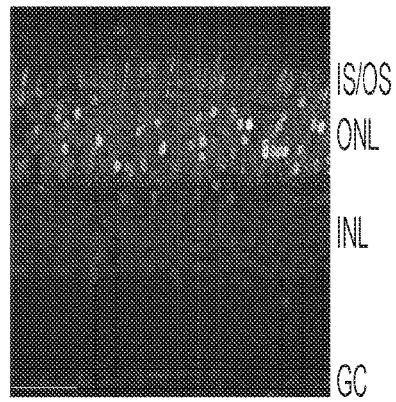

FIGS. 17A-17I show that by 20 weeks post-injection, photopic (cone-mediated) and scotopic (rod-mediated) function were significantly reduced in eyes injected with AAV-Cas9+AAV-Gucy2e gRNA relative to those injected with AAV-Cas9+AAV-orthologous gRNA control, or vehicle alone (FIGS. 17A, 17B). AAV-Cas9+AAV-orthologous gRNA control-injected eyes did not differ from vehicle-injected controls (FIG. 17A). By 20 weeks post-injection, significant loss of retinal structure was observed in Gucy2e-edited eyes relative to controls (FIG. 17C). Cas9 expression was detectable in all vector-treated eyes (FIG. 17D). retGC1 expression was reduced by ~70% in Gucy2e-edited eyes relative to eyes injected with AAV-Cas9. +AAV-orthologous gRNA control (FIG. 17D, FIG. 17E). Transcript analysis revealed both Cas9 and gRNA expression in GFP+ sorted cells from treated eyes (FIG. 17F). FIG. 17G shows average GFP pixel intensity across fundus images of treated GC1$^{+/-}$: GC2$^{-/-}$ mice performed by loading images in sequence and using the average intensity Z-projection in ImageJ. A schematic showing where the 8 locations from which ONL thickness measurements were obtained is overlaid. In the superior temporal retinas, where vector is most often deposited during subretinal injection, GFP intensity was significantly lower in Gucy2e-edited eyes at 20 weeks post-injection. ONL width in superior temporal retinas is shown in FIG. 17H. AAV5-hGRK1– mediated Cas9 expression was restricted to photoreceptors of subretinally injected GC1$^{+/-}$: GC2$^{-/-}$ mice and often colocalized with GFP expressed from the gRNA containing vector (FIG. 17I).

Figure 18A:
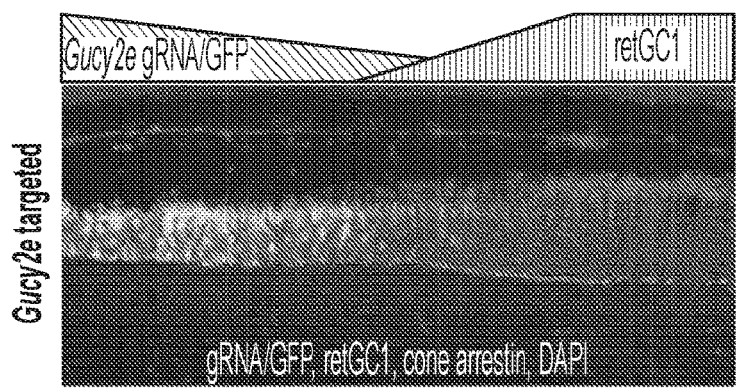
FIGS. 18A-18H show that in AAV-Gucy2e gRNA+AAV-Cas9 injected eyes, ONL thinning was restricted to the region of the GFP+ injection bleb
Figures 18B, 18C, 18D:
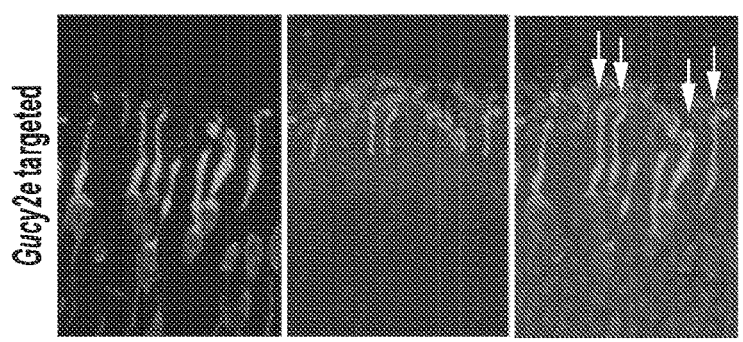
Figures 18E, 18F, 18G:
Figure 18H:
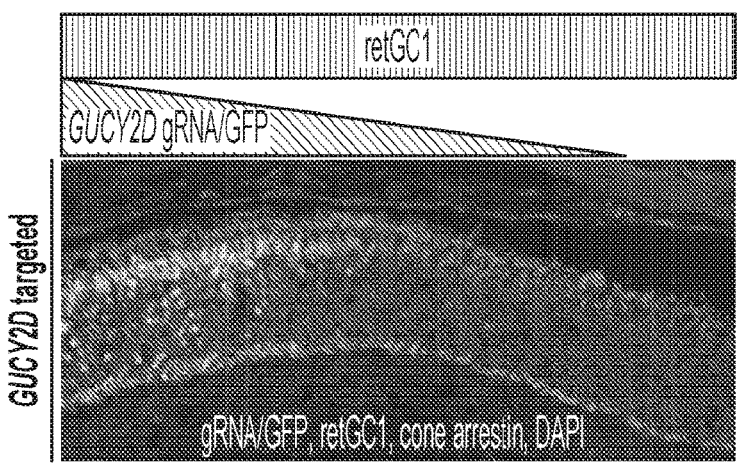

FIGS. 18A-18H show that in AAV-Gucy2e gRNA/Cas9 injected eyes, ONL thinning was restricted to the region of the GFP+ injection bleb (FIG. 18A). Loss of retGC1 in Gucy2e– targeted photoreceptors was also observed, particularly in cones, the cell type in which retGC1 expression is highest in WT mice (FIGS. 18A-18G). Cones lacking Gucy2e-gRNA (outside the bleb) exhibited clear expression of retGC1 in their outer segments (FIG. 18D, arrows) whereas cones within the bleb (those expressing Gucy2e-gRNA) lacked retGC1 signal (FIG. 18G, white arrow). Taken together, these results show that targeting early coding sequence of Gucy2e in GC1$^{+/-}$:GC2$^{-/-}$ mice results in a loss of retinal structure/function, and downregulation of retGC1. This phenotype is akin to animal models of recessive LCA1 carrying biallelic null mutations in Gucy2e. FIG. 18H shows GUCY2D targeted as a control. There were 31.5% indel reads and 4.5% AAV insertions yielding an overall editing percentage of 36%.

Editing of GUCY2D in primate PRs leads to loss of retinal structure and function, and reduction of retGC1 expression. Next, a pilot study in non-human primate (*Macaca fascicularis*) was performed to ask whether editing of the GUCY2D locus was achievable and if downstream effects on retinal structure, function and expression of retGC1 could be observed. Three macaques received subretinal injections of AAV5-U6-GUCY2D gRNA27-hGRK1-GFP+AAV5-hGRK1-Cas9 (right eyes) (FIGS. 3B and 3C) and AAVS-Gucy2e gRNA16-hGRK1-GFP+AAV5-hGRK1-Cas9 (left eyes), except for one animal who received AAV5-hGRK1-GFP, alone in its left eye (FIGS. 3A and 3C). Three subretinal blebs were created in each eye to allow for multiple downstream analyses (Table 1). It has been previously shown the ability to surgically create multiple, distinct blebs in NHP for a similar purpose[9]. Regular ophthalmological exams indicated vectors very well tolerated, with only one eye displaying mild inflammation which resolved following a short regimen of IM steroids. This eye received the Gucy2e gRNA vector and is attributed to the mild inflammation to the multiple attempts required for successful formation of one of the subretinal blebs.

Figure 6A:
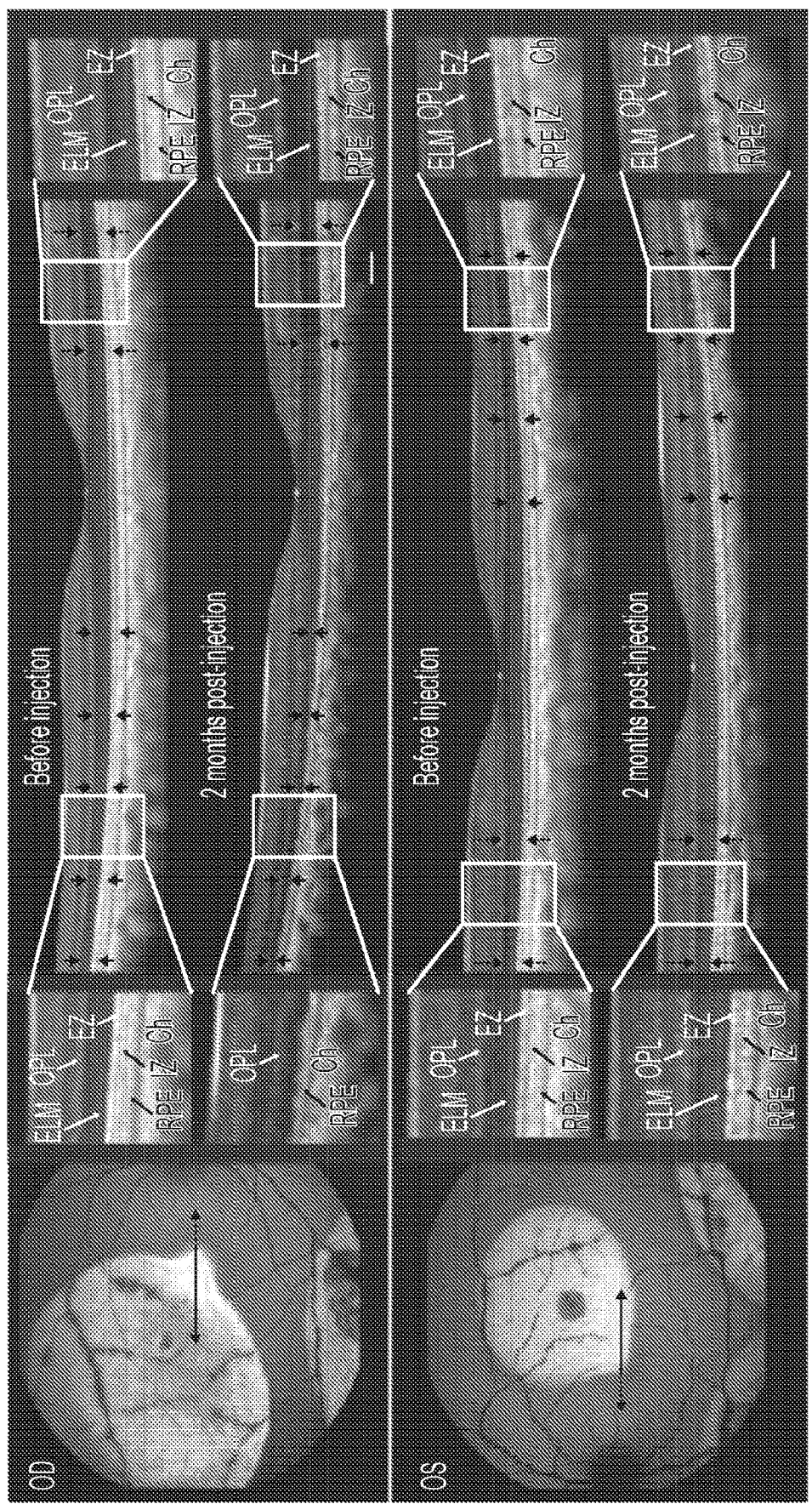
FIGS. 6A and 6B show fluorescent fundus images from macaque that reveal GFP expression in multiple blebs of AAV5-GUCY2D gRNA27-hGRK1-GFP– and AAV5-Gucy2e gRNA16-hGRK1-GFP– treated eyes (FIG. 6A). OCT scans through macular blebs and mfERG measurements from central retina are shown at baseline and 2 months post-injection.
Figure 6B:
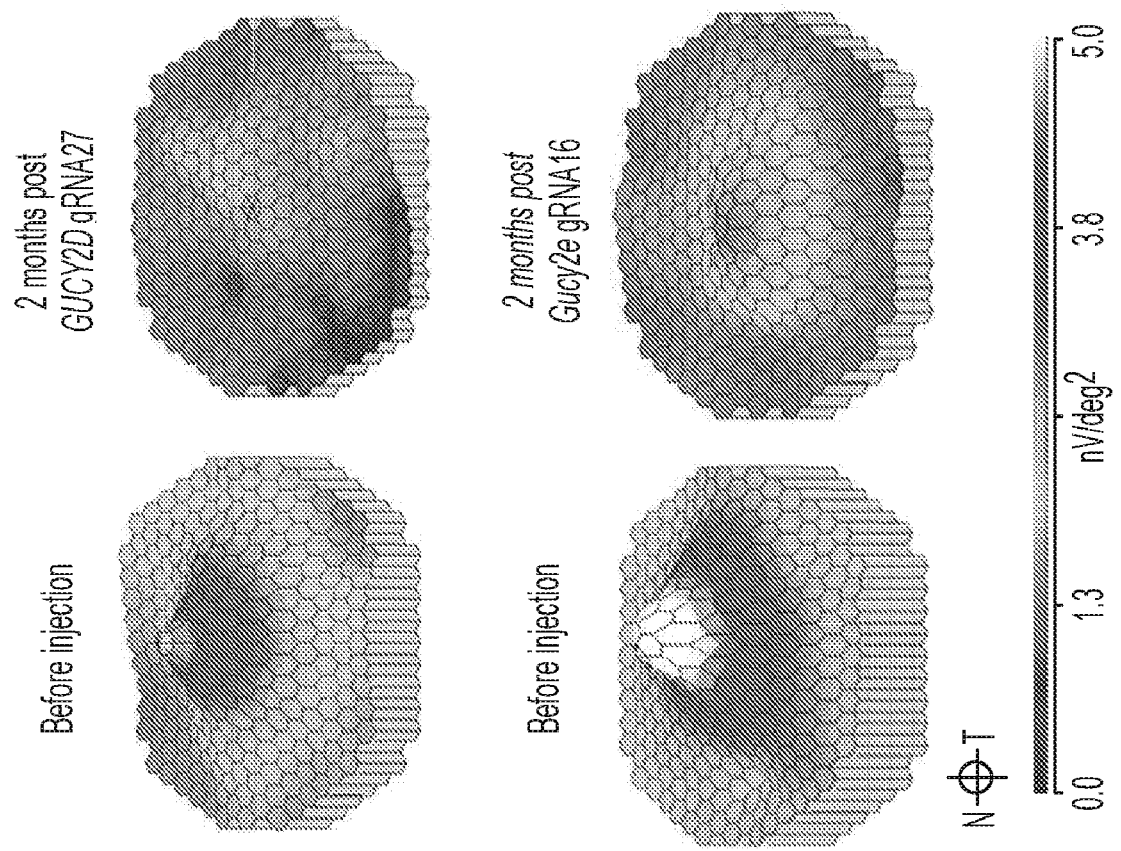
Figure 8:
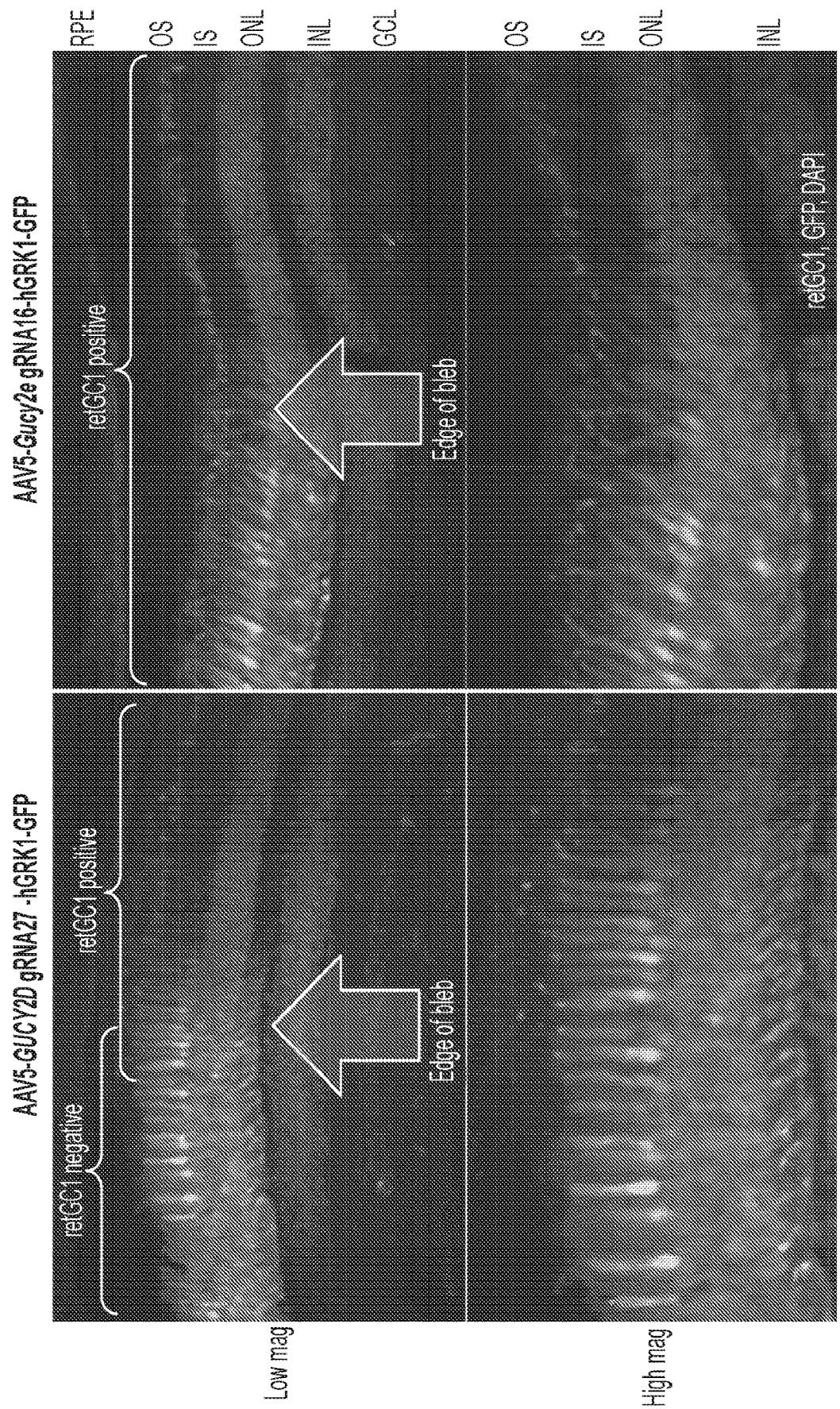
FIG. 8 shows retGC1 expression lost in photoreceptors of macaque injected with AAV5-GUCY2D gRNA27-hGRK1-GFP+AAV5-hGRK1-Cas9. Conversely, retGC1 is properly localized and expressed in AAV5-Gucy2e gRNA16-hGRK1-GFP-treated photoreceptors.

Higher power inserts of selected retinal regions in FIG. 6A show the loss in the right eye post-surgically of the ELM and photoreceptors in the injected region. At 2 months post-injection, fluorescent fundus images revealed GFP expression within all blebs of AAV-GUCY2D gRNA27/Cas9- and control treated (AAV-Gucy2e/Cas9 gRNA or AAV-GRK1-GFP)-treated eyes (FIG. 6A). OCT scans were acquired at baseline and at 2 months post-injection. Scans through macular blebs revealed shortening of PR outer segments and thinning of ONL in retinas treated with AAV-GUCY2D gRNA27/Cas9 (FIG. 6A, OD). Changes in the AAV-Gucy2e gRNA16/Cas9-treated retinas were consistent with what has been observed following subretinal injection of AAV vectors, namely disorganization of the ONL (FIG. 6A, OS). Unlike AAV-GUCY2D gRNA27/Cas9 treated eyes, PR outer segments remained relatively intact and no obvious loss of ONL was observed, with the exception being the aforementioned problematic subretinal bleb. Multifocal ERG analysis revealed a substantial decrease in central retinal function in AAV-GUCY2D gRNA27/Cas9-treated eyes (FIG. 6B). Eyes injected with AAV-Gucy2e gRNA16/Cas9 exhibit some loss of function, albeit less than that observed in AAV-GUCY2D gRNA27/Cas9-treated eyes. Inferior temporal retinal blocks from the right and left eyes of each subject were dissociated and FACS performed to separate GFP+ and GFP– populations as previously described[9]. Indel analysis was conducted on both populations and revealed that editing was restricted to the GFP+ cells from AAV-GUCY2D gRNA27/Cas9-treated retinas. The editing efficiency was similar (~10%) in all three macaques (FIG. 7). IHC analysis of retina spanning the transition region of GFP expression (e.g., the edge of the macular bleb) in the AAV-GUCY2D gRNA27/Cas9-injected retina clearly shows that cells expressing GFP, and by association the GUCY2D gRNA27, exhibit reduced retGC1 (FIG. 8). Conversely, PRs along the edge of and beyond the GFP positive area exhibit retGC1 expression in PR outer segments. PR outer segments are clearly reduced in length in the area absent retGC1 expression, confirming OCT observations. No change in retGC1 expression or OS length was observed between the treated and untreated areas of the retina receiving AAV-Gucy2e gRNA16/Cas9.

TABLE 1

Design of pilot study in non-human primate. Details from one representative subject (out of 3) are shown.

| NHP EXPERIMENTAL DESIGN | | | |
|---|---|---|---|
| OD | | OS | |
| AAV5-U6-GUCY2D gRNA27-hGRK1-GFP AAV5-hGRK1-Cas9 | | AAV5-U6-Gucy2e gRNA16-hGRK1-GFP AAV5-hGRK1-Cas9 | |
| Inferior nasal | 60 ul histology | 100 ul | histology |
| Inferior temporal | 80 ul FACS/indel analysis | 100 ul | FACS/indel analysis |
| Macular | 110 ul histology | 120 ul | histology |

OD—right eye,
OS—left eye

Figure 9:
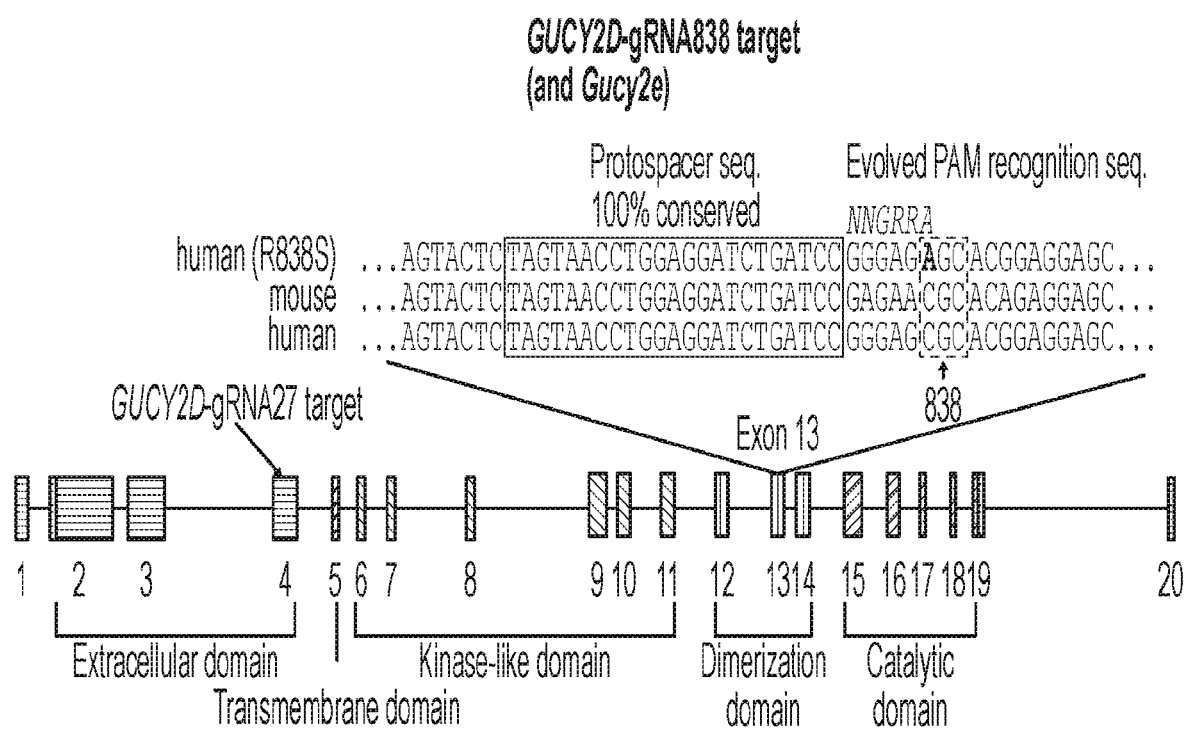
FIG. 9 shows human GUCY2D gene (SEQ ID NO: 1) with the location of gRNA targets. The protospacer and PAM recognition sequence of allele specific guide, GUCY2D-gRNA838 and evolved Cas9 are included along with an alignment of the corresponding mouse (SEQ ID NO: 2) and human (SEQ ID NO: 3) R838S mutant sequence.

Diversification and selection for SaCas9 variants that recognize PAM sequence conforming to R838S but not wildtype allele. Allele specificity of CRISPR/Cas9 editing has been explored using the prevalent single nucleotide polymorphisms that either cause or destroy PAM motifs required for selective editing[10,11]. With CORD6, most mutations occur in residue 838, with the R838S mutation being both common and highly pathogenic. Serendipitously, a consensus PAM sequence for SaCas9, NNGRR(N), is located immediately upstream of the $^{2512}$C→A transversion coding for the R838S substitution (FIG. 9). As a result a Cas9 recognizing NNGRR<u>A</u> versus NNGRR<u>C</u> would lead to allele specific editing. Using a Cas9 Scanning Mutagenesis At Random Targets (SMART) library, both positive (selection for cutting) and negative (selection against cutting) was performed using a phage based system (FIG. 10). Selection resulted in identification of three Cas9 variants that exhibit allele specificity for R838S target sequence (variant 1, 3 and 4), and another variant that exhibits higher efficiency of cleavage for the R838S target, but still leads to partial cleavage of wildtype.

Taken together, the preliminary data provide strong support for both a 'knock out+replacement' and an allele targeted approach to treat autosomal dominant GUCY2D CORD6.

Example 2

AAV-CRISPR/Cas9 Gene Editing in Human GUCY2D(R838S) Transgenic Mouse Models of CORD6

Aspects of the disclosure include determining whether ablation of human mutant R838S GUCY2D expression via CRISPR/Cas9 ameliorates loss of retinal structure and function in a transgenic model of CORD6. Utilization of a gRNA already pre-validated in human cells and in macaque to target human GUCY2D should result in editing of the transgenic human GUCY2D R838S contained within the R838S CORD6 tg mice. R838S CORD6 transgenic mice were generated by injecting mouse eggs with a construct containing human GUCY2D cDNA containing the 2512C→A transversion that codes for the R838S substitution under the control of the rod opsin promoter which restricts expression of the R838S GUCY2D mutant to rods, leaving cones as an internal control. Founders were bred to C67B6J mice for at least 4 consecutive generations to establish two separate R838S+ expressing lines. The "379" line exhibits a more gradual deterioration (arbitrarily dubbed "slower" line) and line "362", a more severe phenotype ("faster" line). By 1 month, scotopic a- and b-waves are reduced to ½ and ⅓ of normal, respectively in "379" mice. Responses to half maximal stimuli are unchanged, however, indicating that reduced function is a result of rod loss and not decreased sensitivity. By 6 months, scotopic a- and b-waves are reduced 4- and 2-fold relative to normal. Cone function remains normal in "379" mice out to 6 months (the latest time point evaluated). Loss of ONL becomes evident by 6 weeks of age, and by 3-4 months (mos), ONL thickness is reduced to half of normal. By 6 mos, only ⅓ of ONL nuclei remain. Notably, the amount of mutant R838S cyclase expressed in "379" mice is less than half that of endogenous wild type retGC1 yet this is sufficient to induce early-onset loss of retinal structure and function. Line 362 expresses at least twice the amount of mutant R838S cyclase relative to that seen in line 379, and thus exhibits more rapid deterioration. By 3.5 months, scotopic a-waves are negligible and b-waves rudimentary. Cone function is maintained at normal levels. By 3.5 mos, less than 20% of ONL remained in "362" mice, and by 5 months, this is reduced to a single layer of nuclei. The effects of gene editing in both the slow and fast transgenic lines are evaluated. Sufficient editing result in preservation of retinal structure, improvements in retinal function and a shift in Ca2+ sensitivity of the cyclase towards that of wt retGC1. In the fast-line, continued maintenance of ONL beyond the age at which all rods are lost (~5 months) would suggest that PRs, once corrected, are able to persist indefinitely, as has been recently shown in the context of recessive retinal disease.

The extent to which AAV-CRISPR/Cas9-mediated editing of GUCY2D(R838S) are determined can improve retinal function and promote preservation of PRs in human R838S CORD6 transgenic mouse models. In Experiment 1, the performance of subretinally delivered CRISPR/Cas9 reagents packaged in AAV5 is evaluated, the benchmark capsid35, and two rationally designed AAV capsids, AAV8 (dbY-F+T-V) and AAV2(4pMut)ΔHS. AAV8(dbY-F+T-V) contains two tyrosine to phenylalanine (Y-F) mutations, Y447F and Y733F and an additional threonine to valine mutation (T-V), T494V that allows the capsid to evade intracellular proteosomal mediated degradation, thereby enhancing transduction efficiency. AAV8-based capsids promote early onset of expression in retina and are particularly well suited for addressing early onset retinal degenerative models. AAV2(4pMut)ΔHS is a rationally-designed AAV2-based capsid combining two classes of mutations. The first set, three Y-F and one T-V mutations, aid in avoiding the proteosome (i.e., 4pMut). The second set ablate binding of the AAV2 capsid to heparan sulfate proteoglycan (i.e., ΔHS). This variant displays improved diffusion/enhanced lateral spread in the subretinal space and a concomitant increase in the area of retina transduced. A 1 µl subretinal injection of 5e9 vg of AAV2(4pMut)ΔHS results in the transduction of 75% of PRs as opposed to AAV5 which transduces ~30% of PRs at the same concentration. The same CRISPR/Cas9 reagents that efficiently edit GUCY2D, but not Gucy2e, are tested in both the slow and fast CORD6 tg lines. Cohorts of mice (n=30) for each line receive subretinal injections of 1 ul of a mixture of AAV-GUCY2D gRNA27-hGRK1-GFP+ AAV-hGRK1-Cas9 packaged in either AAV5, AAV8(dbY-F+T-V) or AAV2(4pMut)ΔHS in their right eyes. The concentration of each virus is the same as that used in the preliminary experiments (3e12 vg/ml). Left eyes receive AAV-hGRK1-GFP packaged in the matched capsid at a concentration of 3e12 vg/ml. The fast "362" tg line is treated at post-natal day 14 (P14) to correspond with natural eye opening and the slow "372" line are treated at P21. Injection success are determined by measuring GFP expression as assessed by fluorescent fundoscopy 1 month post injection. Retinal function and structure are evaluated by ERG and OCT, respectively at 1, 2, 4, 6 and 12 months post-injection. Retinas from a subset of mice are harvested, dissociated, sorted via FACS and DNA extracted for determination of editing efficiencies using the same methodology described in the preliminary data. The nature of sequence insertions at cut sights were investigated as previously observed a high frequency of vector sequence integration that incorporates one of the ITRs (FIG. 7). At 3-6 months post-treatment (may vary depending on mouse line), subsets of mice are sent to Salus University for biochemical analysis of guanylate cyclase function (e.g., retGC activity assay). Additional mice are sacrificed at interim time points for immunohistochemistry (IHC) and western blot (WB) to evaluate the localization and relative expression of retGC1, GCAP1, and other PR proteins of interest. The amount of GFP positive PRs remaining in GUCY2D-gRNA27 versus contralateral GFP only treated eyes is quantified. It is expected that the majority of PRs remaining in GUCY2D-gRNA27-treated eyes are GFP positive. In Experiment 2 gene editing in the same two mouse lines are evaluated following intravitreal delivery of the CRISPR/Cas9 reagents packaged in a novel AAV capsid, "M3-B(Y-F+T-V)" that was mined via directed evolution in NHP and displays highly efficient PR transduction following Ivt delivery relative to benchmark vectors. The same series of outcome measures outlined in Experiment 1 are performed on these mice, including quantification of gene editing and transduction efficiency, evaluation of retinal structure and function, biochemical analysis of guanylate cyclase activity, and IHC/WB for localization and characterization of proteins of interest.

Figure 19A:
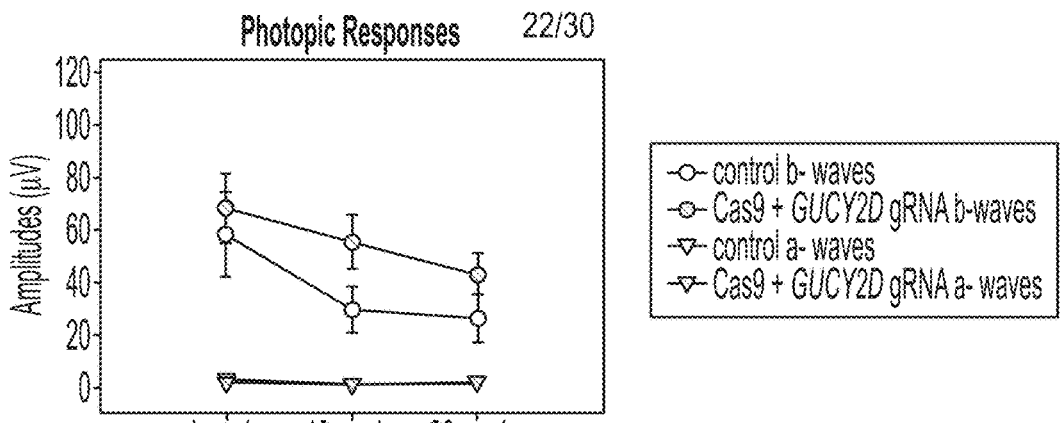
FIGS. 19A-19D show 10 week post-injection results for GUCY2D editing in GUCY2D(R838S) transgenic mice.
Figure 19B:
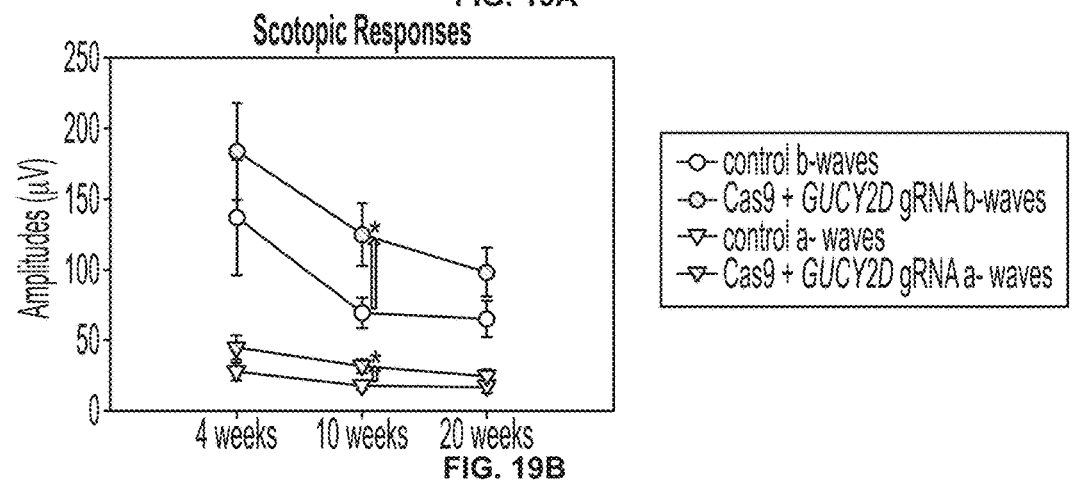
Figure 19C:
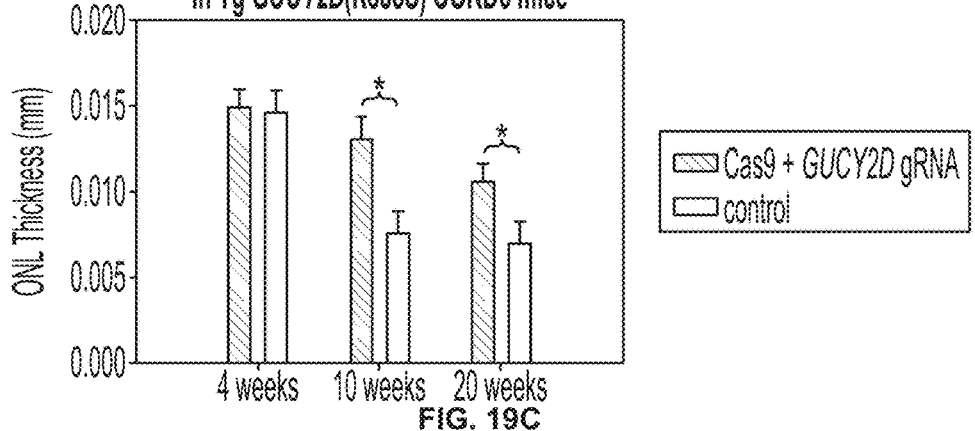
Figure 19D:
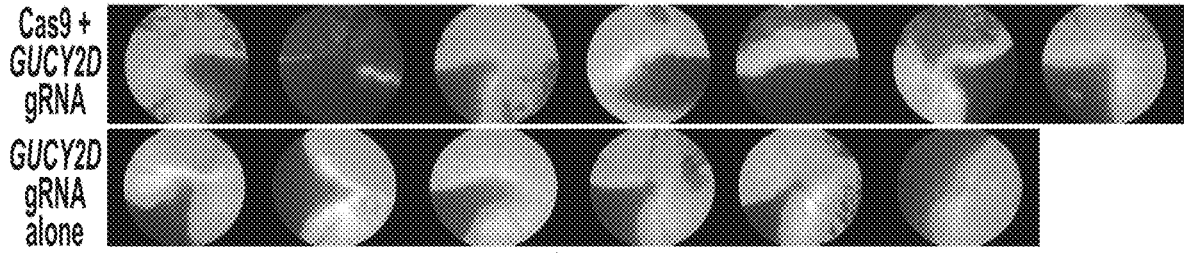

FIGS. 19A-19D show 10 week post-injection results for GUCY2D editing in R838S transgenic mice. AAV-CRISPR/Cas9-based editing of GUCY2D is therapeutic in a transgenic mouse model of R838S CORD6. By 10 weeks post-injection, scotopic (rod-mediated) function was significantly improved in eyes injected with AAV-Cas9+AAV-GUCY2D gRNA relative to those injected with AAV-Cas9+AAV-orthologous gRNA control (FIGS. 19A, 19B). Significant preservation of retinal structure was also observed in GUCY2D-edited eyes relative to controls (FIG. 19C). FIG. 19D shows fundus images of R838S CORD6 mice 6 weeks post-injection with either AAV-Cas9+AAV-GUCY2D gRNA vectors, or AAV-GUCY2D gRNA alone. Exposure and gain settings were consistent throughout.

Example 3

Clinically Applicable CRISPR/Cas9 Gene Editing Approaches for the Treatment of CORD6

'Knock-out and replacement' of GUCY2D or allele-specific editing of R838S GUCY2D in conjunction with the development of a self-inactivating Cas9. While evaluating the impact of knocking out GUCY2D(R838S) expression using CRISPR/Cas9 in the R838S CORD6 tg mice address the question of whether remaining PR cells persist once the underlying gain of function mutation is nullified, the approach is not immediately translatable. Here, two independent approaches were developed for the treatment of CORD6 that rely on editing of GUCY2D and are clinically translatable. The first hurdle to translation was to address the issue of persistent Cas9 expression. While no data showing Cas9-mediated toxicity in retina is known, it is preferable to limit Cas9 expression to the time frame required for efficiently editing the target locus. Control of Cas9 expression through a doxycycline regulated promoter has been successfully used[42]. The disadvantage of this approach, however, is that it doesn't allow for the use of tissue-specific promoters that limit expression (and by inference editing) to the target cell. The hGRK1 promoter efficiently limits Cas9 expression and gene editing to PRs. Here, a system wherein a doxycycline/tetracycline inducible, pol III/RNA promoter drives expression of a gRNA targeted to dual recognition sequences flanking the Cas9 cDNA on its expression cassette was developed.

The second hurdle to translation is the need to provide a replacement gene when the gRNA used for editing recognizes exonic sequence, as is the case with the GUCY2D-gRNA27 (FIG. 9). Alternatively, CRISPR/Cas9 reagents that selectively distinguish mutant from normal alleles may be utilized.

Figure 11A:
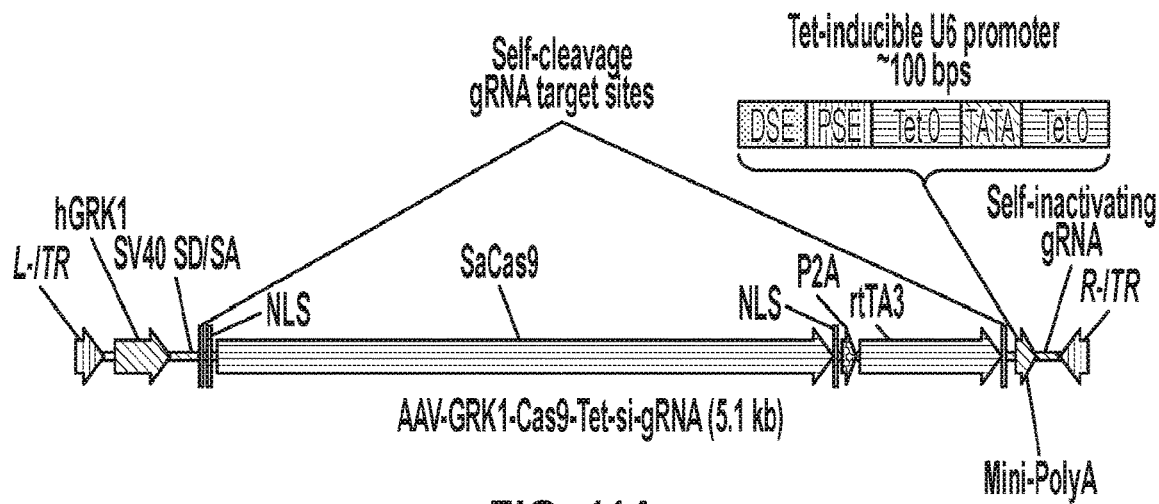
FIGS. 11A-11B show two different approaches for limiting the duration of Cas9 expression.

Two different approaches for limiting the duration of Cas9 expression were designed. The first is a Tet-inducible self-inactivating Cas9 system (FIG. 11A). The AAV-Cas9 construct contains targeting sites for a unique gRNA engineered to not recognize mouse, macaque or human genome targets and whose expression is under the control of a Tet-inducible pol III promoter. AAV-Cas9 also expresses the Tet-ON transactivator protein (rtTA) by way of a P2A ribosomal skipping-self-cleavage signal between Cas9 and rtTA. The version selected, rtTA3, is engineered to be completely inactive in the un-induced state, yet more sensitive and active in the presence of inducer (doxycycline), and is highly efficient in-vivo42-44. In a preferred embodiment, inclusion of all elements in a single vector ensures deactivation is not dependent on two different AAV vectors transducing the same cell.

Figure 11B:
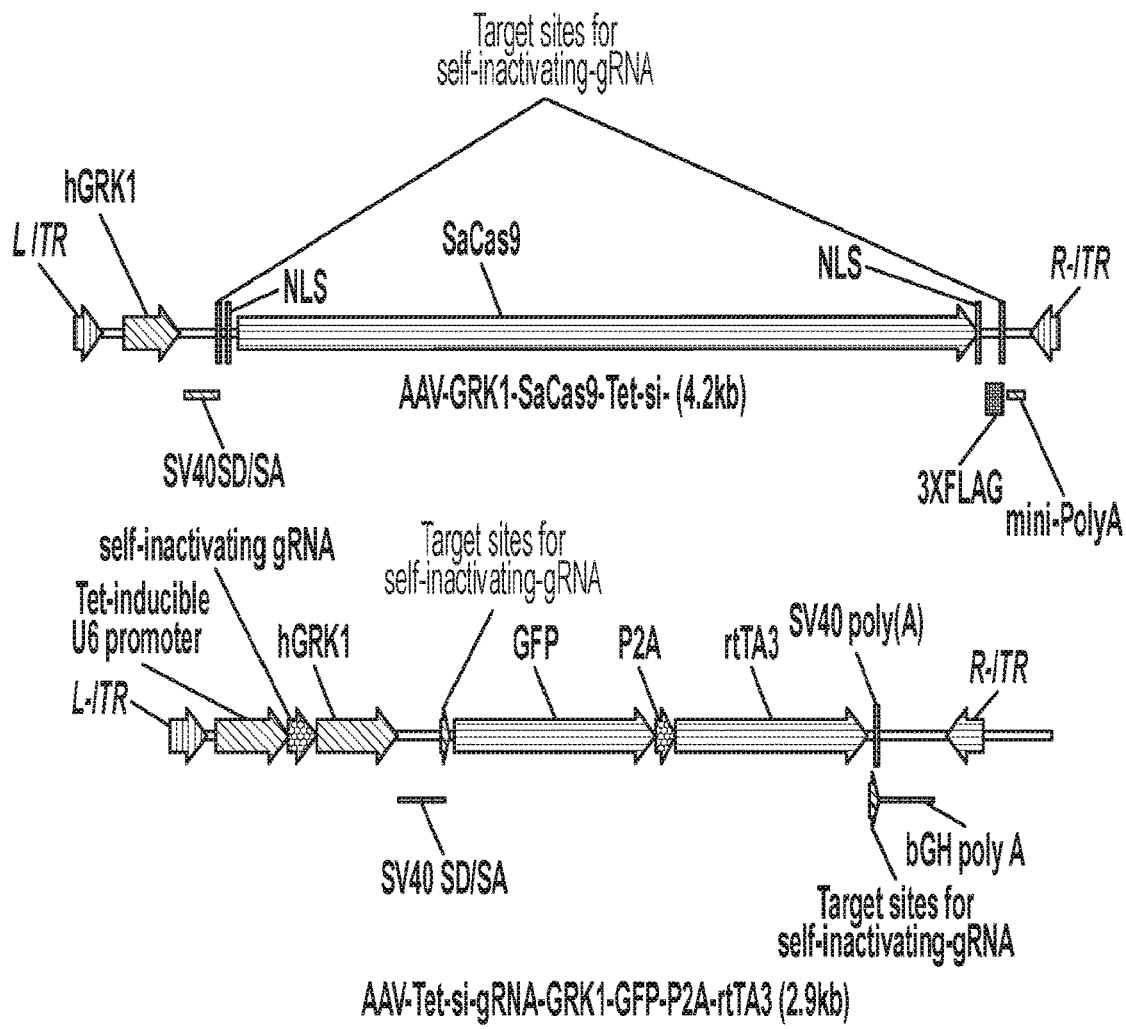

However, a single vector system results in a slightly over-sized AAV vector genome (5.1 KB). Therefore a second dual vector Tet-inducible self-inactivating system (FIG. 11B) was constructed. In this version, Cas9 vector contains flanking target sites for the inactivating gRNA. The second vector contains the Tet-inducible inactivating gRNA as well as GRK1 driving GFP-P2A-rtTA3 cDNA that is flanked by target sites for the inactivating gRNA. In the dual vector system, shut-down of GFP expression via editing by the Tet-induced gRNA will serve as a marker for Cas9 inactivation. Importantly, both systems, when induced, should result in ablation of both Cas9 and rtTA expression. The latter, also an exogenous protein derived from bacteria, has hampered broad application of Tet controllable systems due to delayed immune response to TetR or rtTA in some tissues. The feasibility and efficiency of self-inactivating Cas9 constructs are assessed. In Experiment 1, constructs are created containing Cas9 cDNA flanked by synthetic gRNA target sequence that contains consensus SaCas9 PAM sequence not predicted to occur in any human or mouse gene. Within the same construct a Tet-inducible U6 (or H1) promoter containing dual Tetracycline operator sequences (Tet O) is included located upstream and downstream (US/DS) of TATA box (FIG. 11). This arrangement has been shown to display tight suppression in the non-induced state and high responsiveness/strong expression of shRNAs following doxycycline induction in a number of mammalian cell lines. The design utilizes the same sequences published by Henriksen et al. This approach for regulating expression of an shRNA has been successfully used in vivo to create an inducible mouse model of Fiedreich's Ataxia (FRDAkd), which importantly displays an inducible and reversible PR phenotype, indicating that the Tet-inducible Pol III promoter is functioning well at the level of the photoreceptor (PR). Tet-inducible, self-inactivating Cas9 constructs first are tested by transfection of HEK293T and 661W cone PR cells under induced and non-induced conditions to confirm expression of Cas9 (WB) and cleavage upon induction (PCR). A self-inactivating Cas9 construct with a standard (non-inducible) U6 promoter driving the targeting gRNA (with the same arrangement of target sites) are also be created for comparison. It is worth noting that this non-regulated system was successful for expression of Cas9 sufficient to achieve gene editing at the target locus and self-cleavage of the Cas9 gene, in vitro.

The self-inactivating Cas9 constructs were packaged in AAV5 and co-injected with AAV5-Gucy2e-gRNA16-hGRK1-GFP into C57B16 mice. In some embodiments, Cas9 can be deactivated by Dox induction. Four weeks post injection, a subset of mice received doxycycline using the same dosing regimen used in FRDAkd mouse study. Following a 2-week induction period, all mice were humanely sacrificed and retinas collected for analysis of Cas9 expression by qPCR and WB, expression of the induced gRNA by qPCR, and indel analysis for editing of Gucy2e, as done in the past.

Example 4

The Knock-Out and Replace Strategy is Effective in Mice

Figure 24:
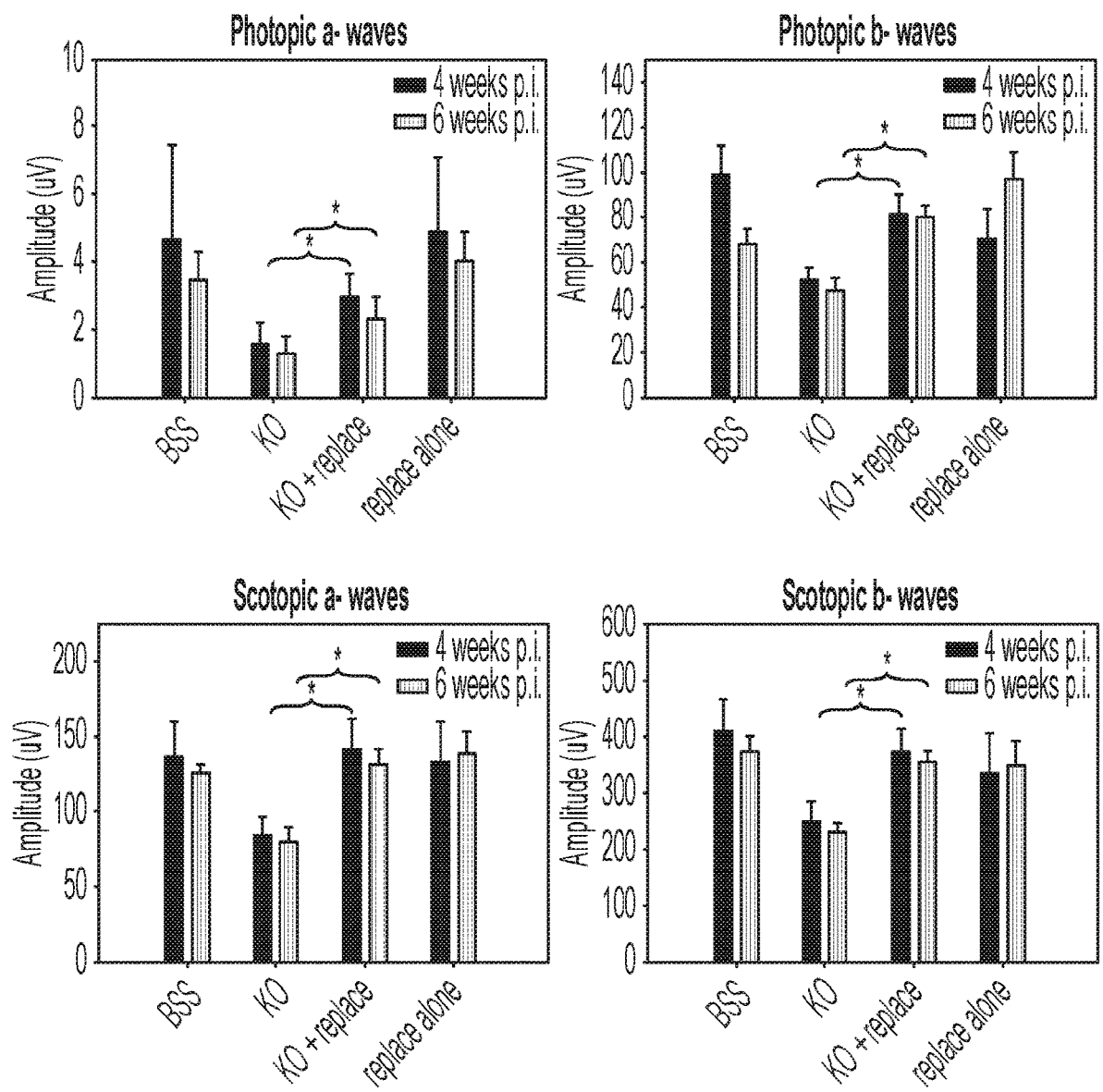
FIG. 24 shows ERG analysis performed at 4 and 6 weeks post-injection of $GC1^{+/-}:GC2^{-/-}$ mice injected with AAV8 (733)-hGRK1-hdGucy2e+AAV5-hGRK1-Cas9+AAV5-U6-Gucy2e-gRNA16-GRK1-GFP vectors.

Given this ability to efficiently edit Gucy2e and substantially reduce retGC1 expression, a "knock out+complementation in trans" approach was tested in which Gucy2e was knocked out and complemented with a "hardened" Gucy2e gene delivered together with the CRISPR/Cas9 reagents. The advantage of this approach is it could be used to treat all allelic forms of CORD6. "Hardened" Gucy2e, in which the sequence recognized by Gucy2e-gRNA16 and adjacent PAM site was modified using alternative codons, was cloned into the U6-Gucy2e-gRNA16-hGRK1-GFP construct to replace GFP. First, it was confirmed that hdGucy2e was functional in subretinally injected GCdko mice (i.e. lacking any functional guanylate cyclase activity) (data not shown). Next, the right eyes of $GC1^{+/-}:GC2^{-/-}$ mice were injected with AAV8(733)-hGRK1-hdGucy2e+AAV5-hGRK1-Cas9+AAV5-U6-Gucy2e-gRNA16-GRK1-GFP vectors at a total concentration of 3e12 vg/ml. Left eyes received AAV5-hGRK1-Cas9+AAV5-U6-Gucy2e-gRNA16-hGRK1-GFP. Fundoscopy was performed to confirm GFP expression (data not shown) and ERG was performed to evaluate retinal function at 4 and 6 weeks post-injection. As expected, left eyes (Gucy2e edited only) exhibited significant declines in retinal function by 4 weeks p.i. ERG amplitudes were higher in the right eyes which also received AAV-hdGucy2e (FIG. 4). Responses in right eyes (knock out+complementation in trans) were not significantly different from control eyes injected with BSS or hdGucy2e alone (FIG. 24).

Figure 12:
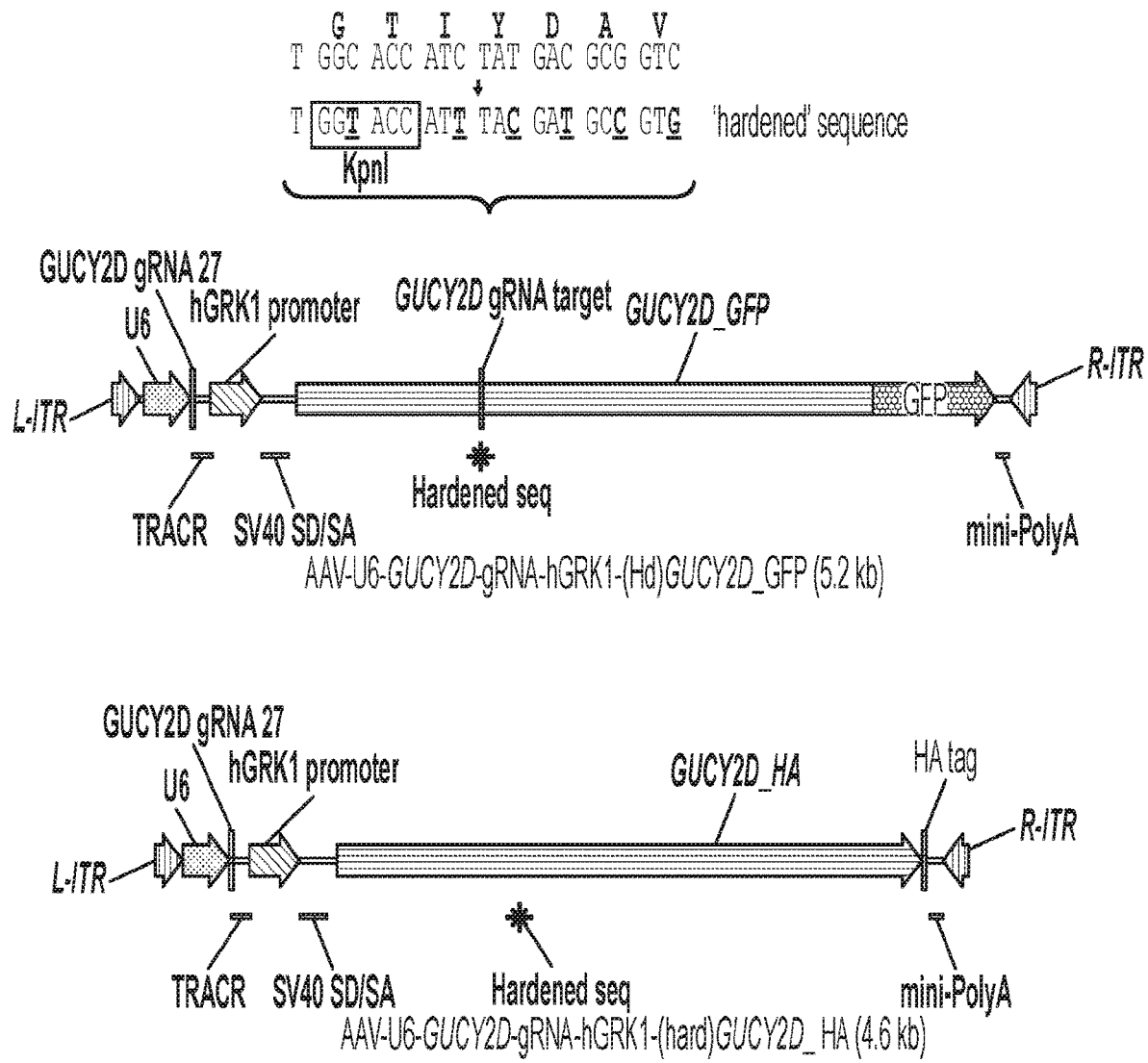
FIG. 12 shows AAV constructs containing gRNA targeted to Gucy2e and 'hardened' GUCY2D tagged with either GFP or HA at the C-terminus. Codon optimization adds KpnI restriction site for easy identification. SEQ ID NOs: 4-6 are listed from top to bottom, respectively.

In Experiment 2, experiments are carried out to test a 'knock out and replacement' approach in which to knock-out all retGC1 alleles and replace them with a 'hardened' GUCY2D gene delivered along with the CRISPR/Cas9 reagents. The advantage of this is that all allelic forms of CORD6 would be treatable via this approach. As a first step, a 'hardened' version of GUCY2D, in which the stretch of sequence recognized by GUCY2D-gRNA27 has been modified by the use of alternative codons, are cloned into the U6-Gucy2e-gRNA16-hGRK1-GFP construct to replace GFP (FIG. 12). The hdGUCY2D contain either HA or GFP tag on the C-terminus. It has been observed that C-terminus tag placement does not impair retGC1 function, and that GFP fluorescence is visible in OS of PRs. The GFP tag allows for identification of PRs expressing the exogenously delivered retGC1. Prior to use in gene editing experiments, vectors are first tested individually in GC1/GC2 double knock-out (e.g., lacking any functional guanylate cyclase activity) mice to confirm that hdGUCY2D-GFP or hdGUCY2D-HA adequately rescue retGC1 function in rods and cones. Into the optimal capsid identified in Example 2, the U6-Gucy2e-gRNA16-hGRK1-hdGUCY2D-GFP and hGRK1-Cas9 constructs are packaged. Both AAV vectors are then tested in $GC1^{+/-}:GC2^{-/-}$ and $GC2^{-/-}$ mice along with mice injected with AAV-Gucy2e-gRNA16-hGRK1-GFP+AAV-hGRK1-Cas9, the latter (lacking the hdGUCY2D replacement gene) establish the baseline for comparing phenotypic and structural improvements due to the replacement effect of hdGUCY2D. Separately $GC1^{+/-}:$ $Nrl^{-/-}$ and $Nrl^{-/-}$ mice are also injected with the vectors. This specifically assesses the ability of these reagents to knockout and replace retGC1 in a cone only retina, and adds to the understanding of whether there is a bias in editing efficiency between rods and cones. As in Example 2, success of injection is assessed by fundoscopy (GFP expression) and mice are carried out to 12 months post injection with the same in-life analysis and WB quantifying the level of remaining (endogenous, unedited) retGC1 vs. retGC1_GFP mediated by the replacement vector, respectively. Indel analysis was also performed. While homology directed repair (HDR) is not anticipated with hdGUCY2D serving as donor strand (sequence is divergent in this region, hence non-recognition of GUCY2D by gRNA Gucy2e), events were detected by way of the human versus mouse sequence and engineered sequence at the gRNA27 target location. If this approach is successful, the Gucy2e-gRNA16 are replaced by GUCY2D-gRNA27 for testing in primates (see Example 2, Experiment 3).

In Experiment 3, a heterozygous CORD6 mutant mouse that is currently under construction at Jackson labs was used. This mouse harbors the same C→A nucleotide inversion leading to the R838S CORD6 mutation and is being made using CRISPR/Cas9 to swap in a 100 bp region of exon 13 containing the aforementioned nucleotide change along with several other silent changes that aids in genotyping and indel analysis (e.g., to differentiate it from the wt allele after NHEJ repair and to identify instances of HDR). Specificity for the R838S allele is accomplished via the engineered Cas9 that specifically recognizes PAM sequence, NNGRRA, where 'A' conforms to the mutated nucleotide in the R838S GUCY2D. As can been visualized in FIG. 9, the protospacer sequence for gRNA directing the modified Cas9 (GUCY2D-gRNA838) is identical in mouse and human/macaque. In addition, the PAM sequence, while different, is still a consensus match to what is recognized by the engineered, allele specific Cas9. Therefore, allele specific editing of GUCY2D R838S was performed using heterozygous R838S CORD6 mutant mice. Expression of mutant R838S GUCY2D in line "379" is half of endogenous wtretGC1 levels. A robust degenerative phenotype in the heterozygous CORD6 mutant mice in which both cones and rods are dysfunctional and undergo degeneration (as opposed to the transgenic mice, in which rods are sole source of intrinsic dysfunction) is expected. Het CORD6 mutant mice are treated with allele specific gRNA-Cas9 reagents (AAV-GUCY2D-gRNA838-hGRK1-GFP+AAV-hGRK1-Cas9) in one eye only. The age of injection and AAV capsid used is determined based on the results of Example 2. Natural history is performed in the untreated eyes of these mice along with a group of naïve, untreated mice. As in Example 2, mice undergo ERG, OCT, IHC and WB to longitudinally characterize retinal function and structure. Retinas are collected, GFP+ cells sorted by FACS from which RNA and DNA are extracted for transcript and indel analysis to determine the percentage of editing in mutant versus wt alleles. As before, HDR is assessed by way of the silent mutations in the mutant allele.

Example 5

CRISPR/Cas9 Delivery to Primate Photoreceptors

In Example 5, parameters for efficient and safe gene editing of GUCY2D using subretinal or intravitreal delivery of AAV-CRISPR/Cas9 and an evaluation of clinically relevant vectors for 'Knock out+replacement' and 'allele specific' editing approaches in macaque were investigated.

Differences in retinal anatomy and biochemistry dictate that gene therapies showing proof of concept in rodent and canine models undergo careful consideration prior to clinical application. If necessary, they are modified based on results of testing in primate retina. Macaque species have a foveated retina with PR distribution, and barriers to transduction by AAV (e.g., inner limiting membrane) very similar to humans. Therefore in the experiments below, information gleaned in the pilot study were built upon by continuing to evaluate AAV-CRISPR/Cas9 reagents for editing of GUCY2D with the goal of establishing a dose range wherein effective editing takes place in the absence of pathological changes un-related to the targeted gene alteration. Existing reagents that promoted editing and expected phenotypic changes in the pilot study were used and adjusted from there. Additional AAV capsids of interest that have the potential for higher transduction efficiency (and hence better editing) and improved lateral spread thereby promoting transduction of a larger area of retina following SR injection are investigated. Gene editing following Ivt delivery of reagents using a novel capsid variant identified through directed evolution/screening performed in macaque is assessed. Lastly, reagents developed in Example 3 ('knock out and replacement' editing vectors and 'allele specific editing' vectors) are utilized, and their performance in primate retina is evaluated.

In the pilot primate study, 3e12 vg/ml each of GUCY2DgRNA27+hGRK1-GFP and hGRK1-Cas9 vectors were delivered (6e12 vg/ml combined concentration). Due to the limited number of animals central retinal samples for IHC were prioritized, where a striking reduction in retGC1 expression and shortening of outer segments concomitant with GFP expression (e.g., GUCY2D-gRNA vector transduction) is observed. Samples used to quantify GUCY2D editing in PRs were harvested from inferior temporal retina and indicated efficiencies of ~10%. This leads to the question, "what is the efficiency of editing in central versus mid-peripheral retina?" CORD6 is a disease which manifests in the macula and spreads outward. Hence, in young patients the macula would be included as a target of therapy. However, in patients with advanced disease, mid to peripheral retina is targeted as the macula has already suffered significant degeneration. Focus is therefore on both retinal areas in the context of GUCY2D editing.

In Example 3 the same GUCY2D gene editing reagents, packaged in AAV5, and delivered in two locations, a 100 ul macular bleb and a 100 ul mid-peripheral (inferior or superior) bleb were tested. Using a total of 3 animals, 3 doses, 3e12 vg/ml (same as pilot study), 1e12 vg/ml, and 3e11 vg/ml, were evaluated with a total of 2 eyes injected at each dose. For reference, pharmacology studies in macaque with AAV5-GRK1-GFP at the mid dose concentration (1e12 vg/ml) result in 75% of photoreceptor transduction. OCT and mfERG are performed pre-injection and again at two time points post injection (4 and 10 weeks) to evaluate retinal structure and function, respectively. General ophthalmological exams are performed prior to injection and again weekly to assess tolerability to vectors. In life GFP fluorescence (mediated by the gRNA vector) is captured using SLO. Serum and peripheral blood mononuclear cells (PBMCs) are collected for testing of neutralizing antibodies to the AAV5 capsid and cell-mediated immune reactivity to Cas9, respectively. Animals are humanely euthanized 10-12 weeks post injection. Macular (4 mm punch) and mid peripheral blebs (consisting of as much of the GFP positive bleb as possible) are processed separately to isolate PRs by FACS from which RNA and DNA are isolated for transcript and indel analysis. The most likely, off-target editing sites prioritized in coding sequence or in non-coding regions of tumor suppressors, oncogenes or inherited retinal disease-related genes also assessed for indels. Results of this experiment refine the dose of AAV required for efficient editing of GUCY2D in central and mid-peripheral retina, and provide a comparison of regional editing efficiencies.

Utilizing a dose selected based on Experiment 1, in Experiment 2 gene editing is evaluated using two additional AAV capsids—AAV8(dbY-F+T-V) and AAV2(4pMut)ΔHS relative to AAV5 (rationale for their use is described above). Using three animals, the same approach is utilized as above (central and mid-peripheral blebs). Each capsid is injected into 2 eyes. Digital video recording (4K resolution) is used to capture images of blebs immediately after injection. This, in conjunction with SLO images of GFP expression and landmark blood vessels visible in both image modalities are used to evaluate lateral spread of transduction outside of the bleb area. It is found that AAV5-mediated transgene expression remains close to the margins of the bleb. All other procedures are the same as above (e.g., OCT, mfERG, quantification of transcripts, and PR editing efficiencies from central and peripheral retina and safety end points). In Experiment 3, the same GUCY2D editing reagents packaged in novel AAV capsid variants mined from capsid library screening in primate via Ivt injection are tested. Using three animals, the three best capsids (each capsid mutant is injected into 2 eyes each) are tested. The delivered dose is determined by ongoing experiments). GFP transgene expression is documented by SLO and the same procedures performed as above. A 4 mm macular punch is used for isolating PRs and performing transcript and indel analysis to quantify editing efficiencies. Based on experience, transduction by Ivt-delivered AAV vectors is greater in the central retina. However, if peripheral transduction is sufficient (based on SLO imaging), peripheral retina is collected for quantification of editing.

In Experiment 4, "knock-down+replacement" reagents developed in Example 3 is packaged in the best performing capsid identified in Experiments 1 through 3. It is likely that the injection route is subretinal using one of the capsids in Experiment 2, however, the possibility of using Ivt mediated delivery of one of the capsids tested in Experiment 3 is not excluded. Here 4 animals are used, with 2 receiving AAV-U6-GUCY2D-gRNA27-hGRK1-(Hd)GUCY2D_GFP(or HA) bilaterally, 2 receiving AAV-U6-GUCY2D-gRNA27-hGRK1-(Hd)GUCY2D_GFP(or HA) in their left eyes and AAV-hGRK1-GFP control vector in their right eyes. Dose is determined by experiment 1 (or 3), with left eyes receiving control vector (AAV-hGRK1-GFP) at the same total dose. A 100 ul macular injection a 100 ul inferior or superior mid-peripheral injection is placed in each eye. In life analysis is performed as above. SLO is used to evaluate expression of GFP-tagged GUCY2D (retGC1_GFP) and GFP in control eyes. Two macular blebs and two peripheral blebs are harvested for quantification of gene editing. As in the mouse experiments HDR is assessed by the silent mutation engineered into the HdGUCY2D. Two macular blebs and two mid-peripheral blebs, along with areas of untreated retina, are evaluated by WB to quantify retGC1 and retGC1_GFP to ascertain the level of both GUCY2D knockout and replacement with GUCY2D_GFP. The remaining two macular blebs and mid-peripheral blebs undergo careful IHC/microscopy to look for retGC1_GFP in OS of photoreceptors.

In Experiment 5, allele specific reagents developed in Example 3 (AAV-GUCY2D-gRNA838-hGRK1-GFP+AAVhGRK1-Cas9) are tested to confirm their lack of editing at the wt GUCY2D locus and general tolerability. A total of 2 animals are used and vector dose based on results of experiments above. Animals receive macular and mid-peripheral blebs. The same in life analyses and end-point analyses are performed. Macular and mid-peripheral blebs are collected, undergo FACS to isolate PRs and RNA/DNA isolated for transcript/indel analysis to determine if editing occurred at the GUCY2D locus. Indels are evaluated at predicted, off-target editing sites with prioritization of coding sequence or non-coding regions of tumor suppressors, oncogenes or inherited retinal disease-related genes.

Example 6

Figure 21:
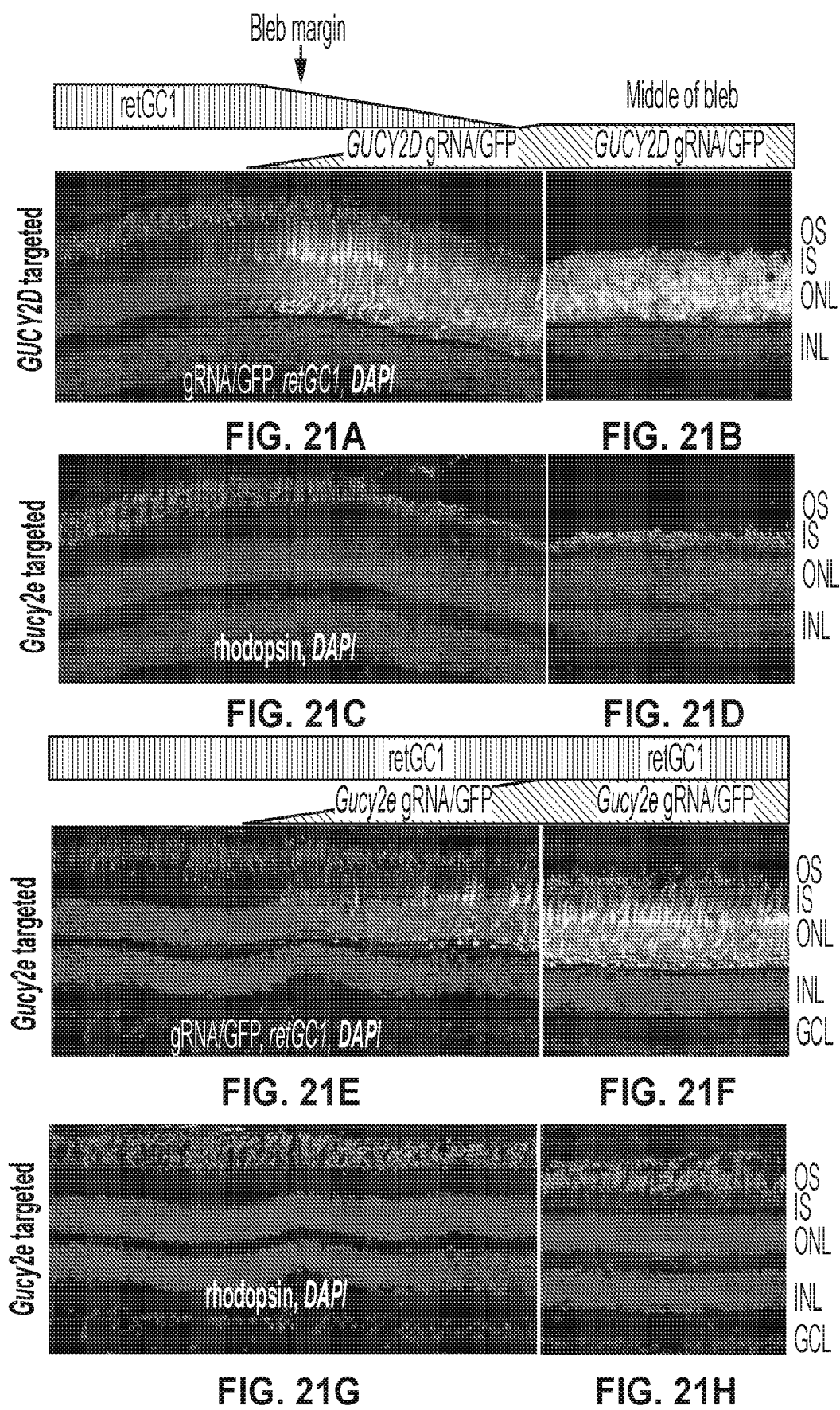
FIGS. 21A-21H show stained retinal cross sections from macular blocks of GR114QB's right and left eyes, with focus placed on the edge of the bleb, where both GFP+ and GFP− PRs (those with and without gRNA) could be found.

AAV-CRISPR/Cas9-Based Editing of GUCY2D Alters Retinal Structure and Function and Reduces retGC1 Expression in Macaque Photoreceptors Retinal cross sections from macular blocks of GR114QB's right and left eyes were stained, with focus placed on the edge of the bleb, where both GFP+ and GFP− PRs (those with and without gRNA) could be found. In AAV-GUCY2D-gRNA/Cas9-injected retina, retGC1 expression was reduced or absent from GFP+ PRs (FIGS. 21A, 21B). Outer segments within the GFP+ bleb were also noticeably shortened, as indicated by rhodopsin staining in FIG. 21C, and FIG. 21D. Outside the bleb, where presumably no GUCY2D-gRNA was expressed (or expressed at levels below detection), retGC1 was present in the PR OS, which appeared morphologically normal (FIGS. 21A and 21C). Despite a reduction in PR OS length in the macular block of this eye, ONL thickness was normal and unchanged relative to the control eye. Sections from the inferior nasal bleb of GR114QB OD were also evaluated. retGC1 expression was absent from PRs within this peripheral bleb and a pronounced loss of ONL was also observed. A single row of PR cell bodies remained, all of which were cones, as evidenced by their labeling with cone arrestin antibody. These cones lacked IS and OS. In the control eye (AAV-Gucy2e-gRNA/Cas9-injected), retGC1 was visible in PR outer segments (OS) throughout the retinal section regardless of whether that PR expressed GFP (i.e., Gucy2e gRNA) (FIGS. 21E and 21F). No changes in PR OS or ONL thickness were observed retinas injected with AAV-Gucy2e gRNA/Cas9 (FIGS. 21G and 21H).

Figure 20:
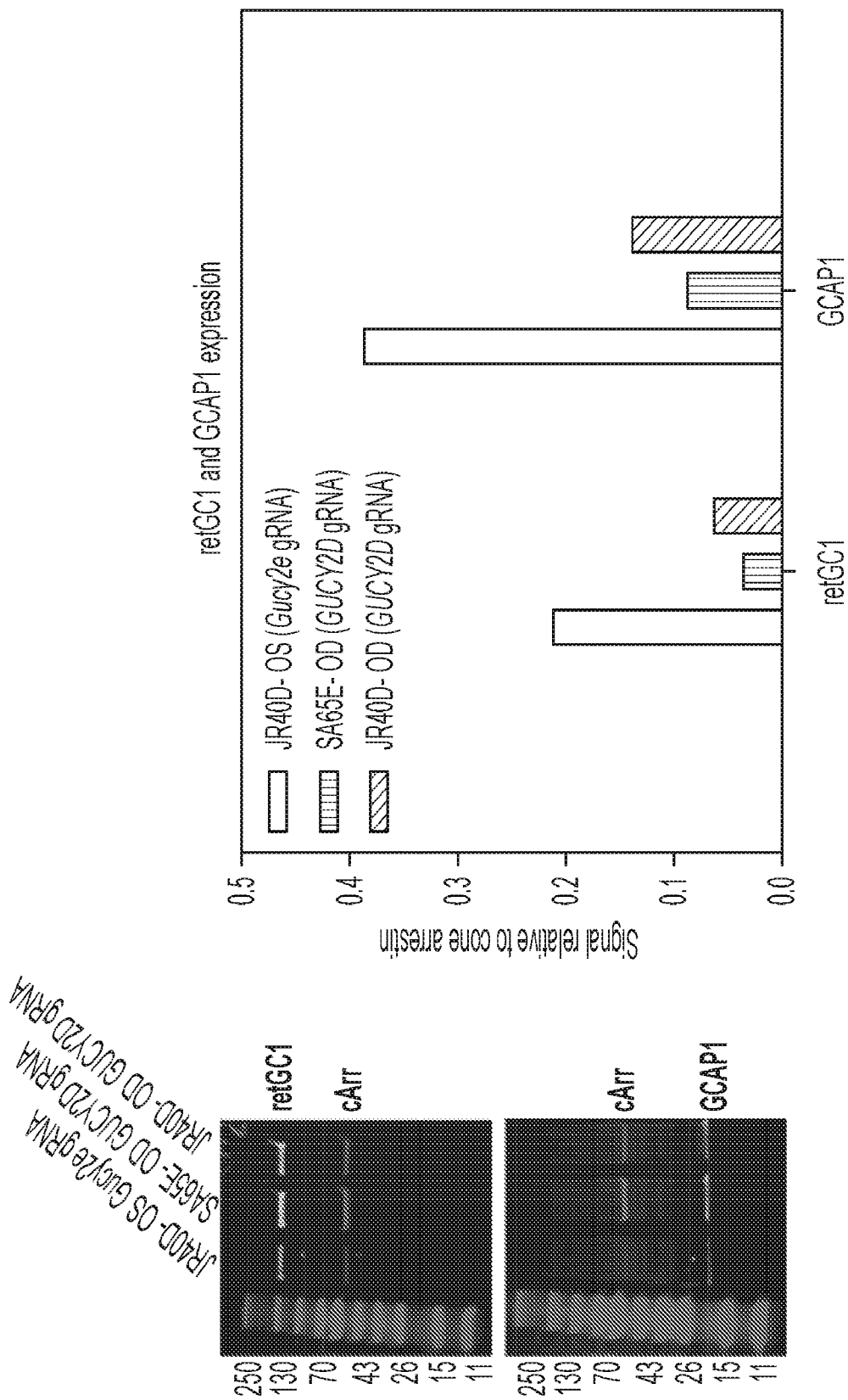
FIG. 20 shows Western blots of protein from macaque retinas treated with AAV-Cas9 plus either AAV-GUCY2D-gRNA27 or control AAV-Gucy2e-gRNA16 were probed for the presence of retGC1 and its biochemical partner, GCAP1.

Western blots of protein from macaque retinas treated with AAV-Cas9 plus either AAV-GUCY2D-gRNA27 or control AAV-Gucy2e-gRNA16 were probed for the presence of retGC1 and its biochemical partner, GCAP1. Both were normalized to primate cone arrestin to control for input. Clear reductions in both retGC1 and GCAP1 were observed in retinas treated with AAV-GUCY2D-gRNA27/Cas9 (FIG. 20). Confirming the IHC results, this shows that editing of GUCY2D leads to loss of retGC1 expression in macaque photoreceptors.

As shown in FIG. 22 (bottom), transcript analysis of WT mice 6 weeks post-injection with AAV-Gucy2e gRNA-hGRK1-GFP vector alone reveals Gucy2e gRNA expression is correlated with the level of GFP expression in associated fundus images.

Figure 23A:
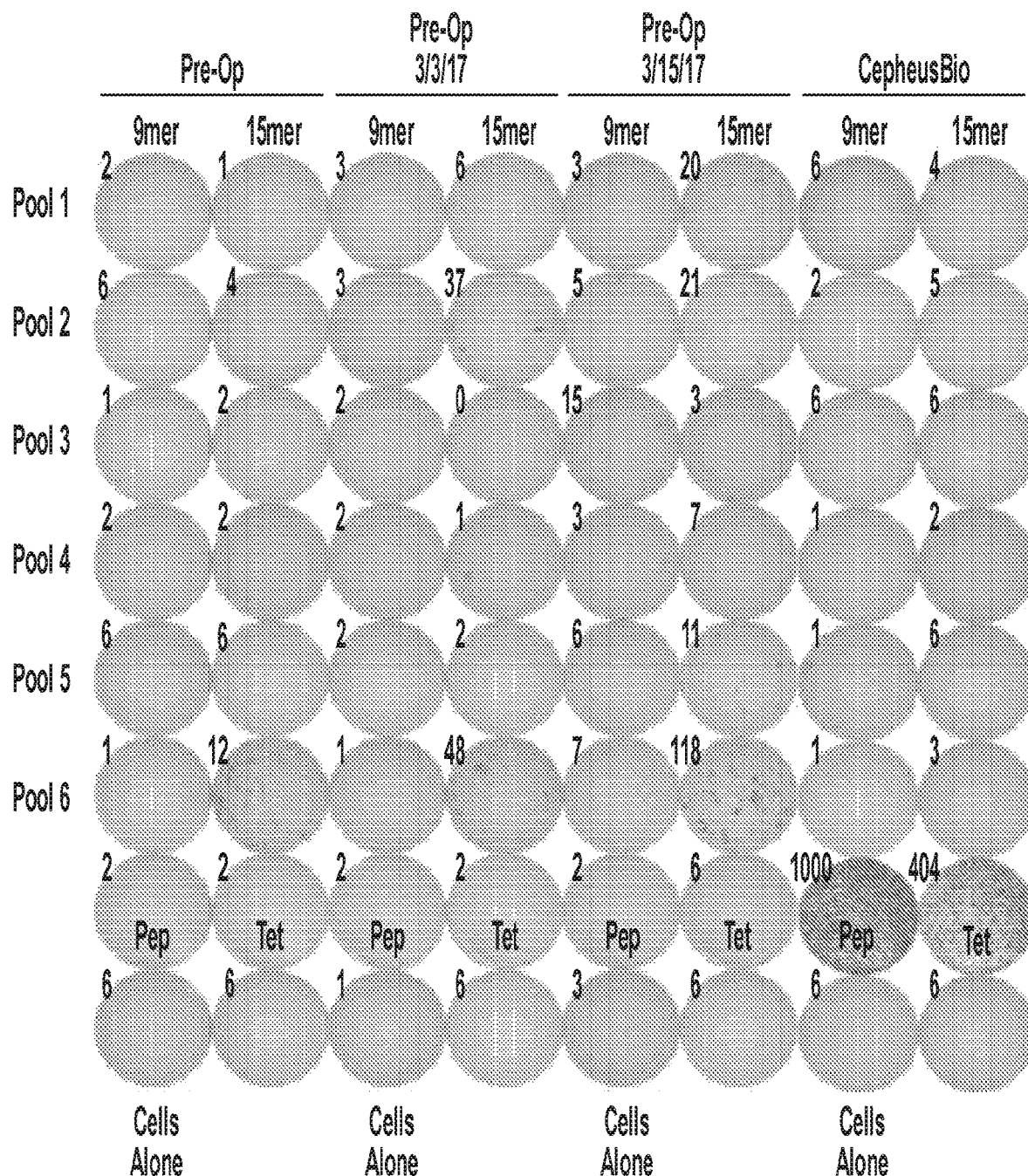
FIG. 23A-23C show the ELISPOT assay of T cell responses to SaCas9.
Figure 23B:
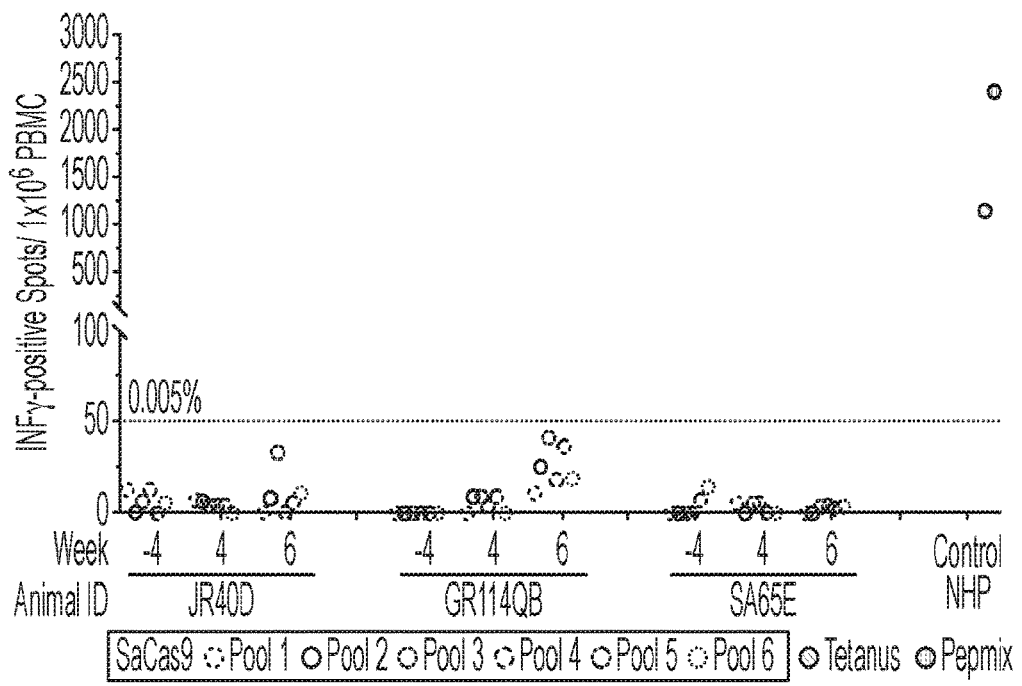
Figure 23C:
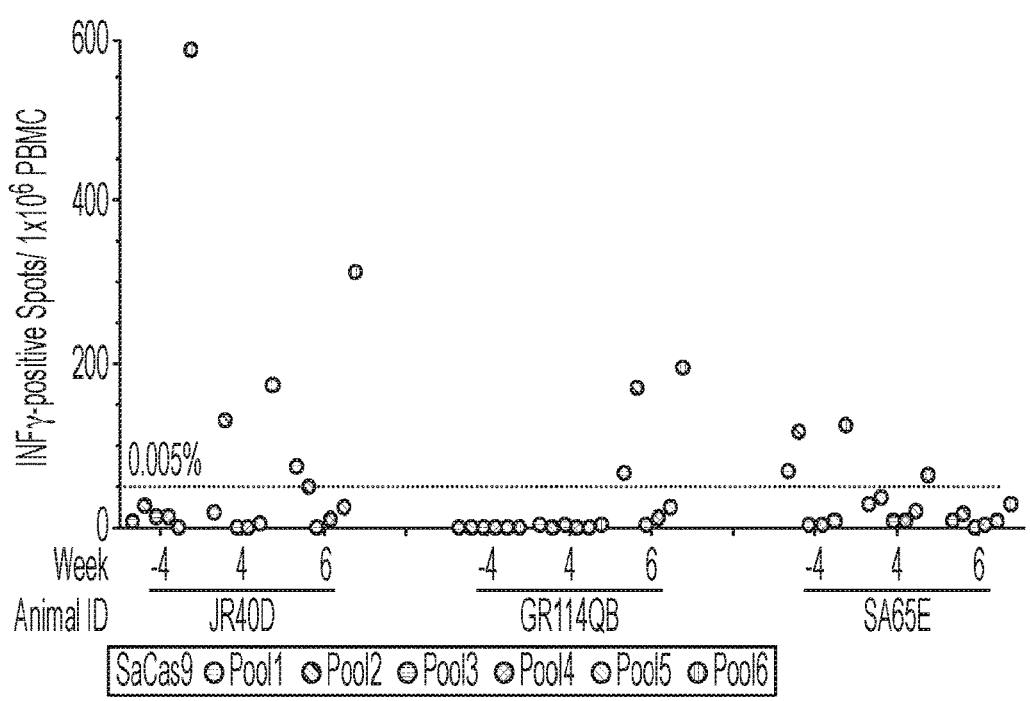

FIG. 23A is a representative ELISPOT plate image. PBMCs isolated from JR40D at specified timepoints were plated at 160,000 to 370,000 cells per well and mixed with individual SaCas9 peptide pool containing ~36 peptides of either 9-mers overlapping by 4 amino acids, or 15-mers overlapping by 10 aa. The total peptides from 6 pools tile the entire SaCas9 protein sequences. The control NHP from CepheusBio was immunized with viral antigens in Pepmix and Tetanus. No T cell antigens were added to the wells with cells alone. INFγ-positive spots normalized to 1E6 PBMC are presented in FIG. 23B for CD8 T cell responses to SaCas9 9-mer antigens, and FIG. 23C for CD4 T cell responses to SaCas9 15-mer antigens.

As shown in FIG. 24, ERG analysis performed at 4 and 6 weeks post-injection of $GC1^{+/-}:GC2^{-/-}$ mice injected with AAV8(733)-hGRK1-hdGucy2e+AAV5-hGRK1-Cas9+AAV5-U6-Gucy2e-gRNA16-GRK1-GFP vectors demonstrated that responses in right eyes (knock out+complementation in trans) were not significantly different from control eyes injected with BSS or hdGucy2e alone.

REFERENCES CITED

1. Bae S, Park J, Kim J S. Cas-OFFinder: a fast and versatile algorithm that searches for potential off-target sites of Cas9 RNA-guided endonucleases. *Bioinformatics*. May 15 2014; 30(10):1473-1475.
2. Reyon D, Maeder M L, Khayter C, et al. Engineering customized TALE nucleases (TALENs) and TALE transcription factors by fast ligation-based automatable solid-phase high-throughput (FLASH) assembly. *Curr Protoc Mol Biol*. July 2013; Chapter 12:Unit 12 16.
3. Boye S E. The human rhodopsin kinase promoter in an AAV5 vector confers rod- and cone-specific expression in the primate retina. *PloS one*. October 2012; 23(10):1101-1115.
4. Khani S C, Pawlyk B S, Bulgakov O V, et al. AAV-mediated expression targeting of rod and cone photoreceptors with a human rhodopsin kinase promoter. *Invest Ophthalmol. Vis. Sci.* 9/2007 2007; 48(9):3954-3961.
5. Ruan G X, Barry E, Yu D, Lukason M, Cheng S H, Scaria A. CRISPR/Cas9-Mediated Genome Editing as a Therapeutic Approach for Leber Congenital Amaurosis 10. *Mol Ther*. Feb. 1 2017; 25(2):331-341.
6. Karan S, Frederick J M, Baehr W. Novel functions of photoreceptor guanylate cyclases revealed by targeted deletion. Mol. Cell Biochem. 1/2010 2010; 334(1-2):141-155.
7. Boye S L, Peshenko I V, Huang W C, et al. AAV-mediated gene therapy in the guanylate cyclase (RetGC1/RetGC2) double knockout mouse model of Leber congenital amaurosis. *Hum. Gene Ther.* 2/2013 2013; 24(2):189-202.
8. Haire S E, Pang J, Boye S L, et al. Light-driven cone arrestin translocation in cones of postnatal guanylate cyclase-1 knockout mouse retina treated with AAV-GC1. *Invest Ophthalmol. Vis. Sci.* 9/2006 2006; 47(9):3745-3753.
9. Choudhury S, Strang C E, Alexander J J, et al. Novel Methodology for Creating Macaque Retinas with Sortable Photoreceptors and Ganglion Cells. *Front Neurosci.* 2016; 10:551.
10. Monteys A M, Ebanks S A, Keiser M S, Davidson B L. CRISPR/Cas9 Editing of the Mutant Huntingtin Allele In Vitro and In Vivo. *Mol Ther*. Jan. 4 2017; 25(1):12-23.
11. Shin J W, Kim K H, Chao M J, et al. Permanent inactivation of Huntington's disease mutation by personalized allele-specific CRISPR/Cas9. Human molecular genetics. Sep. 15 2016.

Materials and Methods

Guide RNA Design.

gRNAs were designed to target early coding sequence in either Gucy2e or GUCY2D, with the goal of preventing expression of retGC1 protein. Guide design for *S. aureus* gRNAs was carried out using Godot, a custom guide RNA design software based on the public tool Cas-OFFinder[33]. Godot scores guides after calculating their genome-wide off-target propensity. Genome builds used were MacFas5 for cynomolgus macaque gRNAs and mm10 for mouse guide RNAs. NHP GUCY2D guides were selected to also target the human GUCY2D gene. Guides were prioritized based on orthogonality in the target species genome, with strong preference given for gRNAs starting with a 5'G and a PAM sequence of NNGRRT.

Guide RNA Efficacy Testing

Activity of guide RNAs was tested by transfecting a plasmid encoding Sa Cas9, driven by the CMV promoter, and linear DNA expressing guide RNAs, driven by U6 promoter, into cells. NIH 3T3 cells (ATCC) were used to test mouse gRNAs and HEK293 cells (ATCC) were used to test NHP gRNAs (because all NHP gRNAs cross-react with human gene sequence). NIH 3T3 cells and HEK293 cells were maintained in Gibco DMEM+Glutamax supplemented with 1% PenStrep and 10% fetal bovine serum. HEK293 cells were transfected with 750 ng Cas9 plasmid and 250 ng linear gRNA-expressing DNA using TransIT-293 Transfection Reagent (Mirus Bio). NIH 3T3 cells were transfected by Lonza nucleofection with 750 ng Cas9 plasmid and 250 ng linear gRNA-expressing DNA in SG nucleofection solution, using pulse code EN-158. Cells were harvested 3 days post-transfection and genomic DNA was isolated using the Agencourt DNAdvance kit (Beckman Coulter) according to manufacturer's instructions. Editing rates were determined by PCR amplifying the region surrounding the gRNA target sites and performing a standard T7 Endonuclease I assay (New England Biolabs), which was analyzed on a QIAxcel analyzer (Qiagen).

Experimental Animals

To avoid confusion about nomenclature across species, genes and their encoded proteins are described herein. Retinal guanylate cyclase-1 (retGC1) and retinal guanylate cyclase-2 (retGC2) are encoded in mice by Gucy2e and Gucy2f, respectively. In macaque, retGC1 is encoded by GUCY2D. C57Bl/6J (WT), and Gucy2e knockout (GC1$^{-/-}$) mice were obtained from Jackson Laboratories (Bar Harbor, Me.)[34]. Gucy2e/Gucy2f double knockout (GCdko) mice were generously provided by Dr. Wolfgang Baehr (University of Utah)[5]. R838S CORD6 transgenic mice (line '379') were generously provided by Dr. Alex Dizhoor (Salus University)[10]. To generate a line containing a single allele of Gucy2e and a full knockout of Gucy2f (GC1$^{+/-}$:GC2$^{-/-}$), GCdko mice were first crossed with wild type C57/B16 (GC1$^{+/+}$:GC2$^{+/(+)}$) mice to create experimental GC1$^{+/-}$:GC2$^-$ males, and GC1$^{+/-}$:GC2$^{+/-}$ double-heterozygote females. To generate experimental females (GC1$^{+/-}$:GC2$^{-/-}$), experimental males were back-crossed with GCdko females. Experimental females and males were crossed to produce GC1$^{+/+}$:GC2$^{-/(-)}$ breeders. These breeders were used to produce 100% experimental offspring when bred with GCdko. Genotyping primers to identify presence/absence of Gucy2e (retGC1) included 'GC1F4' (forward primer in WT intron 4), 5'-TCCTATCCACGACAGGAC-CAAGACTGT (SEQ ID NO: 33), 'GC1R4' (reverse primer in WT intron 5), 5'-GAGAGCAGAAGGGTAGCATT-AGCTCAG (SEQ ID NO: 34), and 'NeoF4' (forward primer in neo cassette), 5'-ACCGCTATCAGGACAT-AGCGTTGGCTA (SEQ ID NO: 35). For Gucy2f (retGC2), 'Pla2' (forward primer in neo cassette), 5'-GTTCTTCGGACGCCTCGTCAACAC (SEQ ID NO: 36), 'GC2mt-R2' (reverse primer), 5'-GTGCCTA-CAGGACTCTTGATGTCATTC (SEQ ID NO: 37), 'GCtowt1' (WT) 5'-CAAGACATTTGACAGGAGT-TACTC (SEQ ID NO: 38), and 'GCtoda6' (WT) 5'-GTTCT-GAGCTACAGATCCTACAGTG (SEQ ID NO: 39) were used. R838S CORD6 mice were genotyped using a forward primer located in exon 4 and reverse primer bridging exons 7 and 8 of human RetGC1. Respective sequences are 5'-CGATCCAAACAACATCTGCGGT-3' (SEQ ID NO: 40) and 5'-CAGCCAAACCCTGTCTCCCTCAT-3' (SEQ ID NO: 41). Primer annealing was independent of R838S mutation.

All mice were bred and maintained at the University of Florida Health Science Center Animal Care Services Facility under a 12-hour/12-hour light/dark cycle. Food and water were available ad libitum. All experiments were approved by the University of Florida's Institutional Animal Care and Use Committee and were conducted in accordance with the ARVO Statement for the Use of Animals in Ophthalmic and Vision Research and with National Institutes of Health regulations.

Three adult, male macaques (*Macaca fascicularis*) were used in this study (SA65E—7 yr, 10 months; GR114QB—6 yr, 1 month; JR40D—6 yr, 9 months). All procedures performed on macaques were approved by Institutional Animal Care and Use Committees at the University of Alabama at Birmingham (UAB) and performed in accordance with the Association for Research in Vision and Ophthalmology Statement for the use of animals in ophthalmic and vision research.

Construction of AAV Vectors

Vector plasmids pMC12 (pTR-U6-mGucy2e-16-GRK1-GFP), pKJS115 (pTR-U6-nhpGUCY2D-27-GRK1-GFP) and pAF251 (pTR-GRK1-Cas9) were manufactured to large scale and purified by solid phase, anion exchange chromatography using a commercially available kit (Qiagen). Subsequently, vector plasmids along with AAVS helper plasmid (pXYZ5), containing AAV2 rep, AAVS cap and required Adenovirus helper genes were co-transfected into HEK293 cells according to previously published methods[35]. Cells were harvested 72 hrs post transfection. Virus was purified by iodixanol discontinuous density gradient ultracentrifugation followed by ion exchange chromatography and buffer exchanged into a Balanced Salt Solution (BSS) supplemented with 0.014% Tween 20. Virus was titered for vector genomes (vg) by Dot-blot and evaluated by SDS-PAGE to confirm high level purity of capsid proteins VP1, VP2, and VP3 (data not shown). Each undiluted vector preparation was tested for the presence of endotoxin with all registering at <5 Eu/ml. Additionally, AAVS-Gucy2e-gRNA16-hGRK1-GFP and AAV5-GUCY2D-gRNA27-hGRK1-GFP vector particles were also visualized by electron microscopy to confirm the presence of mostly 'full' particles. Individual vector titers were as follows: AAV5-Gucy2e-gRNA16-hGRK1-GFP: 8.64×10$^{13}$ vg/ml, AAVS-GUCY2D-gRNA27-hGRK1-GFP: 1.56×10$^{14}$ vg/ml and AAV5-hGRK1-Cas9: 6.95×10$^{13}$ vg/ml. Vectors were diluted with BSS-Tween to the desired concentration for experiments.

Subretinal Injections

One microliter (μl) of vector(s) was delivered to the subretinal space of C57B1/6J (WT), GC1$^{+/-}$:GC2$^{-/-}$, or R838S CORD6 mice under a Lecia M80 Stereomicroscope according to previously published methods[36]. To compare promoters driving Cas9, single vectors were injected into WT mice at either high (3×10$^{12}$ vg/ml) or low (3×10$^{11}$ vg/ml) concentrations. To evaluate gene editing in all mouse strains, two vectors were co-delivered, each at 3×10$^{12}$ vg/ml, for a total concentration of 6×10$^{12}$ vg/ml. A subset of GC1$^{+/-}$:GC2$^{-/-}$ mice received higher doses with vectors co-delivered at 3×10$^{13}$ vg/ml, for a total concentration of 6×10$^{13}$ vg/ml. Injection blebs were imaged immediately following injection and further analysis was carried out only on animals that received comparable, successful injections (≥60% retinal detachment and minimal complications). It is well established that the area of vector transduction corresponds to at least the area of retinal detachment[36,37]. Subretinal injections in macaque eyes were performed according to the previously published methods with minor modifications[29]. Three macaques received subretinal injections of AAV5-U6-GUCY2D-gRNA27-hGRK1-GFP+AAV5-hGRK1-Cas9 (right eyes) and AAV5-Gucy2e-gRNA16-hGRK1-GFP+AAV5-hGRK1-Cas9 (left eyes), except for one animal whose left eye was used for other purposes. Three distinct subretinal blebs were created in each eye to accommodate multiple outcome measures including cryo-immunohistochemistry, western blot, and transcript/indel analysis. Blebs were directed to the macula (M), inferior nasal (IN), and inferior temporal (IT) retina in each eye. The ability to surgically create multiple, distinct blebs in NHP for a similar purpose[38] was previously demonstrated. Subjects received Dexamethasone (0.25 mg/kg IM) the day before and the day of surgery. An Accurus 800CS surgical system with Xenon light source, Total Plus 23 gauge Vitrectomy Pak (Alcon, Inc., Fort Worth, Tex.) and Zeiss VISU 200 ophthalmic surgical microscope equipped with digital video (Endure Medical, Cumming, Ga.) were used for the surgery. A standard 23-gauge three-port pars plana vitrectomy was performed with an inferior infusion cannula maintaining a pressure of 20-30 mm/Hg with BSS Plus (Alcon, Inc., Fort Worth, Tex.). Subsequently, the superior-temporal sclerotomy was enlarged with a 20-gauge MVR blade for the injection cannula. A 39-gauge injection cannula with 20-gauge shaft (Synergetics, O'Fallon, Mo.) was used to deliver vector into the subretinal space of subjects SA65E and GR114QB. A 39-gauge injection cannula (Katalyst) attached to a 1 ml disposable barrel injector (Katalyst Injector System, DV1600) was used to deliver vector into the subretinal space of subject JR40D. All blebs in subject SA65E were created without incident. In subject GR114QB, a small air bubble was inadvertently delivered to the IT bleb of the OD eye but no subsequent damage was observed. All other blebs in this subject were created without incident. Slight retinal damage occurred in the IN and IT blebs of subject JR40D's OS eye. All other blebs in this subject were created without incident. Following subretinal injections, sclerotomy sites and conjunctiva were sutured closed using 9.0 vicryl, and subconjunctival cefazolin and dexamethasone were administered. To prevent corneal drying during surgical recovery, triple antibiotic ophthalmic ointment was applied to both eyes. Upon recovery, the subject received subcutaneous sustained release buprenorphine (0.2 mg/kg) and Meloxicam (0.6 mg/kg) and cefazolin (25 mg/kg IM). In all but one eye, recovery was uneventful; the corneas of the treated eyes remained clear with only mild conjunctival redness, which resolved within a day after surgery. The OS eye of subject JR40D showed slight vitreal haziness four days post-operatively. The animal was treated with Dexamethasone (0.25 mg/kg IM) for 1 day followed by a 4 day taper and, upon exam, the eye appeared normal 8 days post-operatively.

In-Life Imaging

Mice were sedated and expression of GFP was documented using a Micron III fundoscope (Phoenix Research Laboratories, Pleasanton, Calif.) with a green fluorescent filter. GFP expression was similarly documented at either 4, 6, 10 or 20 weeks post subretinal injection in all strains that received AAVS-GUCY2D-gRNA27-hGRK1-GFP or AAVS-Gucy2e-gRNA16-hGRK1-GFP vectors. Exposure settings were identical for all mice. Averaging of GFP pixel intensity was performed across select cohorts by loading images in sequence and using the average intensity Z-projection in ImageJ.

Outer nuclear layer (ONL) thickness in WT and GC1$^{+/-}$ GC2$^{-/-}$ mice was quantified by optical coherence tomography (OCT) (Bioptigen Inc, Durham, N.C.) between 4 to 20 weeks p.i. according to previously published methods[39]. Briefly, after sedation and dilation, three lateral images (nasal to temporal) were collected, starting 3 mm above the meridian crossing through the center of the optic nerve head (ONH), at the ONH meridian and 3 mm below ONH meridian. A corresponding box centered on the ONH with eight measurement points separated by 3 mm from each other was created. ONL thickness in mice injected with AAV-Cas9 plus either AAV-Gucy2e-gRNA or control AAV-GUCY2D-gRNA were compared. Statistical significance was determined by a paired t-test with P values of <0.05 considered significant.

All NHP subjects were sedated, situated and imaged using a Spectralis™ HRA+OCT (Heidelberg Engineering, Inc., Germany) scanning laser ophthalmoscope as previously described. Images were obtained with either the 30 or 55 degree objective using infrared (820 nm) and autofluorescence (488 nm) modes without optical coherence tomography (OCT), and the 30 degree objective for OCT scans. Volume OCT scans were obtained in the macular region of all treated eyes. Fundus images were obtained using a Topcon TRC-50EX Retinal Camera with user-selectable excitation/emission filters, and a Fundus Photo Digital Imaging System (St. Louis Ophthalmic Equipment Co.).

Electroretinographic Analyses

Full field electroretinograms (ERGs) of treated mice were recorded using a UTAS Visual Diagnostic System equipped with Big Shot Ganzfeld (LKC Technologies, Gaithersburg, Md.) or a Diagnosys Celeris unit (Lowell, Mass.) according to methods previously described with minor modifications[40]. Recordings were initially conducted at 6 weeks p.i. (p.i.), with certain cohorts subjected to repeated, longer-term measurements. Following overnight dark adaptation, scotopic ERGs were elicited at intensities ranging from −20 db to 0 db with interstimulus intervals of 30 sec, averaged from five measurements at each intensity. Mice were then light-adapted to a 30 cds/m$^2$ white background for 7 min. Photopic responses were elicited, with intensities ranging from −3 dB to 10 dB. Fifty responses with interstimulus intervals of 0.4 sec were recorded in the presence of a 20 cds/m$^2$ white background and averaged at each intensity. The b-wave amplitudes were defined as the difference between the a-wave troughs to the positive peaks of each waveform. At each time point, maximum scotopic and photopic b-wave amplitudes (those generated at 0 dB and 10 dB, respectively) from all treated, untreated, and control mice within each cohort were averaged as mean±standard error. Values were imported into SigmaPlot for final graphical presentation.

Tissue Preparation

At approximately 6 or 20 weeks p.i., mouse eyes were enucleated and fixed in 4% paraformaldehyde for ~12 hours. Eyecups were dissected and prepared for sectioning according to previously described methods[41].

At 8 weeks p.i., NHPs were perfused, euthanized, and their eyes enucleated/processed according to previously published methods with some modification[29,42]. The resulting eyecups were immersed in oxygenated Ames media. Retina from the OD and OS eyes were then dissected into multiple quadrants. For subject SA65E, IN retina from the OD eye was flash frozen. The IT and macular retina were dissociated and GFP positive cells from these samples were sorted with FACS as before[38]. For subject GR114QB, the IT retinas from both OD and OS eyes were dissociated and GFP positive cells sorted with FACS. The remaining retinas from both eyes were fixed in 4% PFA for 1 hour at room temperature and then transferred to 0.1M PBS with sodium azide and stored at 4° C. For subject JR40D, the IT retinas from both OD and OS eyes were flash frozen. The IN and macular retinas were dissociated and GFP positive cells sorted with FACS. Fixed retina from subject GR114QB was blocked (5 mm in superior/inferior axis, 8 mm in nasal temporal axis), to isolate macular and IN blebs. Embedding of retina blocks consisted of immersion/equilibration in five different, and successive, solutions: 10% sucrose/PB; 20% sucrose/PB; 30% sucrose/PB; 4 parts 30% sucrose/PB to 1 part HistoPrep (Fisher Scientific, Pittsburgh, Pa.); and 2 parts 30% sucrose/PB to 1 part HistoPrep. All incubations took place at room temperature for 30 minutes except the 30% sucrose/PB, which took place overnight at 4 C. Once the final incubation was complete, the tissue was placed in 2 parts 30% sucrose to 1 part Histoprep, oriented, and frozen immediately by partial submersion in liquid nitrogen. Tissue was cut on a cryostat (Leica CM3050 S, Wetzlar, Germany) with the cabinet and object temperatures set at −25° C. and −15° C., respectively. All sections were 10 μm thick. Detailed notes were kept during cryosectioning, keeping track of every section pulled and whether or not that section was mounted or discarded, while periodically monitoring the freshly cut sections with the light microscope. Sectioning in this manner allowed for reasonable orientation within the block, keeping in mind that normal variations occur with cutting at 10 μm, including expansion and contraction of embedding medium. Sections were mounted on Superfrost Plus (Fisher Scientific) slides.

Immunohistochemistry and Microscopy

Retinal cryosections from mice treated with editing reagents were immunostained with antibodies raised against retGC1 (1:5000 generously provided by Dr. Alex Dizhoor, Salus University) or cone arrestin (1:100, generously provided by Dr. Clay Smith, University of Florida). Following an overnight incubation in primary antibodies at 37° C., IgG secondary antibodies Alexafluor-488, Alexafluor-594 or Alexafluor-647 were applied for 1 hr at room temperature. Sections were counterstained with 4', 6'-diaminio-2-phenylindole (DAPI) for 5 min at room temperature.

Macular cryosections from both the OD and OS eyes and IN cryosections from the OD eye of GR114QB were stained. The IN retina from the OS eye was damaged/lost during the initial eye dissection and thus not processed for IHC. All sections were washed three times with 1× PBS (15 minutes each). Samples were then incubated in 0.5% TritonX-100 for 1 hour in the dark at room temperature and blocked in a mixture of 10% goat serum in 1× PBS for 1 hour at room temperature. Slides containing serial retina samples were then incubated with retGC1, cone arrestin, or rhodopsin (1:50, generously provided by Dr. Clay Smith, University of Florida) antibodies described above in a solution containing 1% NHP serum in 1× PBS for approximately 12 hours at 4° C. Samples were then washed three times with 1× PBS (10 minutes each) and incubated for 1 hour at room temperature, with IgG secondary antibodies (Molecular Probes, Eugene, Oreg.) tagged with Alexa-594 (to label retGC1) or Alexa-Cy5 (to label cone arrestin) fluorophores diluted 1:500 in a mixture of 1× PBS containing 3% NHP serum. Autofluorescence eliminator reagent (Cat. #2160; EMD Millipore, Billerica, Mass.) was also applied. Samples were counterstained with DAPI for 5 minutes at room temperature. After a final rinse with 1× PBS, samples were mounted in an aqueous-based media (DAKO) and coverslipped. Confocal images of retinal sections were obtained with a laser scanning Lecia TCS SP8 confocal microscope. Exposure/gain settings remained constant within each experiment.

FACS

Mice were euthanized, retinas were dissociated and GFP+ photoreceptors were collected as previously described[43]. Briefly, immediately following sacrifice, retinas were placed in papain for dissociation (Worthington Papain Dissociation System cat #LK003150). After dissociation, cells were placed in 5% FBS and FACs sorted on a BD FACSAria II. A common template gate was used for all eyes to collect GFP positive photoreceptors. Once collected, cells were pelleted and frozen for further RNA and DNA analysis.

Retinal samples from NHPs were dissociated with papain (Worthington Biochemical Corporation, NJ, Cat #3150) according to the manufacture's protocol and sorted according to the previously published methods with minor modification[38]. In brief, papain was pre-incubated in 5 ml of Earle's Balanced Salt Solution (EBSS) for 10 min at 37° C. After pre-incubation, 250 μl of DNase (dissolved in either 500 μl or 250 μl of EBSS) was added to a final concentration of ~20 or 40 units/ml papain and 0.005% DNase. Dissected retina samples were placed in 15 ml falcon tubes containing 700 μl of papain/DNase and equilibrated with 95% $O_2$:5% $CO_2$. Retina blocks were dissociated by incubation with activated papain at 37° C. for 45 min with constant agitation followed by trituration. Dissociated cells were spun down for 5 min at 2000 rpm and resuspended in 500 μl of resuspension media (430 μl EBSS, 50 μl albumin-ovomucoid inhibitor, 25 μl DNase). To prepare the density gradient, 600 μl of albumin-ovomucoid inhibitor was added to a 15 ml Falcon tube, and the cell suspension layered on top. Following centrifugation for 6 min at 1000 rpm, the cells were gently rinsed with 1× PBS, then resuspended with 1× PBS/5% FBS. Sorting of GFP-positive (GFP+) and unlabeled cells was performed on a BD FACS ARIA SORP equipped with BD FACS Diva software 8.0.1 and a 100 micron nozzle. The filters used to detect the GFP positive fraction were 505LP and 530/30BP (range 515-545 nm) off the Blue 488 nm laser. Sorted cells were then placed into 15 mL tubes and centrifuged at 2500 rpm for 15 minutes. Supernatant was removed and cells were resuspended in 600 uL of RNA later. Samples were then split in half by placing 300 uL of each sample into 1.5 mL tubes.

Nucleic Acid Isolation from Mouse and NHP Retinal Tissue

Genomic DNA was isolated using the DNEasy Blood and Tissue Kit (Qiagen) according to manufacturer's instructions and quantified using Qubit fluorometric quantitation (Thermo Fisher). Total RNA was isolated using the mirVana miRNA Isolation Kit, with phenol (Thermo Fisher) following the total RNA extraction protocol, according to manufacturer's instructions and DNAse treated with Turbo DNA free DNA removal kit (Thermo Fisher).

qRT-PCR

RNA was reverse transcribed using the SuperScript III First-Strand Synthesis SuperMix for qRT-PCR Kit (Thermo) according to manufacturer's instructions except that 1 μL of a 52.5 μM stock of a gene-specific primer for reverse transcribing the gRNA is included (5'-TCTCGC-CAACAAGTTGACGAG-3', SEQ ID NO: 42). The Cas9 mRNA and total genomic RNA are reverse transcribed using the random hexamers present in the master mix reagent. qPCR was performed in triplicate on a CFX384 Real Time PCR Detection System (BioRad) using Taqman Universal PCR Mastermix (Thermo Fisher). Housekeeping gene control was quantified using Thermo Fisher Mouse GAPDH Endogenous Control #4352932E. SaCas9 mRNA and gRNA were quantified.

Sequencing to Determine Editing Efficiency

To determine targeted gene editing efficiency, the region surrounding the gRNA cut site was PCR-amplified from genomic DNA isolated from retinal tissue or sorted PRs. PCR products were cloned into a plasmid backbone using the Zero-Blunt TOPO kit (Thermo Fisher). The TOPO ligation reaction was transformed into chemically competent Top10 cells and individual colonies were isolated and sequenced by GENEWIZ, Inc. Sanger sequencing reads were aligned to reference sequence to quantify rates of targeted gene editing. Non-limiting examples of sequencing results are shown in FIGS. 25 and 26.

Western Blot

Flash frozen mouse retinas and designated retinal blocks from macaque were processed according to previously described methods[44]. The tissue was lysed by sonication (4×5 sec) in 150 microliters of RIPA buffer with Halt Protease Inhibitor (Thermo Scientific Cat #1860932). Cell debris was removed by centrifugation at 14,000 rpm for 10 min at room temperature. The protein concentration of the supernatant was determined with bicinchoninic acid (BCA) (Thermo Fisher Scientific), and equal amounts of protein were separated on 4-20% polyacrylamide gels (BioRad, Hercules, Calif.) and subsequently transferred onto polyvinylidene difluoride (PVDF) membranes (Millipore, Billerica, Mass.). Blots were labeled with antibodies specific for saCas9, β-actin (1:5000; Abcam, Cambridge, Mass.), retGC1 (1:20,000, generously provided by Dr. Alex Dizhoor, Salus University), GCAP1 ("UW101", 1:20,000, generously provided by Dr. Wolfgang Baehr, University of Utah) and/or cone arrestin (1:00) generously provided by Dr. Clay Smith, University of Florida). Both retGC1 and GCAP1 expression in macaque retinas were normalized to cone arrestin.

Neutralizing Antibody Assays

NHP serum was screened for the presence of neutralizing antibodies against AAV5 prior to purchase according to previously published methods[29]. ARPE-19 cells (ATCC, Manassas, Va.) were maintained in a culture medium consisting of Dulbecco's modified Eagle's medium (DMEM)—Nutrient Mixture F-12, 1:1 mixture with Hepes buffer containing 10% fetal bovine serum (FBS), 0.384% (w/v) additional sodium bicarbonate, 1% 200 Mm L-glutamine, and 50 mg/ml Gentamicin. Cells were incubated at 37 C in 7% CO2. Serum samples from subjects SA65E, GR114QB, and JR40D and naive serum from a mouse (Sigma) were heat-inactivated at 56° C. for 35 minutes. Self-complimentary AAV5-smCBA-mCherry vector ($10^4$ genomic copies per cell) was diluted in serum-free DMEM/F-12 1:1 modified medium and incubated with a series of dilutions (1:10, 1:40, 1:160) of heat-inactivated serum samples in DMEM/F-12 1:1 modified medium for 1 hour at 37° C. The serum-vector mixture was then used to infect ARPE-19 cells seeded in 96-well plates containing $3 \times 10^4$ cells/well for 1 hour. After 1 hour incubation, an equal volume of 20% FBS DMEM/F-12 1:1 modified medium was added to each well and incubated for 72 hours at 37° C. in 7% $CO_2$. Three days post-infection, cells were observed under a fluorescent microscope to confirm reporter gene expression (EVOS XL Core). Cells were then dissociated with Accutase solution (MP Biomedicals, Solon, Ohio), and 10,000 cells per sample were counted and analyzed using a BD LSR II flow cytometer equipped with BD FACSDIVA 6.2 software (BD Biosciences, San Jose, Calif.). mCherry fluorescence was quantified with a PE-Texas-Red-A filter with an excitation wavelength of 532 nm and an emission band pass of 600-620 nm. The transduction efficiency was calculated by multiplying the percentage of cells positive for mCherry by the mean fluorescence intensity[45,46]. The neutralizing antibody (nAb) titer was reported as the highest serum dilution that inhibited self-complementary AAV5-smCBA-mCherry transduction (mCherry expression) by >50%, compared with naive serum control. Serum samples were collected pre-treatment and post-treatment. A sample taken from an animal not utilized in this study that was shown previously to be strongly neutralized by AAV5 was used as a positive control.

Guanylate Cyclase Activity Assays $GC1^{+/-}$:$GC2^{-/-}$ (n=4) mice were dark-adapted overnight, sacrificed under infrared illumination, and their retinas extracted and assayed for guanylate cyclase activity in the dark using [$\alpha$-$^{32}$P]GTP as a substrate according to a previously described protocol[47,48]. The assay mixture (25 μL) contained 30 mM MOPS-KOH (pH 7.2), 60 mM KCl, 4 mM NaCl, 1 mM DTT, 2 mM $Ca^{2+}$/EGTA buffer, 1 mM free $Mg^{2+}$, 0.3 mM ATP, 4 mM cGMP, 1 mM GTP, 1 μCi of [$\alpha$-$^{32}$P]GTP, 0.1 μCi of [8-$^3$H]cGMP (Perkin Elmer, Waltham, Mass.), phosphodiesterase inhibitors zaprinast and dipyridamole, 10 mM creatine phosphate, and 0.5 unit of creatine phosphokinase. The resultant [$^{32}$P]cGMP product, together with the internal standard of [8-$^3$H]cGMP, was purified using fluorescently backed polyethyleneimine cellulose thin-layer chromatography plate (Merck, Whitehouse Station, N.J.) as described previously[49], and the radioactivity of both tracers was counted after elution in 1 M LiCl using ScintiSafe scintillation cocktail (Fisher/Thermo Scientific, Waltham, Mass.) containing 20% ethanol. $Ca^{2+}$/EGTA buffers containing calibrated free $Ca^{2+}$ and $Mg^{2+}$ concentrations were prepared using published methods[50] and verified by fluorescent $Ca^{2+}$ indicator dyes as previously described[51].

REFERENCES CITED

1. Dizhoor A M, Lowe D G, Olshevskaya E V, Laura R P, Hurley J B. The human photoreceptor membrane guanylyl cyclase, RetGC, is present in outer segments and is regulated by calcium and a soluble activator. Neuron 1994; 12:1345-52.
2. Liu X, Seno K, Nishizawa Y, et al. Ultrastructural localization of retinal guanylate cyclase in human and monkey retinas. Exp Eye Res 1994; 59:761-8.
3. Olshevskaya E V, Peshenko I V, Savchenko A B, Dizhoor A M. Retinal guanylyl cyclase isozyme 1 is the preferential in vivo target for constitutively active GCAP1 mutants causing congenital degeneration of photoreceptors. The Journal of neuroscience: the official journal of the Society for Neuroscience 2012; 32:7208-17.
4. Burns M E, Arshaysky V Y. Beyond counting photons: trials and trends in vertebrate visual transduction. Neuron 2005; 48:387-401.
5. Karan S, Frederick J M, Baehr W. Novel functions of photoreceptor guanylate cyclases revealed by targeted deletion. Mol Cell Biochem 2010; 334:141-55.
6. Payne A M, Morris A G, Downes S M, et al. Clustering and frequency of mutations in the retinal guanylate cyclase (GUCY2D) gene in patients with dominant cone-rod dystrophies. Journal of medical genetics 2001; 38:611-4.

7. Mukherjee R, Robson A G, Holder G E, et al. A detailed phenotypic description of autosomal dominant cone dystrophy due to a de novo mutation in the GUCY2D gene. Eye (Lond) 2014; 28:481-7.
8. Tucker C L, Woodcock S C, Kelsell R E, Ramamurthy V, Hunt D M, Hurley J B. Biochemical analysis of a dimerization domain mutation in RetGC-1 associated with dominant cone-rod dystrophy. Proc Natl Acad Sci USA 1999; 96:9039-44.
9. Wilkie S E, Newbold R J, Deery E, et al. Functional characterization of missense mutations at codon 838 in retinal guanylate cyclase correlates with disease severity in patients with autosomal dominant cone-rod dystrophy. Human molecular genetics 2000; 9:3065-73.
10. Dizhoor A M, Olshevskaya E V, Peshenko I V. The R838S Mutation in Retinal Guanylyl Cyclase 1 (RetGC1) Alters Calcium Sensitivity of cGMP Synthesis in the Retina and Causes Blindness in Transgenic Mice. The Journal of biological chemistry 2016; 291:24504-16.
11. Sato S, Peshenko I V, Olshevskaya E V, Kefalov V J, Dizhoor A M. GUCY2D Cone-Rod Dystrophy-6 Is a "Phototransduction Disease" Triggered by Abnormal Calcium Feedback on Retinal Membrane Guanylyl Cyclase 1. The Journal of neuroscience: the official journal of the Society for Neuroscience 2018; 38:2990-3000.
12. Green D R, Reed J C. Mitochondria and apoptosis. Science 1998; 281:1309-12.
13. Gregory-Evans K, Kelsell R E, Gregory-Evans C Y, et al. Autosomal dominant cone-rod retinal dystrophy (CORD6) from heterozygous mutation of GUCY2D, which encodes retinal guanylate cyclase. Ophthalmology 2000; 107:55-61.
14. Moore A T. Cone and cone-rod dystrophies. Journal of medical genetics 1992; 29:289-90.
15. Hsu P D, Lander E S, Zhang F. Development and applications of CRISPR-Cas9 for genome engineering. Cell 2014; 157:1262-78.
16. Sander J D, Joung J K. CRISPR-Cas systems for editing, regulating and targeting genomes. Nature biotechnology 2014; 32:347-55.
17. Doudna J A, Charpentier E. Genome editing. The new frontier of genome engineering with CRISPR-Cas9. Science 2014; 346:1258096.
18. Barrangou R, Doudna J A. Applications of CRISPR technologies in research and beyond. Nature biotechnology 2016; 34:933-41.
19. Maeder M L, Gersbach C A. Genome-editing Technologies for Gene and Cell Therapy. Mol Ther 2016; 24:430-46.
20. Yin H, Xue W, Chen S, et al. Genome editing with Cas9 in adult mice corrects a disease mutation and phenotype. Nature biotechnology 2014; 32:551-3.
21. Ousterout D G, Kabadi A M, Thakore P I, Majoros W H, Reddy T E, Gersbach C A. Multiplex CRISPR/Cas9-based genome editing for correction of dystrophin mutations that cause Duchenne muscular dystrophy. Nature communications 2015; 6:6244.
22. Tabebordbar M, Zhu K, Cheng J K W, et al. In vivo gene editing in dystrophic mouse muscle and muscle stem cells. Science 2016; 351:407-11.
23. Yu W, Mookherjee S, Chaitankar V, et al. Nrl knockdown by AAV-delivered CRISPR/Cas9 prevents retinal degeneration in mice. Nature communications 2017; 8:14716.
24. Ruan G X, Barry E, Yu D, Lukason M, Cheng S H, Scaria A. CRISPR/Cas9-Mediated Genome Editing as a Therapeutic Approach for Leber Congenital Amaurosis 10. Mol Ther 2017; 25:331-41.
25. Boye S E, Boye S L, Lewin A S, Hauswirth W W. A comprehensive review of retinal gene therapy. Mol Ther 2013; 21:509-19.
26. Jacobson S G, Boye S L, Aleman T S, et al. Safety in nonhuman primates of ocular AAV2-RPE65, a candidate treatment for blindness in Leber congenital amaurosis. Hum Gene Ther 2006; 17:845-58.
27. Maclachlan T K, Lukason M, Collins M, et al. Preclinical safety evaluation of AAV2-sF. Mol Ther 2011; 19:326-34.
28. Ye G J, Budzynski E, Sonnentag P, et al. Cone-Specific Promoters for Gene Therapy of Achromatopsia and Other Retinal Diseases. Hum Gene Ther 2016; 27:72-82.
29. Boye S E, Alexander J J, Boye S L, et al. The human rhodopsin kinase promoter in an AAV5 vector confers rod- and cone-specific expression in the primate retina. HumGene Ther 2012; 23:1101-15.
30. Beltran W A, Cideciyan A V, Boye S E, et al. Optimization of Retinal Gene Therapy for X-Linked Retinitis Pigmentosa Due to RPGR Mutations. Mol Ther 2017.
31. Bakondi B, Lv W, Lu B, et al. In Vivo CRISPR/Cas9 Gene Editing Corrects Retinal Dystrophy in the S334ter-3 Rat Model of Autosomal Dominant Retinitis Pigmentosa. Mol Ther 2016; 24:556-63.
32. Hung S S, Chrysostomou V, Li F, et al. AAV-Mediated CRISPR/Cas Gene Editing of Retinal Cells In Vivo. Invest Ophthalmol Vis Sci 2016; 57:3470-6.
33. Bae S, Park J, Kim J S. Cas-OFFinder: a fast and versatile algorithm that searches for potential off-target sites of Cas9 RNA-guided endonucleases. Bioinformatics 2014; 30:1473-5.
34. Yang R B, Robinson S W, Xiong W H, Yau K W, Birch D G, Garbers D L. Disruption of a retinal guanylyl cyclase gene leads to cone-specific dystrophy and paradoxical rod behavior. J Neurosci 1999; 19:5889-97.
35. Zolotukhin S. Production of recombinant adeno-associated virus vectors. Hum Gene Ther 2005; 16:551-7.
36. Timmers A M, Zhang H, Squitieri A, Gonzalez-Pola C. Subretinal injections in rodent eyes: effects on electrophysiology and histology of rat retina. Mol Vis 2001; 7:131-7.
37. Cideciyan A V, Aleman T S, Boye S L, et al. Human gene therapy for RPE65 isomerase deficiency activates the retinoid cycle of vision but with slow rod kinetics. Proc Natl Acad Sci USA 2008; 105:15112-7.
38. Choudhury S, Strang C E, Alexander J J, et al. Novel Methodology for Creating Macaque Retinas with Sortable Photoreceptors and Ganglion Cells. Front Neurosci 2016; 10:551.
39. Pang J J, Dai X, Boye S E, et al. Long-term retinal function and structure rescue using capsid mutant AAV8 vector in the rd10 mouse, a model of recessive retinitis pigmentosa. Mol Ther 2011; 19:234-42.
40. Boye S L, Peshenko I V, Huang W C, et al. AAV-mediated gene therapy in the guanylate cyclase (RetGC1/RetGC2) double knockout mouse model of Leber congenital amaurosis. Hum Gene Ther 2013; 24:189-202.
41. Boye S L, Conlon T, Erger K, et al. Long-term preservation of cone photoreceptors and restoration of cone function by gene therapy in the guanylate cyclase-1 knockout (GC1KO) mouse. Invest Ophthal mol Vis Sci 2011; 52:7098-108.
42. Boye S E, Alexander J J, Witherspoon C D, et al. Highly Efficient Delivery of Adeno-Associated Viral Vectors to the Primate Retina. Hum Gene Ther 2016; 27:580-97.

43. Kay C N, Ryals R C, Aslanidi G V, et al. Targeting photoreceptors via intravitreal delivery using novel, capsid-mutated AAV vectors. PLoS One 2013; 8:e62097.
44. Molday R S. Focus on molecules: retinoschisin (RS1). Exp Eye Res 2007; 84:227-8.
45. Ryals R C, Boye S L, Dinculescu A, Hauswirth W W, Boye S E. Quantifying transduction efficiencies of unmodified and tyrosine capsid mutant AAV vectors in vitro using two ocular cell lines. Mol Vis 2011; 17:1090-102.
46. Boye S L, Bennett A, Scalabrino M L, et al. Impact of Heparan Sulfate Binding on Transduction of Retina by Recombinant Adeno-Associated Virus Vectors. Journal of virology 2016; 90:4215-31.
47. Olshevskaya E V, Calvert P D, Woodruff M L, et al. The Y99C mutation in guanylyl cyclase-activating protein 1 increases intracellular Ca2+ and causes photoreceptor degeneration in transgenic mice. J Neurosci 2004; 24:6078-85.
48. Peshenko I V, Olshevskaya E V, Savchenko A B, et al. Enzymatic properties and regulation of the native isozymes of retinal membrane guanylyl cyclase (RetGC) from mouse photoreceptors. Biochemistry 2011; 50:5590-600.
49. Olshevskaya E V, Hughes R E, Hurley J B, Dizhoor A M. Calcium binding, but not a calcium-myristoyl switch, controls the ability of guanylyl cyclase-activating protein GCAP-2 to regulate photoreceptor guanylyl cyclase. The Journal of biological chemistry 1997; 272:14327-33.
50. Tsien R, Pozzan T. Measurement of cytosolic free Ca2+ with quin2. Methods Enzymol 1989; 172:230-62.
51. Peshenko I V, Dizhoor A M. Ca2+ and Mg2+ binding properties of GCAP-1. Evidence that Mg2+-bound form is the physiological activator of photoreceptor guanylyl cyclase. The Journal of biological chemistry 2006; 281: 23830-41.
52. Khani S C, Pawlyk B S, Bulgakov O V, et al. AAV-mediated expression targeting of rod and cone photoreceptors with a human rhodopsin kinase promoter. Invest Ophthal mol Vis Sci 2007; 48:3954-61.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A method of treating cone-rod dystrophy type 6 (CORD6) in a subject, the method comprising injecting into an eye of the subject having CORD6:
   a first nucleic acid that encodes a guide RNA (gRNA) that targets both an autosomal dominant allele of a guanylate cyclase 2D (GUCY2D) gene and a wild-type allele of a GUCY2D gene in the subject,
   a second nucleic acid that encodes an RNA-guided endonuclease, and
   a replacement nucleic acid that comprises a functional GUCY2D gene that is hardened such that the gRNA no longer recognizes a target site in the gene, or the RNA-guided endonuclease no longer recognizes the protospacer adjacent motif (PAM) site adjacent to the target site.

2. The method of claim 1, wherein the first and second nucleic acids are administered in one or more recombinant AAV (rAAV) particles, and/or wherein the replacement nucleic acid is administered in one or more rAAV particles.

3. The method of claim 2, wherein the one or more rAAV particles comprise rAAV capsid proteins of the AAV5, AAV8, AAV9, AAVrh10, AAVrh8, Anc80, AAV 44.9, AAV2 (triple Y-F), AAV2(quad Y-F+T-V), or AAV2(MAX)deltaHS serotype.

4. The method of claim 2, wherein the first and second nucleic acids and the replacement nucleic acid, or the one or more rAAV particles, are injected intravitreally to one or both eyes of the subject.

5. The method of claim 2, wherein the first and second nucleic acids and the replacement nucleic acid, or the one or more rAAV particles, are injected subretinally to one or both eyes of the subject.

6. The method of claim 2, wherein the first and second nucleic acids and the replacement nucleic acid, or the one or more rAAV particles, are administered via a suprachoroidal injection to one or both eyes of the subject.

7. The method of claim 1, wherein the replacement nucleic acid comprises a functional GUCY2D gene that is hardened such that the gRNA no longer recognizes a target site in the gene.

8. The method of claim 1, wherein the first nucleic acid comprises a first promoter operatively connected to a gene encoding the gRNA, and wherein the first promoter is selected from the group consisting of U6, H1, opsin, rhodopsin kinase, cone-rod homeobox (CRX), FLT3 interacting zinc finger 1 (FIZ1), cytomegalovirus (CMV), chicken beta actin (CBA), elongation factor-1 alpha (EF1a), neural retina-specific leucine zipper protein (Nrl), interphotoreceptor retinoid-binding protein (IRBP), chimeric IRBP-G protein subunit alpha transducin 2 (IRBP-GNAT2), and Cone Arrestin promoters.

9. The method of claim 1, wherein the second nucleic acid comprises a second promoter operatively connected to a gene encoding the RNA-guided endonuclease, and wherein the second promoter is selected from the group consisting of U6, H1, opsin, rhodopsin kinase, CRX, FIZ1, CMV, CBA, EF1a, Nrl, IRBP, IRBP-GNAT2, and Cone Arrestin promoters.

10. The method of claim 1, wherein the replacement nucleic acid comprises a replacement promoter that is operatively connected to a replacement functional GUCY2D gene, and wherein the replacement promoter is selected from the group consisting of U6, H1, opsin, rhodopsin kinase, CRX, FIZ1, CMV, CBA, EF1a, Nrl, IRBP, IRBP-GNAT2, and Cone Arrestin promoters.

11. The method of claim 1, wherein the RNA-guided endonuclease is a Cas9.

12. The method of claim 1, wherein the RNA-guided endonuclease is a modified Cas9 that is selective for the autosomal dominant allele of GUCY2D.

13. The method of claim 1, wherein the subject has a symptom selected from the group consisting of loss of visual acuity, abnormal color vision, photophobia, visual field loss, macular atrophy, rod degeneration, and loss of peripheral visual field.

14. The method of claim 1, wherein the replacement nucleic acid comprises a hardened GUCY2D gene from a non-human primate species.

15. The method of claim 1, wherein the subject is human.

* * * * *